US009234169B2

(12) United States Patent
Nystedt et al.

(10) Patent No.: US 9,234,169 B2
(45) Date of Patent: Jan. 12, 2016

(54) ENZYMATICAL MODIFICATION OF CELL GLYCOSYLATION USING SERUM ALBUMIN AND DIVALENT CATIONS

(75) Inventors: Johanna Nystedt, Helsinki (FI); Heidi Anderson, Helsinki (FI); Leena Valmu, Helsinki (FI); Jari Natunen, Vantaa (FI); Tero Satomaa, Helsinki (FI)

(73) Assignee: Glykos Finland, Helsinki (FI)

( * ) Notice: Subject to any disclaimer, the term of this patent is extended or adjusted under 35 U.S.C. 154(b) by 1321 days.

(21) Appl. No.: 13/054,541

(22) PCT Filed: Jul. 16, 2009

(86) PCT No.: PCT/FI2009/050628
§ 371 (c)(1),
(2), (4) Date: Feb. 15, 2011

(87) PCT Pub. No.: WO2010/007214
PCT Pub. Date: Jan. 21, 2010

(65) Prior Publication Data
US 2011/0136203 A1    Jun. 9, 2011

(30) Foreign Application Priority Data
Jul. 16, 2008  (EP) ..................................... 08397517

(51) Int. Cl.
| C12P 21/04 | (2006.01) |
| C12N 9/10 | (2006.01) |
| C12N 5/071 | (2010.01) |
| C07H 21/04 | (2006.01) |
| C12N 5/00 | (2006.01) |
| C12P 21/00 | (2006.01) |
| C12N 5/0775 | (2010.01) |
| A61K 35/12 | (2015.01) |

(52) U.S. Cl.
CPC ............ *C12N 5/0006* (2013.01); *C12N 5/0663* (2013.01); *C12N 9/1051* (2013.01); *C12P 21/005* (2013.01); *A61K 2035/124* (2013.01); *C12N 2501/70* (2013.01)

(58) Field of Classification Search
CPC .............................. C12P 9/1051; C12P 21/005
See application file for complete search history.

(56) References Cited

U.S. PATENT DOCUMENTS

| 5,728,554 | A | 3/1998 | Bayer et al. |
| 5,858,752 | A | 1/1999 | Seed et al. |
| 5,965,457 | A | 10/1999 | Magnani |
| 6,232,450 | B1 | 5/2001 | Wong |
| 6,534,298 | B2 | 3/2003 | Taylor et al. |
| 6,962,806 | B2 | 11/2005 | Taylor et al. |
| 7,029,891 | B2 | 4/2006 | Taylor et al. |
| 7,166,449 | B2 | 1/2007 | Taylor et al. |
| 2002/0058313 | A1 | 5/2002 | Renkonen et al. |
| 2003/0040607 | A1 | 2/2003 | Sackstein |
| 2003/0124645 | A1 | 7/2003 | Paulson et al. |
| 2003/0153030 | A1 | 8/2003 | Otto et al. |
| 2003/0165480 | A1 | 9/2003 | Zhu |
| 2004/0132640 | A1 | 7/2004 | DeFrees et al. |
| 2004/0209357 | A1 | 10/2004 | Xia et al. |
| 2004/0253233 | A1 | 12/2004 | Del Rio et al. |
| 2005/0014718 | A1 | 1/2005 | Natunen et al. |
| 2006/0003924 | A1 | 1/2006 | Sackstein |
| 2006/0210558 | A1 | 9/2006 | Sackstein |
| 2007/0148728 | A1 | 6/2007 | Johnson et al. |
| 2007/0170463 | A1 | 7/2007 | Ueno et al. |
| 2007/0258986 | A1 | 11/2007 | Qasba et al. |
| 2008/0044383 | A1 | 2/2008 | Sackstein |

FOREIGN PATENT DOCUMENTS

| WO | 9116900 | 11/1991 |
| WO | 9402616 | 2/1994 |
| WO | 9423021 | 10/1994 |
| WO | 9640881 | 12/1996 |
| WO | 9732889 | 9/1997 |
| WO | 0014199 | 3/2000 |
| WO | 0049153 | 8/2000 |
| WO | 0188117 A2 | 11/2001 |
| WO | 0244342 | 6/2002 |
| WO | 02088351 A1 | 11/2002 |
| WO | 03016464 | 2/2003 |
| WO | 03105908 A2 | 12/2003 |
| WO | 2004009838 | 1/2004 |
| WO | 2004017810 | 3/2004 |
| WO | 2004019040 | 3/2004 |
| WO | 2004072306 A1 | 8/2004 |
| WO | 2004094619 | 11/2004 |
| WO | 2005014024 A2 | 2/2005 |
| WO | 2005017115 | 2/2005 |
| WO | 2005092391 A2 | 10/2005 |

(Continued)

OTHER PUBLICATIONS

Gu et al. "Regulation of Integrin Functions by N-glycans", Glycoconjugate Journal 2004, vol. 21, p. 9-15.
Rini et al. "Carbohydrates and glycoconjugates Flycosyltransferases, sugar nucleotide transporters and bacterial surface lectins—at the cutting edge of glycobiology", Current Opinion in Structural Biology 2000, vol. 10, p. 507-509.
Evans et al. "Glycosyltransferase Activity in Developing Sea-Urchin Embryos", J. Cell Sci. 1977, vol. 25, p. 355-366.
International Search Report for PCT/FI2009/050628, Completed by the Swedish Patent Office on Oct. 23, 2009, 6 Pages.

(Continued)

*Primary Examiner* — Yong Pak
(74) *Attorney, Agent, or Firm* — Brooks Kushman P.C.

(57) ABSTRACT

The invention is directed to a method and kit to control and modify the status of cells, such as human stem cells, by changing their glycosylation, in particular sialylation and fucosylation, levels in a reaction condition where culture medium reagents, such as divalent cations, are present and cells are kept non-adherent. The invention is further directed to novel stem cells, the glycosylation of which has been specifically altered.

6 Claims, 14 Drawing Sheets

(56) References Cited

FOREIGN PATENT DOCUMENTS

| WO | 2006068720 | | 6/2006 |
|---|---|---|---|
| WO | 2007006864 | A2 | 1/2007 |
| WO | 2007054620 | A1 | 5/2007 |
| WO | 2007143204 | A2 | 12/2007 |
| WO | 2008011094 | A2 | 1/2008 |
| WO | 2008087256 | A1 | 7/2008 |
| WO | 2008087260 | A1 | 7/2008 |

OTHER PUBLICATIONS

Hidalgo et al. "Enforced fucosylation of neonatal CD34= cells generates selectin ligands that enhance the initial interactions with microvessels but not homing to bone marrow", Blood Jan. 15, 2005, vol. 105, No. 2, p. 567-575.

Sackstein et al. "Ex vivo glycan engineering of CD44 programs human miltipotent mesenchymal stromal cell trafficking to bone", Nature Medicine Feb. 2008, vol. 14, No. 2, p. 181-187.

Xia et al. "Surface fucosylation of human cord blood cells augments binding to P-selectin and E-selectin and enhances engraftment in bone marrow", Blood Nov. 15, 2004, vol. 104, No. 10, p. 3091-3099.

Search Report for EP 08397517.7, Completed by the European Patent Office on May 5, 2009, 9 Pages.

Beyer et al. "Enzymatic Properties of the B-Galactoside a1 → 2 Fucosyltransferase from Porcine Submaxillary Gland", The Journal of Biological Chemistry 1980, vol. 255, No. 11, Issue of Jun. 10, p. 5373-5379.

Eppler et al. "Ganglioside Biosynthesis in Rat Liver: Characterization of Cytidine-5'-Monophospho-N-Acetylneuraminic Acid:Hematoside (Gm3) Sialyltransferase", Biochimica Et Biophysica Acta 1980, vol. 619, p. 318-331.

Freischutz et al. "Characterization of Sialyltransferase-IV Activity and Its Involvement in the c-Pathway of Brain Ganglioside Metabolism", Journal of Neurochemistry 1995, vol. 64, p. 385-393.

Kaminska et al. "Purification and characterization of GDP-L-Fuc: N-acetyl B-D-glucosaminide a1 → 6fucosyltransferase from human blood platelets", Glycoconjugate Journal 1998, vol. 15, p. 783-788.

Lairson et al. "Glycosyltransferases: Structures, Functions, and Mechanisms", Annu. Rev. Biochem. 2008, vol. 77, p. 251-555.

Britten et al., "Acceptor specificity of the human leukocyte a3 fucosyltransferase: role of FucT-VII in the generation of selectin ligands.", Glycobiology, vol. 8, No. 4, pp. 321-327, Apr. 1998.

De Vries et al., "Acceptor specificity of GDP-Fuc:GalB1→4GlcNAc-R a3-fucosyltransferase VI (FucT VI) expressed inj insect cells as soluble, secreted enzyme.", Glycobiology, vol. 7, No. 7, pp. 921-927, Oct. 1997.

Ernst et al., "False sugar sequence ions in electrospray tandem mass spectrometry of underivatized sialyl-Lewis type oligosaccharides.", 1997. International Journal of Mass Spectrometry and Ion Processes, vol. 160, pp. 283-290.

Greenwell et al., "Fucosyltransferase activities in human lymphocytes and granulocytes", FEBS Letters 1011, vol. 164, No. 2, pp. 314-317, Dec. 1983.

Ivannikova et al., "Recombinant (2→3)-a-sialyltransferase immobilized on nickel-Agarose for preparative synthesis of sialyl Lewis X and Lewis A precursor oligosaccharides.", Carbohydrate Research, vol. 338, pp. 1153-1161, May 23, 2003.

Kudo et al., "Characterization of the Major Core Structures of the a2?8-linked Polysialic Acid-containing Glycan Chains Present in Neural Cell Adhesion Molecule in Embryonic Chick Brains," The Journal of Biological Chemistry, vol. 271, No. 51, 1996, pp. 32667-32677.

Li et al., "Abstracts submitted for the joint meeting of the society for glycobiology and the Japanese society for carbohydrate research." Nov. 17-20, 2004 Abs.

Lowe., "Glycosylation in the control of selectin counter-receptor structure and function", Immunological Reviews, vol. 186, pp. 19-36, Aug. 2002.

Martin et al., "Human embryonic stem cells express an immunogenic nonhuman sialic acid", Technical Reports, Nature Medicine, vol. 11, No. 2, Jan. 30, 2005, pp. 228-232.

Minch et al., "Tissue Plasminogen Activator Coexpressed in Chinese Hamster Ovary Cells with (2,6)-Sialyltransferase Contains NeuAc(2,6)Gal (1,4)Glc-N-AcR Linkages", Biotechnol. Prog. vol. 11, 1995, pp. 348-351.

Murray et al., "Mechanism and Specificity of Human-1,3-Fucosyltransferase V", Biochemistry, vol. 35, pp. 11183-11195, Aug. 27, 1996.

Palma et al., "Effect of the manganese ion on human a 3/4 fucosyltransferase III activity", Biometals, vol. 17, pp. 35-43, 2004. Published online Jun. 2003.

Podolsky et al., "Galactosyltransferase and Concanavalin A Agglutination of Cells", Proc. Nat. Acad. Sci., vol. 71, No. 3, pp. 904-908, Mar. 1974.

Romanov et al., "Searching for Alternative Sources of Postnatal Human Mesenchymal Stem Cells: Candidtate MSC-Like Cells from Umbilical Cord.", Stem Cells 2003, vol. 21, pp. 105-110.

Ruster et al., "Mesenchymal Stem Cells Display Coordinated Rolling and Adhesion Behavior on Endothelial Cells under Shear Flow.", Blood ASH Annual Meeting Abstracts 2004, vol. 104, Abstract 670.

Sasaki et al., "Expression Cloning of a Novel a 1,3-Fucosyltransferase That is Involved in Biosynthesis of the Sialyl Lewis x Carbohydrate Determinants in Leukocytes.", J. Bio. Chem. May 20, 1994, vol. 269, No. 20, pp. 14730-14737.

Sasaki H et al., "Carbohydrate Structure of Erythropoietin Expressed in Chinese Hamster Ovary Cells by a Human Erythropoietin cDNA.", Journal of Biological Chemistry 1987, vol. 262, No. 25, pp. 12059-12076.

Schwartz-Albiez et al., "Cell surface sialylation and ecto-sialyltransferase activity of human CD34 progenitors from peripheral blood and bone marrow", Glycoconjugate Journal Aug. 2004, vol. 21, pp. 451-459.

Srivastava et al., "Enzymatic transfer of a preassembled trisaccharide antigen to cell surfaces using a fucosyltransferase.", J. Bio. Chem. Nov. 5, 1992, vol. 267, No. 31, pp. 22356-22361.

Tsuboi et al., "Acquisition of P-selectin Binding Activity by en Bloc Transfer of Sulfo Lewis X Trisaccharide to the Cell Surface: Comparison to a Sialyl le x Tetrasaccharide Transferred on the Cell Surface.", Archives of Biochem. and Biophysics Feb. 1, 2000, vol. 374, No. 1, pp. 100-106.

Unverzagt et al., "Structure-Activity Profiles of Complex Biantennary Glycans with Core Fucosylation and with/without Additional. 2,3/a 2,6 Sialylation: Synthesis of Neoglycoproteins and Their Properties in Lectin Assays, Cell Binding and Organ Uptake," J. Med. Chem. 2002, vol. 45, pp. 478-491.

Wang et al., "Purification and Characterization of a GDP-fucose:Polypeptide Fucosyltransferase from Chinese Hamster Ovary Cells.", J. of Biological Chemistry Apr. 3, 1998, vol. 273, No. 14, pp. 8112-8118.

Figures 11A-D
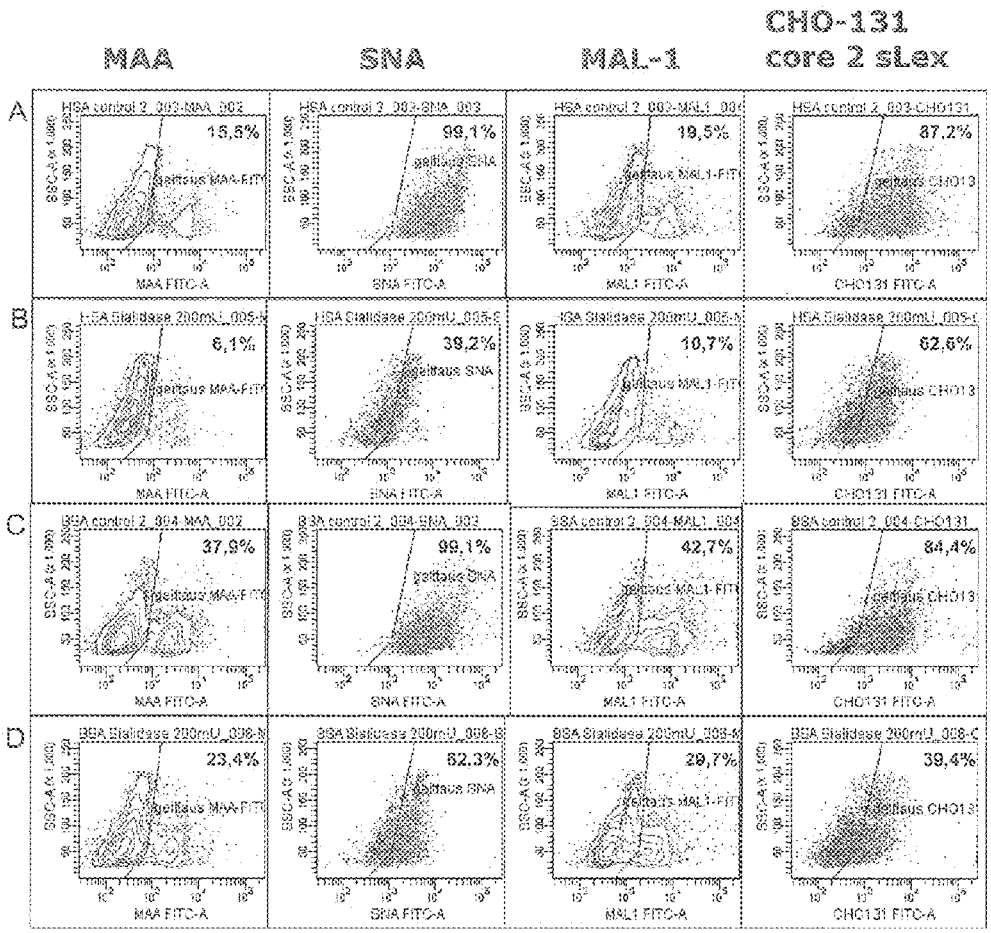

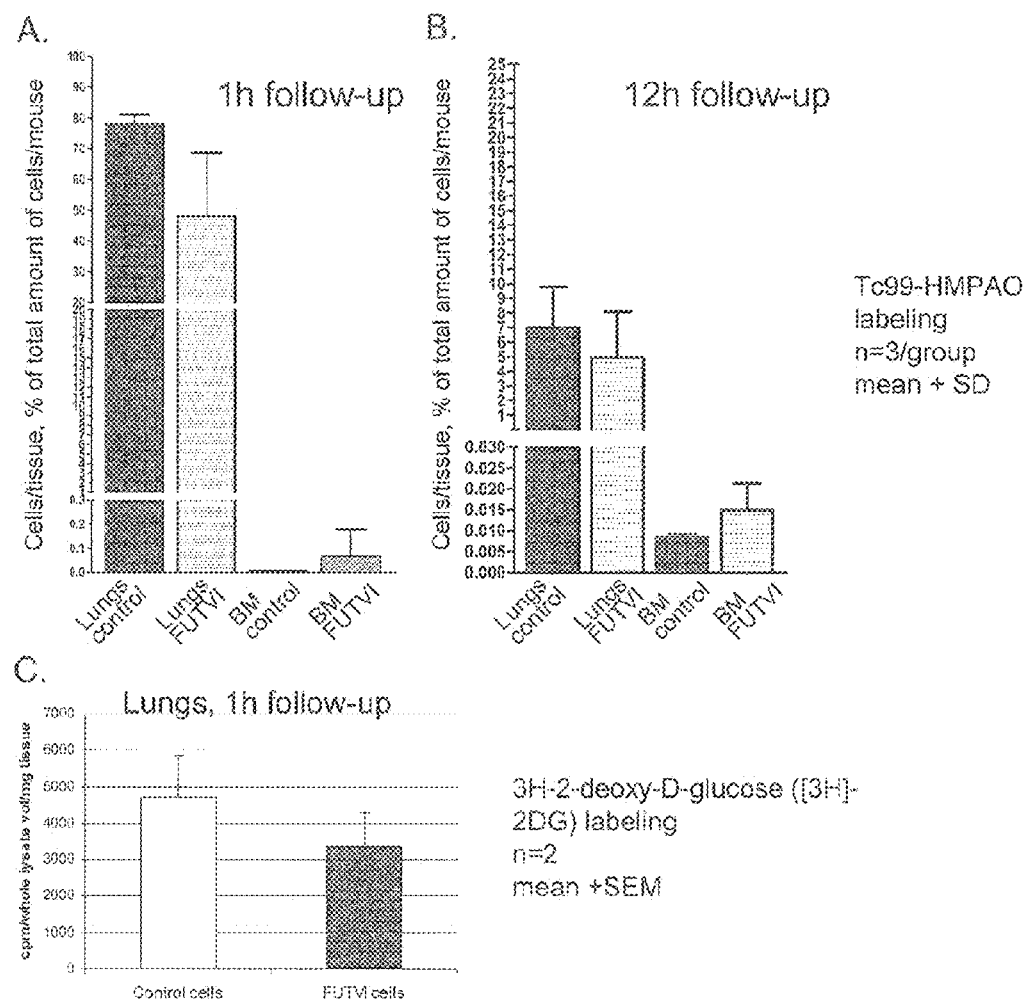
Figures 12A-C

Figure 13
Cells in 80% confluency
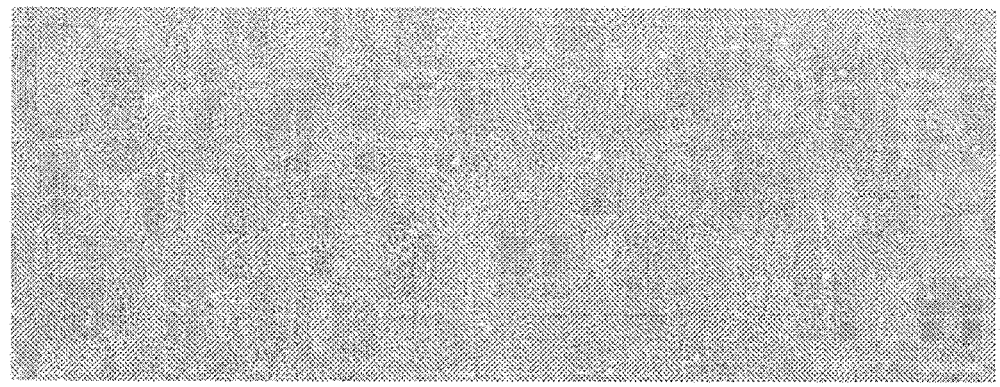
SAT 1h					Neuraminidase 1h
Neuraminidase 1h + SAT1h			Incubation control
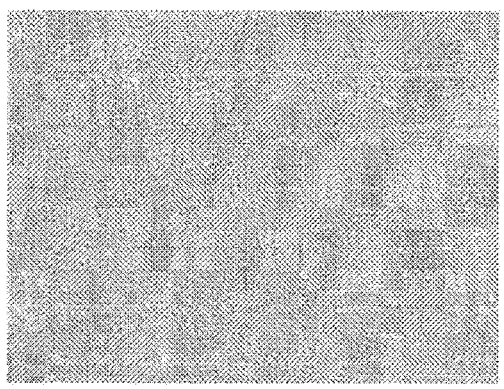
Control cells without treatments

ENZYMATICAL MODIFICATION OF CELL GLYCOSYLATION USING SERUM ALBUMIN AND DIVALENT CATIONS

FIELD OF THE INVENTION

The invention is directed to a method and kit to control and modify the status of cells, such as human stem cells, by changing their glycosylation, in particular sialylation and fucosylation, levels in a reaction condition where culture medium reagents, such as divalent cations, are present and cells are kept non-adherent. The invention is further directed to novel stem cells, the glycosylation of which has been specifically altered.

BACKGROUND OF THE INVENTION

PCT/FI2006/050323 published 18.1.2007, describes a modification of glycosylation of stem cells. The examples show reaction of human cord blood mononuclear cells, comprising hematopoietic stem cells, with sialyltransferase and fucosyltransferases in MOPS buffer and 150 mM NaCl and by sialidases in acetate buffer.

The "Sackstein" application (WO 2007/143204) indicates, and their corresponding publication in Nature Medicine, filed after the priority date of the above application, claims specifically reaction conditions without any divalent cations and the application specifically shows toxicity of $MnCl_2$. Based on the prior art it would not appear useful to use toxic $Mn^{2+}$ or other divalent cations $Mg^{2+}$ or $Ca^{2+}$-ions in the reactions.

WO 2008/011094 also by Sackstein describes the use of cytokines to stimulate glycosylation enzymes on hematopoietic stem cells. The present invention is directed to the use of non-toxic divalent cations, small molecules and supporting non-glycoprotein albumin in context of in vitro modification of especially adherent cell. It is realized that activation of cells by cytokines may also produce undesired differentiation or cell activation leading to negative activities in context of in vivo or ex vivo uses of the cell.

PCT/FI2008/050015, filed 18.1.2008, by the present inventors indicates that the reactions even with the adherent cells can be performed in the presence of $Mg^{2+}$, which would be preferred for the activity of modification enzymes, especially sialyltransferase and fucosyltransferase. The example includes reactions to mesenchymal stem cells in α-MEM, which contains also other factors revealed useful by present invention. The present invention revealed that use of both $Mg^{2+}$ and $Ca^{2+}$ ions preferably with supporting factors is especially useful for producing optimally viable cells. The preferred conditions further include conditions to prevent aggregation and surface binding of cells, especially preferred shear force conditions.

PCT/FI2008/050015, filed 18.1.2008, includes enzyme tagging technologies. The present invention provides specific forms and methods for the tagging, including glycan tagging with multiple tags and limited lysine-specific tagging by biotinylation.

It is realised that previously published cell modification conditions without divalent cations are not optimal for cell status. It was revealed that the condition induced morphological changes of cells, including non-natural granularity of the cells which are likely to reduce the viability of the cells, though the cells were indicated to be alive according to Sackstein et al.

The present invention is further directed to the use of strong protease conditions producing unicellular cell suspension. It is realized that this is needed to produce effective glycosylation and optimal unicellular product for subsequent in vivo use. It is realized that the cell population produced under the Sackstein conditions with a low amount of protease might not result in a unicellular preparation.

The process described by Sackstein and colleagues produces an N-glycan-linked sialyl Lewis x (sLex) epitope, but essentially no other selectin ligands structures (Sackstein et al. Nature Med 2008, 14(2):181-187). The present invention, including a reaction condition with divalent cations, effectively produced the sLex on O-glycan type structures different from the modification indicated by Sackstein.

The present invention further provides methods for specific tagging and washing cells with glycosyltransferase inhibitors to remove the enzymes from cell preparations after modification reactions.

Changes of sialylation by desialylation and resialylation with specific sialyltransferases has been reported for red cells in order to analyze binding specificities of influenza virus (Paulson, J. et al.).

Partial desialylation and alpha-6-resialylation of human peripheral blood and bone marrow CD34+ cells, both non-adherent blood cells, has been reported, the peripheral blood cells having been released by GM-CSF and most of the subjects being under cancer therapy (Schwarz-Albiez, Reihard et al., 2004, Glycoconj. J. 21:451-459). The large variations in results may be due to therapy and GM-CSF. The method used did not reveal quantitation of sialic acid types, due to a limited specificity of the sialyltransferase used. The modifications of sialic acid would likely further affect the acceptor specificity of the sialyltransferase used and thus the structures labelled. The present invention is especially directed to α3-sialylation of the specific carrier structures.

Removal of NeuGc from pig xenotransplant tissue and resialylation by NeuAc and sialyltransferase has been also suggested (WO 2002/088351). That work was not directed to stem cells, nor human stem cells directed methods, nor were the methods used specified, although this is essential for applications in these cells. The xenotransplantation idea is not relevant to present invention due to tissue and species specificity of glycosylation. A patent application (WO 2003/105908) describes possible sialidase and sialyltransferase reactions for certain NK or lymphocyte cell lines. The results revealed that the reactions varied between the cell lines and were not predictable under the conditions used in the work. Further, the reaction conditions of sialyltransferase without CMP-sialic acid were not described by the inventors.

Use of an inhibitor after glycomodification reaction has been indicated, but the chemical nature of the inhibitors was not indicated (WO 2004/072306). There is no indication of use of an inhibitor, especially soluble acceptor which mimics competitive inhibitor in context of cells and sialidase reactions or glycosyltransferase reactions. Furthermore, no useful concentration ranges for the substrates has been indicated and the present inventors were first to reveal the need of removal of bound glycosyltransferases from enzymes.

Xia et al. (2004) Blood 104 (10) 3091-9 describes changing fucosylation of cord blood cell population without changing sialylation levels and possible usefulness of the modification in targeting of the cells to the bone marrow.

DIFFERENCE TO PRIOR ART

Manganese ion is most common divalent cation activator of glycosyltransferase enzymes. Xia, L. et al (Blood 2004, 3091-96), Hidalgo A. et al (Blood 2005, 567-575) and others have applied the manganese method to hemtopoietic cells, which appears to be somewhat tolerable to the cells during short time. However, the detrimental effect to cells would partially reduce the usefulness of the cells. Furthermore the manganese cannot be removed totally from cell preparations and it is known to cause Parkinson's disease like disorders with very low concentrations. It can be thus concluded that the manganese methods create less viable or less functional cells, which contain harmful or toxic metal contamination, especially not desired for in vivo works.

The works of Sackstein (Nature Medicine 2008, 14(2): 181-187 and WO2007/143204) indicate that it is possible to fucosylate cells without presence of any divalent cations. The Sackstein refers to obvious toxicity of manganese. Interestingly Sackstein selects media devoid of also other divalent Mg2+ and Ca2+. This is likely because these cations cause adherence, especially adherence to surface and intracellular aggregation. The adherence blocks sterically the cells from glycomodification. The present inventors were able to prevent this by using methods preventing adherence of cells and still obtain effective glycomodification.

The present inventors revealed glycomodification by enzymes modifying N-acetyllactosamine sialylation (sialyltransferase and sialidase) and fucosyltransferases, especially α3- and/or α4-fucosyltransferase. It is realized that use of the specific enzyme types under the complex reaction composition is inventive. For example various divalent cations cause very enzyme specifically activation or actual inhibition conditions of the sialyltransferases and α3/4-fucosyltransferase vary a lot, and it would not have been easy to predict if the specific enzymes/enzyme types would have been active enough to produce effective cell fucosylation and sialylation modifications, especially in the presence of two different cations.

Different enzyme types such as α2- or α6-fucosyltransferases or ganglioseries ganglioside specific sialyltransferases are not predicting the ion requirement or concentrations useful for the preferred enzymes and in vitro oligosaccharide conditions are not useful for prediction cell surface reactions under complex conditions of the present invention.

The transferases are under complex regulation in cells including fosforylation and proteolysis may alter or destroy enzyme activities, the present invention moved from traditional buffer media depressing biological activities to complex biological culture media including cations and cofactors activating cellular enzymes and even chelating reagents among the vitamins, cofactors, and even nucleotides known to inhibit glycosyltransferases and amino acids. There are not useful models of predicting useful reaction (if any) under such complex biological (close to in vivo) conditions. In vivo the actual glycosyltransferase enzymes are known to act for glycosylation of cells only under concentrated intracellular Golgi membrane bound conditions, with specific cofactors and ions but not as soluble extracellular enzymes.

The inventors were further able to perform the cellular glycosylation in the presence of mammalian type glycosylated proteins. It is realized that glycosyltransferases (or glycosidases) can be inhibited or adhered with the relative large amount of glycosyltransferases. The enzymes are known to bind various glycans not even being their substrates or products (product inhibition). The invention reveled glycoproteins essentially devoid of glycan acceptors under the specific reaction conditions including specifically controlled and limited acceptor glycans. Most surprisingly the present invention reveals that it is possible to produce glycomodification conditions where the cells are modified in the presence of amount of glycoprotein comprising limited and controlled actual acceptor(substrate) glycans for the glycomodification enzymes. The limited and controlled glycan amount can comprise the substrate glycan in excess, even large excess to the cellular glycans and surprisingly the invention revealed that cells were effectively glycosylated. The presence of glycoproteins is of benefit for supporting cells (e.g. transferrin), stabilizing enzymes and further with effects preventing cell adherence.

The invention further revealed novel cell product with high glycomodification levels, extremely high viability and presence of normal morphology and absence of anomalous morphology of cells.

Novel Cell Products

The present invention further provides novel cell products with improved glycomodification levels. The invention reveled methods to produced extremely high amount of several sialyl-Lewis x epitopes of very high portion of cells, preferably in over 40%, more preferably over 60%, even more preferably over 70%, more preferably over 80%, more preferably over 90%, even more preferably over 95%, more preferably over 97%, and most preferably over 98% of the modified cells when analyzed with specific antibodies of present cells, in a preferred embodiment by CHO-131 directed to O-glycans like ones on P-selectin ligands (different from Sackstein's glycans).

The invention also reveled under sialylated cells which sialylation can be increased by present sialylation methods and observed by specific reagents of invention. The preferred increased proportion of cell surface sialylated cells, observable by the specific reagent of examples, includes increased proportion of at least 3%, more preferably at least 5%, even more preferably at least 7% and most preferably at least 10% of the cells and under specific embodiment 25% or more preferably 50% sialylation level increase of the available cellular acceptor sites.

It is realized that the present methods allowed surprisingly more efficient reaction by better enzyme activity and better reaction kinetics with novel cell handling conditions. It is further realized that the shear stress conditions applied remove cell and extracellular matrix residues from cell surfaces allowing more effective glycomodification. Furthermore the present divalent cation and cull culter media conditions allow recovery of cell surface proteins and glycans after the stress from possible transfer from cell culture conditions The present invention further revealed optimized methods for producing highly desilylated and viable stem cells by optimized sialidase reactions.

The invention is further directed to combined sialylation and fucosylation methods to allow production of increased amount, of sialyl-Lewis x structures, the present optimized cell handling methods allow thus production of the high sialyl-Lewis x expression on high proportion of cells without producing high amounts of Lewis x.

The novel cell products are further characterized by normal morphology homogenously on very high proportion of the cells and absence of anomalous morphology (e.g. ones produced with Sackstein methods) and at least 98%, more preferably 99%, and most preferably 100% viability not observable with the cells produced by method of Sackstein. It is realized that presence of anomalous or dead cells even in minor amount can cause severe immunological complications if cells are used in vivo.

The novel cell product does not contain substantial amounts of manganese, because this is not used in the buffers. It can be estimated that even after several cell washes manganese incubated cells contain significant amount of toxic manganese. In present cell preparation the manganese 2+ cation concentration is below 1 mM, more preferably below 100 microM, more preferably below 50 microM, even more preferably below 10 microM, even more preferably below 1 microM, even more preferably below 100 nanoM, even more preferably below 10 nanoM and even more preferably below 1 nanoM and most preferably below 10 picoM.

Adherence

The present invention reveals that it is possible to prevent adherence of cells in presence of non-toxic divalent cations in a cell culture medium and that this allows effective glycomodification of cells. The invention showed prevention of adherence in form of adherence to surface and intracellular aggregation.

It is realized that the methods can be applied to any adherent cells such as $Ca^{2+}$ and/or $Mg^{2+}$ activatable adherence receptor containing cells including integrin and C-type (calcium activated) lectin, in preferred embodiment selectin such as E-, P, or L-selectin, containing cells. Preferably such cells includes epithelial, endothelial cell, cell growing as adherent layers in cell culture, hematopoietic cells, leukocytes, especially ones containing integrins, C-type lectins or selectins, Glycomodification Reactions by Glycomodification Enzymes Including Glycosidases and Glycosyltransferases The present invention is directed to glycomodification reactions by glycosyltransferase enzymes referring herein to i) preferred actual glycosyltransferase enzymes transferring monosaccharide residues from nucleotide sugars to acceptors [more specifically acceptor site(s) in acceptor glycans] and ii) separately preferred transglycosylating enzymes which can transglycosylase monosaccharide residues from non-nucleotide sugar glycoconjugates such as from oligosaccharides, or monosaccharide conjugates such as paranitrophenyl conjugates, or even free monosaccharides iii) other glycan substituting enzymes, transferring a non-monosaccharide substituent on to a glycan such as sulphate residue transferred by a sulphotransferase.

The present invention provides novel conditions glycomodification of cells especially glycomodification of N-linked and O-linked glycans and optionally further N-acetyllactosamine (Galβ3/4GlcNAc)-epitopes of glycolipids. The N-acetyllactosamine epitopes may be suitably sialylated for a fucosylation reaction for synthesis of sialylated and fucosylated epitopes (α3-sialylated to Gal, or α6-sialylated to GlcNAc on type 1 N-acetyllactosamines) or sialylated for desialylation, and the present invention further reveals sialyation of α3/4-fucosylated N-acetyllactosemines. The preferred glycomodification is sialylation, desialylation, and/or fucosylation of the N-acetyllactosamine epitopes. The preferred sialylation is α3-sialylation of terminal Gal and/or α6-sialylation (terminal Gal or the GlcNAc of N-acetyllactosamine of cells, and fucosylation is α3- and/or α4-fucosylation of GlcNAc residues of N-acetyllactosamine structures.

$1.75 \times 10^6$ cells were resuspended in either 300 μl Minimum Essential Medium (MEM) a medium supplemented with 0.5% HSA or $Ca^{2+}/Mg^{2+}$-free Hanks' Balanced Salt Solution (HBSS) supplemented with 0.1% HSA. The BM-MSC suspensions were incubated in 24-well cell culture vessels for 2 hours in +37° C. cell incubator. A part of the reactions were resuspended by mechanical pipetting every 20 minutes during the incubation. Representative phase contrast microscope pictures of cells in suspension were taken at the beginning of the experiment and after 1 h and 2 h. Representative phase contrast microscope pictures of each well have been taken with 10× objective of only the cells in suspension. Panels A. and B. are enlarged representative areas of 2 h situation where cells have been resuspended every 20 minutes. Arrows indicate representative cells with different morphology. Cells in α-MEM+0.5% HSA adhere easily to small cell clusters if not resuspended at all during 2 h incubation (encircled).

Figure 3:
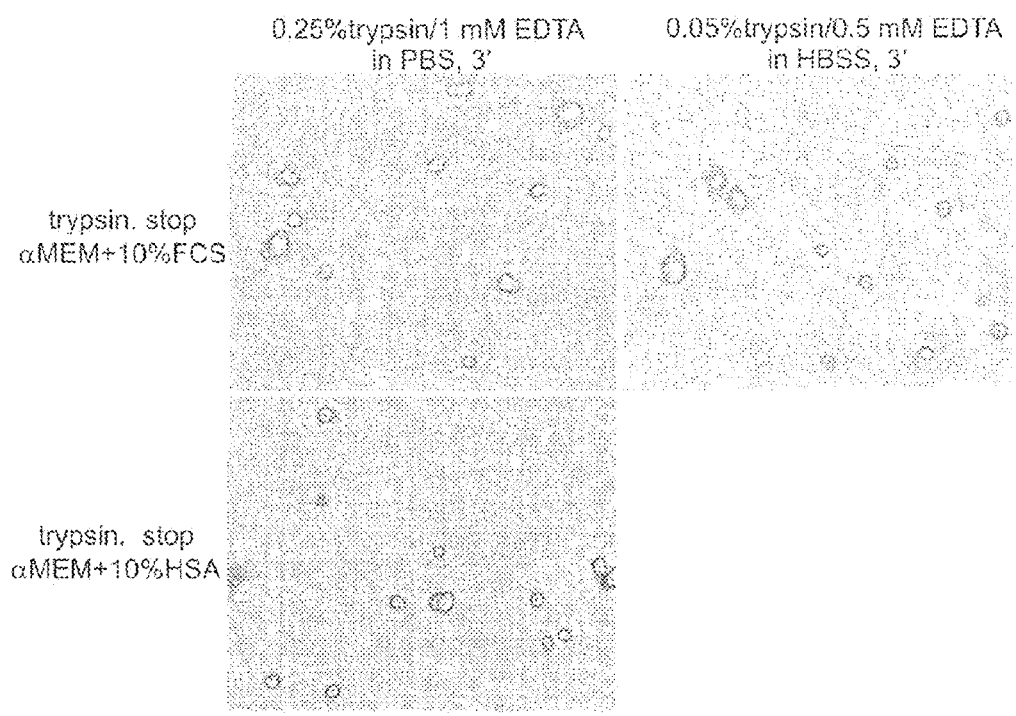

FIG. 3. Trypsinization inhibition (trypsin. stop) after 3 min by adding either excess α-MEM+10% fetal calf serum (FCS) or α-MEM+10% human serum albumin (HSA). Representative phase contrast microscope pictures of BM-MSC whose trypsinizations were inhibited by either FCS (top) or HSA (below). The cells were detached with either 0.25% or 0.05% trypsin. Both trypsinization methods produced equally viable unicellular cell suspensions and trypsinization could be as effectively stopped with HSA as with FCS. Hence, xenoantigen-free inhibition could be done.

Figure 4:
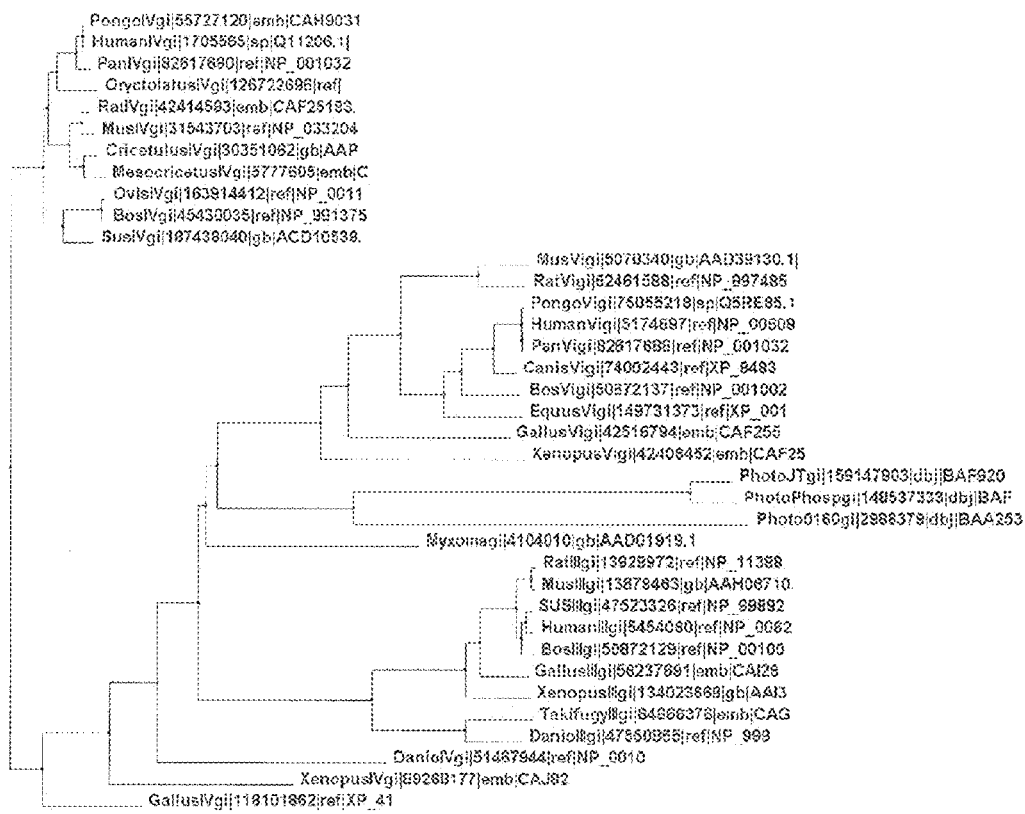

FIG. 4. Phylogenetic tree of sialyltransferases.

Figure 5:
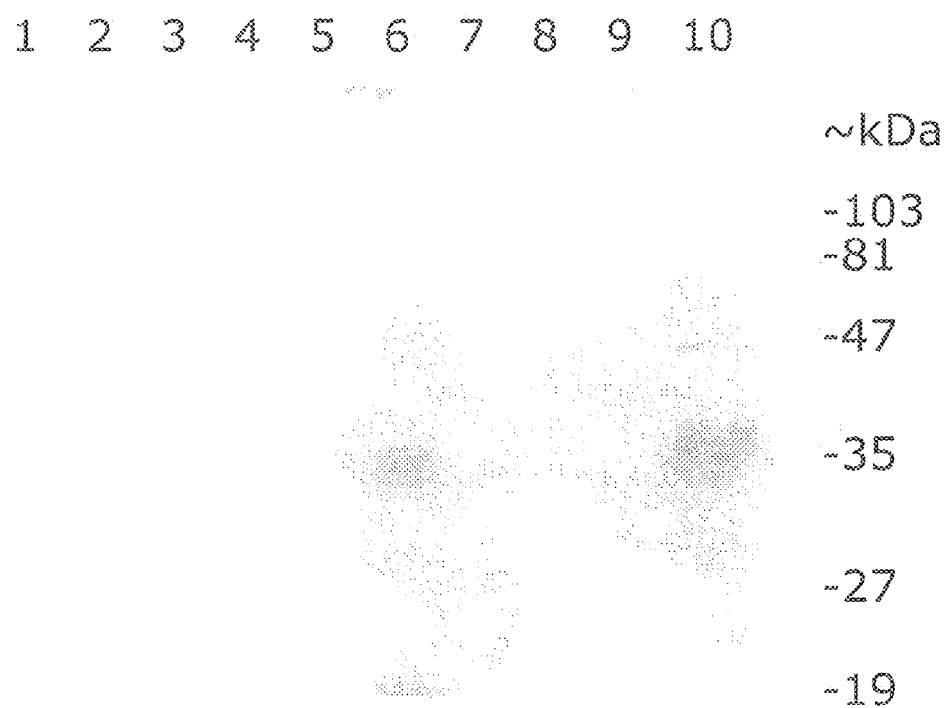

FIG. 5. Removal of biotin-conjugated α2,3-N-sialyltransferase (SAT) from solution by streptavidin-coated magnetic particles, visualized by SDS-PAGE and streptavidin-blotting.

Lanes 1-5, SAT without biotinylation; Lanes 6-9, biotin-conjugated SAT. Lanes 1 and 6, magnetic particles with precipitated SAT; Lanes 2-3 and 7-8, supernatant after the precipitation; Lanes 4 and 9, supernatant of the subsequent wash step; Lanes 5 and 10, SAT control (biotin-conjugated SAT visible at the expected 39 kDa).

Figure 6:
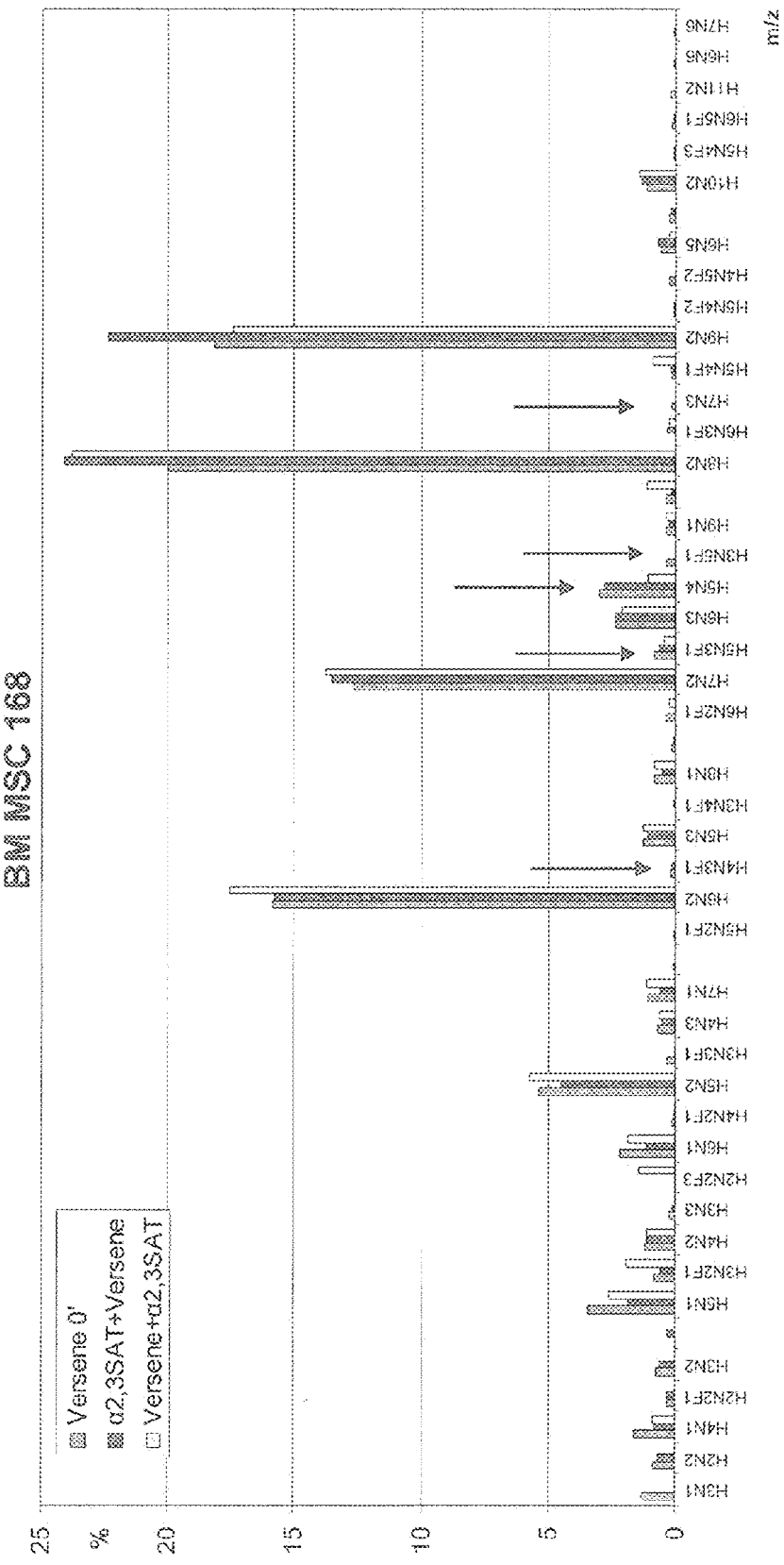

FIG. 6. Neutral N-glycan profile of bone-marrow derived mesenchymal stem cells (BM-MSC) enzymatically modified with α2,3-N-Sialyltransferase either when adherent with subsequent EDTA (Versene) detachment or in suspension after EDTA (Versene) detachment. Indicative terminal N-acetyllactosamine (LN) units for successful sialylation are marked with red arrows.

Figure 7:
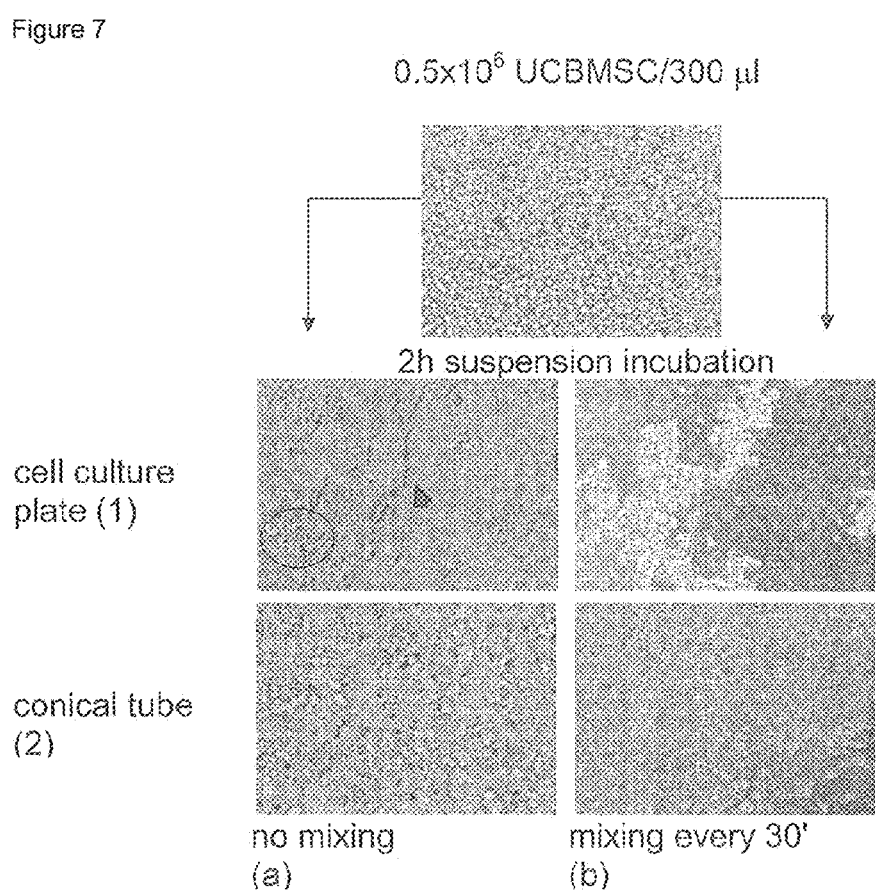

FIG. 7. UCBMSC 391P (p4) in enforced suspension in cell culture plate well (1) or conical tube (2). 0.5×10e6 cells were used/300 μl reaction buffer for 2 hours. Upper picture shows MSCs in suspension at time point 0. Left: No mechanical mixing (a) during 2 hour incubation aggregates cells (encircled) and cells attach to plastic. Right: Mixing the cells every 30 min (b) by pipetting significantly inhibits aggregation and cell attachment. Cells are better maintained in one-cell suspensions when kept in suspension in conical tubes (2 b).

Figure 8A:
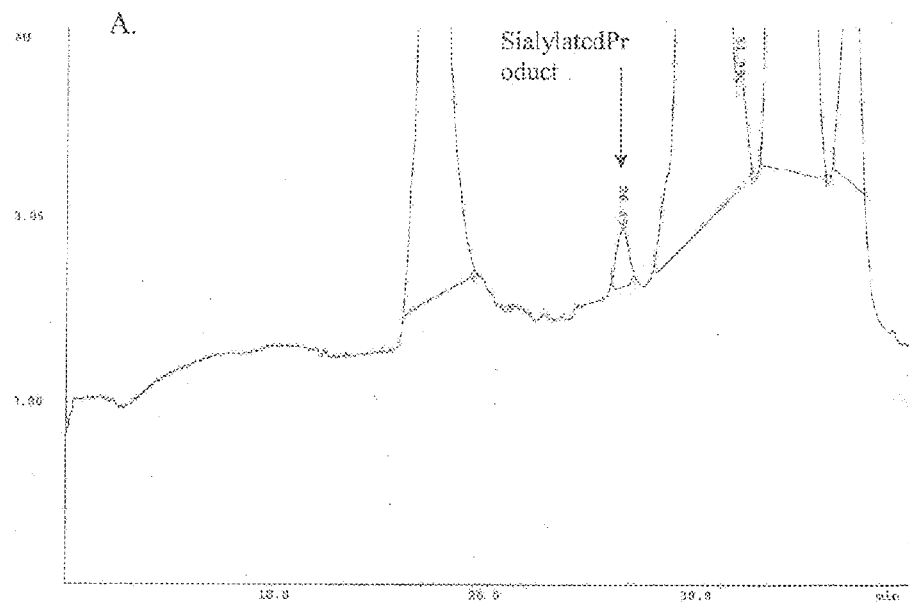
Figure 8B:
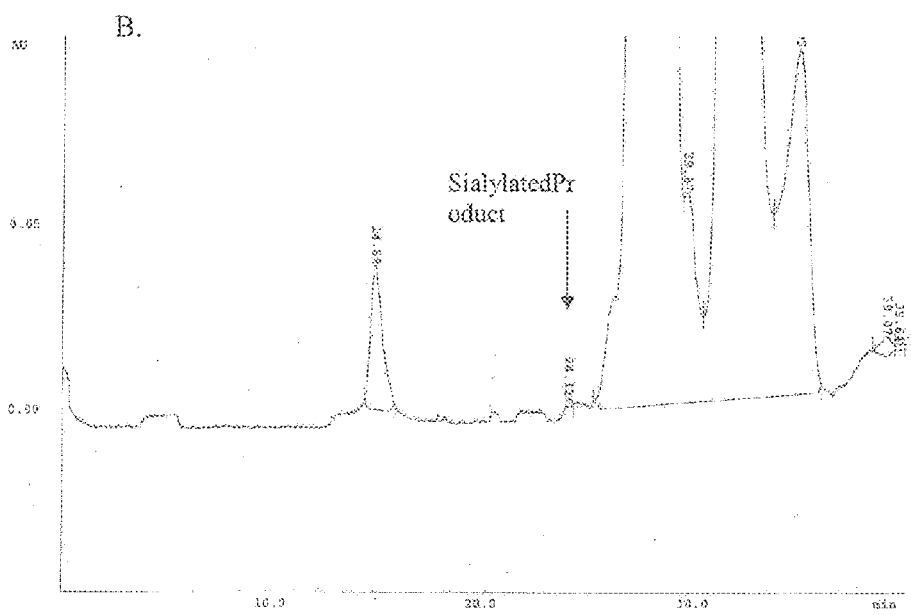

FIG. 8. Activity of α2,3SAT in a-MEM with (A) or without (B) human serum albumin. Aliquots of reaction mixtures from overnight reaction were analyzed by size-exclusion chromatography. Reaction product was formed only in presence of albumin.

Figure 9:
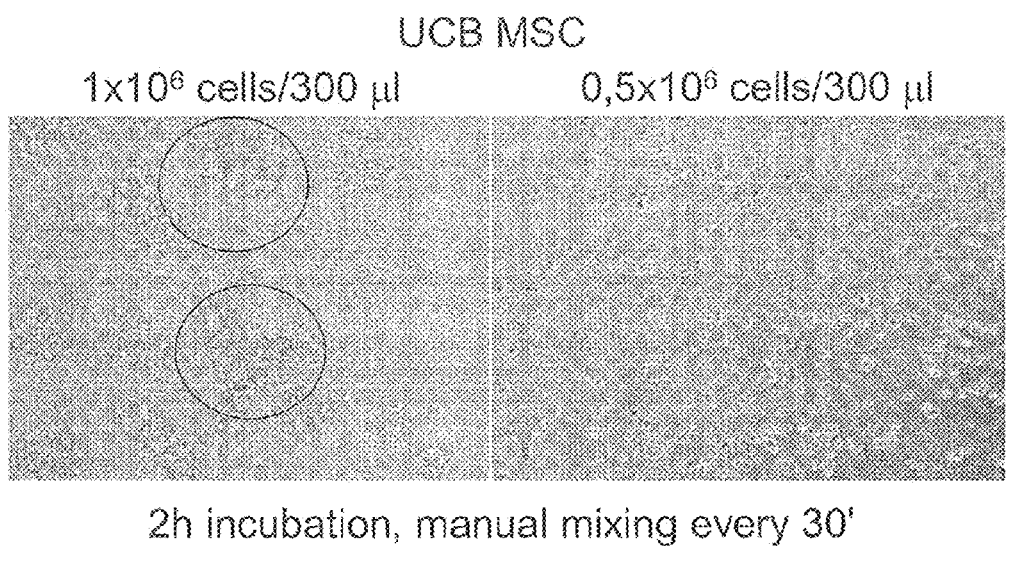

FIG. 9. Suspension incubated human umbilical cord blood-derived mesenchymal stem cells (UCBMSC) in two different cell densities. The cells were incubated in αMEM+0.5% human serum albumin (HSA) for 2 hours with resuspension applied every 30 min. Encircled areas indicate evident large cell aggregates.

Figures 10A, 10B:
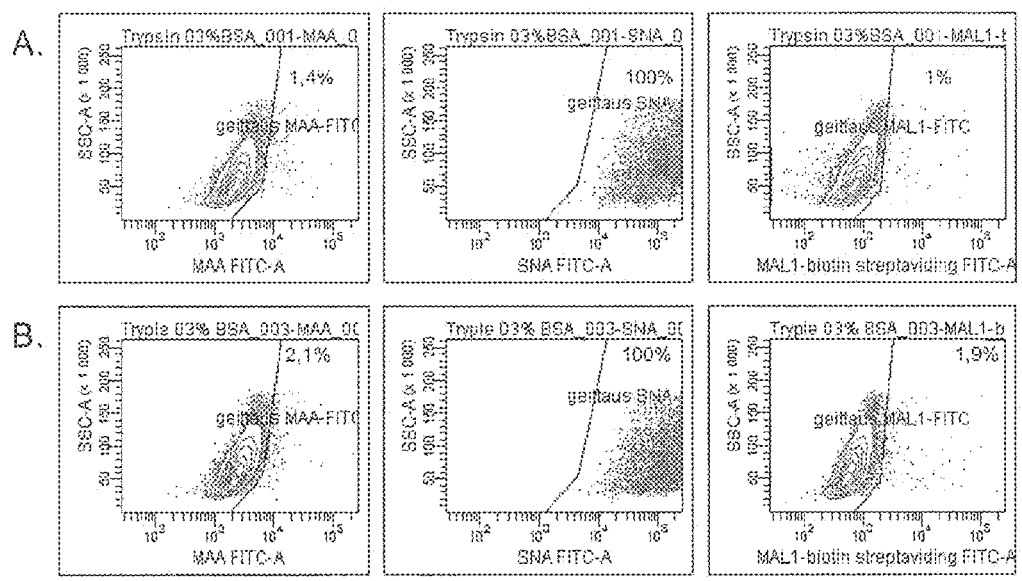

FIG. 10. Human umbilical cord blood-derived mesenchymal stem cell (UCBMSC) cell surface α2,3- and α2,6-sialylation levels of freshly detached cells after A) porcine trypsin-0.25% EDTA-based detachment or B) TrypLE Express detachment of the cells. Cell surface α2,3- and α2,6-sialylation studied by labeling cells with the conjugated plant lectins MAA, SNA and MAL-1 and flow cytometry analysis. Percentage of gated positive cells indicated in upper right corner.

FIG. 11. Desialylation of 0.5×10e6 UCBMSCs using 200 mU *Vibrio cholerae* sialidase. MAA, SNA, MAL1 and CHO131 labeling of cells: A) 2 h incubation control with reaction buffer αMEM Glutamax+0.5% HSA and no enzyme B) 2 h desialylation with 200 mU *Vibrio cholerae* sialidase in αMEM Glutamax+0.5% HSA, C) 2 h incubation control with reaction buffer αMEM Glutamax+0.5% BSA and no enzyme D) 2 h desialylation with 200 mU *Vibrio cholerae* sialidase in αMEM Glutamax+0.5% BSA. Percentage positive gated cells indicated in upper right corner. Results are presented as flow cytometry scatters analyzed with FACSDiva software.

FIG. 12. Acute (1 h) and subacute (12 h) in vivo biodistribution of Tc99-HMPAO-(A,B) and [$^3$H]-2DG (C)-labeled human bone-marrow derived mesenchymal stem cells (BMMSC) with and without enforced enzymatic cell surface α1,3-fucosylation with FUTVI. The animals received 0.5× $10^6$/mice (A,B) or 1×$10^6$/mice (C) injected into the tail vena. The radioactivity of whole lungs and the outflow of one femur was counted. Control indicates animals receiving reaction buffer incubated cells without enzyme and FUTVI indicates animals receiving equal amounts of a1,3-fucosylated cells. The results are presented either as means±SD or +SEM.

FIG. 13. Cells in 80% confluency after indicated glycomodifications in culture media based reaction buffer supplemented with 0.5% human serum albumin (HSA). All cells were plated after the glycomodification with 1000 cell per cm$^2$. Both untreated cells and reaction buffer only incubated cells served as controls. No differences were seen in growth behavior or morphology as compared to control cells.

Figure 14:
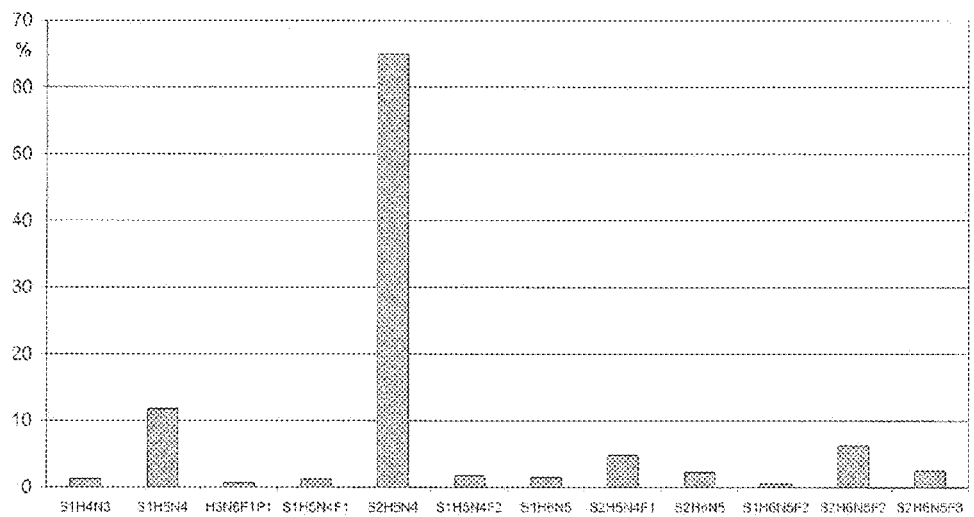

FIG. 14. Acidic N-glycans of StemPro MSC SFM XF, 100× Supplement.

DESCRIPTION OF THE INVENTION

The invention provides a novel method or kit for modification of glycosylation of cells such as human stem cells. The invention revealed that it is possible to modify glycosylation of cells, when the modification is performed in presence of culture medium (i.e. growth medium) reagents such as divalent cations $Mg^{2+}$ and/or $Ca^{2+}$. The invention is especially directed to glycosyltransferase modifications by sialyl- and fucosyltransferases. Furthermore, the invention revealed specific reagents for removal of the modification enzymes from reaction mixtures including site specific tags of enzymes and specific substrate inhibitors.

The invention is directed to a novel cell population and to a method for its production. The cell population is derived from human stem cells and the cell population comprises in vitro enzymatically modified glycosylation produced by a method comprising enzymatic in vitro glycan modification in the presence of divalent cations $Mg^{2+}$ and $Ca^{2+}$ and adherence of the cells is inhibited by shear force. Optionally the modification enzyme is removed from the cell preparation by using at least one reagent selected from the group a glycan linked tag, not essentially reducing the enzymatic activity of the protein;

a protein specifically linked tag, not essentially reducing the enzymatic activity of the enzyme protein;

a specific substrate inhibitor binding effective to the active site of the enzyme and releasing the enzyme from the cells, preferably being acceptor substrate analog of glycosyltransferase or substrate analog for protease.

The novel cells are preferably prepared or derived from cord blood or bone marrow derived mesenchymal stem cells or other mesenchymal stem cells. In a preferred embodiment the cells are prepared or derived from isolated cord blood cells and in another embodiment from bone marrow derived cells. The invention is specifically directed to adherent cells. It is realized that several modifications can change also other cell types adherent. In a specific embodiment the invention is directed to modification of stem cells by the methods according to the present invention, when the adhesion of the cells is increased.

The novel cell population is preferably produced by a method, wherein the cells are modified in the presence of $Mg^{2+}$. It was realized that $Mg^{2+}$ would support the glycosylation reactions. In another preferred embodiment the novel cell population is preferably produced by method, wherein the cells are modified in the presence of $Ca^{2+}$. The invention revealed that presence of $Ca^{2+}$ is useful for maintaining the cell morphology. Even more preferably the cells are modified in the presence of both $Ca^{2+}$ and $Mg^{2+}$.

The invention is further directed to cell population and its production, wherein the cells are modified in the presence of additional supporting factors required for cell cultivation selected from the group consisting of vitamins, energy and structural nutrients, and physiological salt, i.e. in culture medium such as α-MEM (see Table 12).

In another preferred embodiment the novel cells are modified in the presence of non-glycoprotein.

In another preferred embodiment the cells are modified in the presence of at least one cell supporting materials, preferably all additional supporting factors selected from the group consisting of 1) $Ca^{2+}$ and $Mg^{2+}$;
2) Supporting factors
2.1) vitamins,
2.2) energy and structural nutrients such as amino acids, and
2.3) physiological salt;
3) non-glycoprotein.

The invention is specially directed to the combination of the factors, which is especially useful for maintaining the cells during the modification reactions.

In a preferred embodiment both $Mg^{2+}$ and $Ca^{2+}$ ions are used in a concentration of at least 0.05 mM, even more preferably 0.5 mM and most preferably at least 1 mM and less than 10 mM. The preferred concentrations of the non-toxic divalent cations are close to physiological concentration, preferably between about 0.5 mM and 1.0 mM, more preferably about 0.8 mM for $Ca^{2+}$, and preferred $Mg^{2+}$ concentration is between about 1.5 and 2 mM, more preferably about 1.8 mM. More preferably the ions and optionally additional ions are used in concentrations similar to those in the α-MEM medium, also referred to as the minimal essential medium (Nature 1971, Catalog of Gibco/Invitrogen®).

Accordingly, the kit of the present invention comprises culture medium for cell cultures as defined above and glycosyltransferase or glycosidase. The kit may further include albumin, such as human albumin, or transferrin as a non-glycoprotein or the culture medium may also contain said non-glycoprotein as a supplement.

The preferred cell modification kits contain cell culture medium (or its concentrate), enzyme and preferably also possible cofactors of enzyme such as nucleotide sugar or other donor substrates for the glycomodification enzyme. In a preferred embodiment the enzyme, medium and nucleotides are in separate containers, in another preferred embodiment the glycomodification enzyme is included in the container of the medium and the cofactor is in the separate container. In one preferred kit, all components are in the same container in solid form. The preferred kit further includes instructions for performing reaction with the required components for suitable time and optionally instructions and/device for mixing or suspending the cells.

Detaching Adherent Stem Cells by Protease Treatment

The invention is especially directed to novel cell populations produced according to the invention, wherein the cells are adherent cells detached from cell culture surface by protease treatment. The cells are preferably detached under condition producing unicellular cell suspension.

The preferred trypsin condition includes trypsin concentrations from about 0.01 mg/ml to about 0.5 mg/ml, wherein 1 mg corresponds to about 10 000 BAEE units of trypsin, as defined by the producer of the trypsin (Invitrogen). The trypsin is preferably from bovine (product number 25200, Invitrogen). The reaction is preferably short, i.e. from about 0.5 min to about 5 min, more preferably about 3 min.

In a preferred embodiment the cell population is produced from strongly adherent cells and protease is trypsin which is used in a condition equivalent of trypsin concentration of 0.075 mg/ml, more preferably 1 mg/ml, most preferably 0.25 mg/ml for about three minutes.

Cells Produced by Optimal Proteolytic Reaction.

The invention is especially directed to mesenchymal cells, which are released from adherent cell culture by a protease, preferably trypsin under optimal conditions (Example 3).

Production of Unicellular Cell Preparation.

The invention is directed to the release of adherent mesenchymal stem cells from cell culture support under proteolysis condition producing unicellular cell preparation. The invention further revealed that the unicellular cell suspension is effectively modified in glycomodification reactions (Examples 2 and 3).

As a control experiment, adherent cells which are not in unicellular forms are not effectively modified by glycosyltransferases (Example 9).

Use of Protease Inhibitors

The invention revealed that it is useful to end the protease reaction by inhibitor molecules. In a preferred embodiment the protease reaction is ended by adding an inhibitor of protease, preferably substrate inhibitor which releases the protease from the cell surface (Example 3).

The invention is further directed to the novel cells and their production method, wherein the protease is effectively removed from cell surface of the modified cells, preferably using a covalent tag attached to the protease and/or a substrate inhibitor of the protease, which is optionally tagged.

The protease enzyme and/or its substrate inhibitor are preferably tagged by at least one covalent tagging method selected from the group consisting of protein amine tagging, glycan tagging,
N-terminal tagging of protein or peptide and
C-terminal tagging of protein or peptide.

The invention is further directed to a method for removal of the protease and/or protease inhibitor, wherein the protease and/or substrate inhibitor of the protease is tagged and the inhibitor and protease are effectively removed from the surface of the modified cells by using an adsorbent binding the tag (Example 5).

In a preferred embodiment the protease is tagged and high-affinity inhibitor peptide or protein is used.

Glycomodification of Cells in Presence of Non-Toxic Divalent Cations and Other Supporting Factors The invention revealed that it is possible to modify adherent cells, preferably adherent stem cells and most preferably mesenchymal stem cells in presence of divalent cations, when the divalent cation is non-toxic. The non-toxic divalent cation is preferably not toxic as high micromolar or millimomolar concentration. An example of a toxic divalent cation is $Mn^{2+}$ cation. The present method is in the contrast to the method of Sackstein wherein all divalent cations were omitted.

In a preferred embodiment the preferred non-glycoproteins of present invention do not include cytokines according to WO 2008/011094.

The present invention reveals that in the presence of specific divalent cations mesenchymal cells are more viable and can be effectively glycosylated by glycosyltransferases, especially by sialyltransferases and fucosyltransferases.

It was realized that the reaction media lacking divalent cations is not optimal for mesenchymal stem cells. Though the cells appear viable their ability to recover from the stress due to proteolytic treatment is reduced and the cells tend to adhere to aggregates which reduce both their viability and their glycans accessibility to be modified. The invention revealed that aggregation and surface attachment occurs in the presence of non-toxic divalent cations. However, as shown in Example 2, it is possible to recover the adherent mesenchymal stem cells. The presence of the divalent cations provided 100% viability. This is a clear benefit as the dead cells may cause undesired immunological and other reactions in therapeutic use. Furthermore it was revealed that resuspension of the cells prevented aggregation and surface adhesion, hence, leading to a clearly increased yield of the cells (Example 2).

The conditions in the Sackstein-process without divalent cations can be regarded as non optimal to the activity for many fucosyltransferases and sialyltransferases. The presence of divalent cations is especially preferred for fucosyltransferase reactions. Presence of divalent cations is especially preferred for fucosyltransferases FUC-TIII-VII, more preferably for Fuc-TVI and Fuc-TVII. Sialyltransferases are also known to function optimally with divalent cations.

In a preferred embodiment both $Mg^{2+}$ and $Ca^{2+}$ ions are used with at least 0.05 mM, more preferably at least 0.1 mM, even more preferably 0.5 mM and most preferably at least 1 mM and less than 10 mM. More preferably the ions are use as physiological concentrations, preferably similar as in α-MEM.

Mesenchymal Stem Cells in Suspension.

The invention revealed that the novel cells produced by the present invention are maintained in mononuclear cell-like morphology while the conditions without non-toxic divalent cations caused granularity of the cells. The invention is especially directed to the novel cell population, wherein the cells in suspension are essentially mononuclear cell-like cells without granularity (Example 2).

Glycomodification of Cells in Presence of Non-Glycoprotein and Supporting Factors: Non-glycoprotein The invention is directed to glycomodification of adherent cells, more preferably mesenchymal stem cells, in the presence of non-glycoproteins including non-glycosylated or non-glycosylable protein. The non-glycoprotein is a protein, which does not contain substantial amount of acceptor glycans for modification enzymes, such as terminal Gal, lactosamine(s), GalNAc, or subterminal GlcNAc. The acceptor glycan means a substrate for glycosyltransferases according to the present invention, preferably α3- and/or α6-sialyltransferase acceptor sites and substrates for glycosidases such as sialidase enzymes such as α3- and/or α6-sialylglycans.

Preferred non-glycoproteins are protein capable of supporting cell culture without preventing or substantially not preventing the glycomodification reactions of the invention. In a preferred embodiment the non-glycoprotein increases the effect of glycosyltransferase reaction. This is surprising because the proteins do not have obvious interactions. The invention showed that albumin support glycosyltransferase reactions to cells and that human albumin preparations have higher such activity when compared to bovine serum albumin. The preferred non-glycoproteins include preferably human non-glycoproteins, more preferably human serum proteins, preferably non-glycoprotein forms of albumin and/or transferrin, most preferably human albumin and human transferrin or derivatives or fragments, preferably functional fragments thereof.

Human serum proteins are for instance (see Quality assurance and reproducibility Am. J. Clin. Path. 97: 97, 1992): 1) transthyretin ("retinol binding protein"; "prealbumin"); 2) albumin; 3) α-1 globulins, such as α-1 protease inhibitor (α-1 antitrypsin), α-1 glycoprotein (orosomucoid), α-fetoprotein and high density lipoprotein (HDL); 4) α-2 globulins, such as α-2 macroglobulin, antithrombin III, ceruloplasmin, and haptoglobin; 5) beta globulins, such as beta and pre-beta lipoproteins (LDL and VLDL), C3, C-reactive protein, haemoglobin, plasminogen, and transferrin ("principal component of the beta1 subdivision"); 6) gamma globulins.

There are also additional human serum proteins and at least 325 distinct proteins have been identified (Pieper et al. 2003, Proteomics 2003, 3:1345-1364).

The preferred non-glycoproteins include non-glycosylated proteins such as serum albumin, which does not contain glycosylations sites, in a preferred embodiment bovine serum albumin and non-glycosylated isoforms of human serum albumin or essentially non-glycoprotein form of human albumin. The bovine albumin is preferably highly pure and essentially a non-glycoprotein devoid of substantial amount of acceptor glycan contamination.

In a preferred embodiment the non-glycosylated human serum albumin is purified from a blood-derived human serum albumin by affinity chromatography by a reagent binding to the glycans of glycosylated isoform of human serum albumin. In another embodiment the residual glycosylation is removed by a chemical or enzymatic method. In yet another preferred embodiment the albumin is recombinant albumin produced in prokaryotic or eukaryotic cell producing no or not substantial amount of acceptor/substrate glycans for the glycosyltransferases. An example of recombinant albumin is a yeast-produced albumin (Delta/Novozyme, Australia/Denmark).

Preferred non-glycoproteins further include transferrin proteins not containing acceptor glycans or not containing substantial amount of acceptor glycans. A preferred transferrin is a recombinant transferrin or functional fragment thereof comprising low amount of sialyl- and/or fucosyltransferase acceptor sites, such as a recombinant transferrin lacking glycosylsite(s), more preferably recombinant human transferrin lacking N-glycosylation site(s) or a recombinant transferrin produced in organism producing no N-glycans (e.g. *E. coli*) or producing not complex type N-glycans (e.g. yeast *S. cerevisiae* or fungi such as *Aspergillus*). In a preferred embodiment the transferrin is highly sialylated transferrin, especially for use as substrate of sialyltransferase, and/or highly α6-sialylated transferrin for use as non-glycoprotein substrate of α3-fucosyltransferase. Preferred sources for sialylated transferrins include isolation from serum such as human serum and eukaryotic expression and optionally in vitro sialylation.

The non-glycoprotein protein may be used in concentration of 0.001-5% (weight/vol), preferably 0.01-2%, more preferably 0.01-1%, more preferably 0.05-0.5%, and in a preferred embodiment with concentration of about 0.1%. The molecular weight of the non-glycoprotein is preferably between 10-1000 kDa, more preferably 50-300 kDa. The very small molecular weight proteins with some glycosylation acceptor sites are used as lover w/v concentrations (e.g. 0.001-1%, more preferably 0.05-0.5% to avoid larger glycan concentrations and reduction of glycomodification speed)

It is realized that the protein to be used may contain some glycosylation sites due to practical production reasons. The invention reveals that such proteins are useful for the glycomodification according to the invention, when containing some acceptor sites for sialyl or fucosyltransferases such as less than an upper limit of 50 mol % of the protein amount, more preferably less than 35%, even more preferably less than 30%, even more preferably less than 25%, even more preferably less than 20%, even more preferably less than 15%, even more preferably less than 10%, most preferably less than 5%. Because of practical reasons the amount of acceptor sites could possibly not be limited below about 0.01%, more preferably above 0.1% even more preferably above 1%. The practical acceptor site levels are thus range being from, e.g., 0.01-50 mol %, 0.01-35% or 0.01-5 mol % (the lower limits are combinable any upper limit above), of the acceptor sites or in more preferred practical range about 0.1-50 mol %, 0.1-35% or 0.1-5 mol % or 1-50 mol %, 1-35% or 1-5 mol %.

The preferred non-glycoproteins being not substrates for sialylation experiment of the present invention includes proteins which are sialylated to high level. When the protein contains high sialic acid level, it cannot be further sialylated. A preferred highly sialylated N-glycoprotein contains at least same amount of monosialylated and disialylated N-glycans, more preferably at least 2 fold more disialylated biantennary N-glycans than monosialylated biantennary glycans, more preferably 3 fold, even more preferably 4 fold more, even more preferably 5 fold and most preferably. The amount of non-sialylated (neutral) complex type with terminal N-acetyllactosamine acceptor for the sialyltransferase, e.g. type II N-acetyllactosamine, is less than 30 mol % less than 20 mol % of the total N-glycans, more preferably less than 10%, even more preferably less than 5%, even more preferably less than 3%, most preferably less than 1%.

A preferred sialylated transferrin, preferably α6-sialylated human transferrin contains practically no neutral N-glycans, less than 5%, even more preferably less than 3%, most preferably less than 1% and the amount of disialylated biantennary N-glycans is at least 4 fold more, more preferably at least 5 fold, even more preferably 6 fold more than monosialylated biantennary glycans.

Example 19 shows a cell culture medium protein, such as human serum transferrin, containing high amounts diasialylated biantennary N-glycans corresponding to monosaccharide compositions S2H5N4 and S2H5N4F (S is Neu5Ac, H corresponds to 2 Gal and 3 Man residues and N is GlcNAc of complex type N-glycan), being much more abundant than corresponding monosialylated glycans S1H5N4, and S1H5N4F1.

Limited and Controlled Amount of Glycan Acceptor

The invention reveled glycoproteins essentially devoid of glycan acceptors or glycosylatable acceptors under the specific reaction conditions, these includes specifically controlled and limited acceptor glycans. Most surprisingly the present invention reveals that it is possible to produce glycomodification conditions where the cells are modified in the presence of amount of glycoprotein comprising limited and controlled actual acceptor(substrate) glycans for the glycomodification enzymes. The limited and controlled glycan amount can comprise the substrate glycan in excess, even large excess to the cellular glycans and surprisingly the invention revealed that cells were effectively glycosylated.

The preferred controlled and limited acceptor glycan is controlled with regard to glycan valency and or acceptor site valency on the glycans, preferably there is 1-5 glycans (not all glycosylation sites are necessarily used for every protein) maximum 5 glycans per protein, more preferably 1-4 glycans, more preferably 1-3 glycans and most preferably 1 or 2 glycans, and in specific embodiment only 1 glycans, preferably the glycans are modified not to be substrates of the specific glycmodification so the glycosylation site valency is above 0.05 or 0.1 of the all glycosylation sites of the glycans but on average less than 2, more preferably about 1 or less, more preferably less than 0.3 (30%), more preferably less than 0.2 (20%), and most preferably less than 0.1 (10%) (or other preferred valences described by the invention). In a preferred embodiment the amount of at least two acceptor site containing glycans (such as neutral biantenanry N-glycans for sialylation of fucosylation) is very low, preferably below 20%, 10%, 5%, 3% or 1% with increasing preference.

In preferred embodiment the glycosylation modification is preformed to cell materials on which the specific product glycan is present in low proportion of the cells in the beginning of the reaction (e.g. 0-50%, more preferably 1-35%, or under specific embodiment 1-10%) but the acceptor glycan is present in substantial part of the cells.

It is realized that the high concentration of the acceptor glycans on cell surface support the reactions.

An example of relatively large amount of limited and controlled acceptor glycans is a medium comprising a highly sialylated transferrin with concentration at least 0.01-0.1 mg/ml (similar to Example 19) for modification of a million cells in 0.5-1 ml of reaction volume. There can be 100-pmol-1 nmol acceptor glycan concentration in glycoprotein in comparison to low picomal glycan (e.g. 1-10 pmol) content of the cells. The unusual reaction kinetics of present reactions on cell surface allows unusually effective reactions under these conditions. The acceptor sites are limited essentially to one site per glycan (neutral biantennry glycan amount is low), and the valency of transferrin glycans is maximally two, the amount of proteins with two acceptor sites per protein on different glycans is very low (possibly 2-3%).

It is realized that it is highly suprising that the cell surface glycosylation can be performed in the presence of large proportional amount of glycan acceptor sites in comparison to the acceptor sites on the cells, in a preferred embodiment the cells are modified in the presence on non-glycoprotein with controlled and limited glycosylation with at least 0.1 to about at least 1000 fold amount of acceptor sites in comparison to acceptor sites on cells, in another embodiment the amount of sites is 1 to at least 100 fold, and in another embodiments at least 2 fold, 5 fold or 10 fold.

It is realized that due to cell specificity of the reaction the donor nucleotide can be adjusted to low levels, this reduces costs and amount of residual chemical in the cell preparation aimed for biological use or it vitro studies. In another preferred embodiment the amount of nucleotide sugar donor is adjusted level 2 times of the total acceptor site in the reaction), or 1.5 times the total acceptor sites, or 1.1 times the total acceptor sites and 1× of the total acceptor site, or even 0.9, 0.8, 0.75 or 0.5 times of the acceptor sites. (total acceptor sites includes glycoprotein and cellular acceptor sites and possible hydrolytic activity degrading the nucleotide sugar during the reaction).

The presence of glycoproteins is of benefit for supporting cells (e.g. transferrin), stabilizing enzymes and further with effects preventing cell adherence.

Equivalent Ion Conditions with Single Cation of Invention

It is realized that skilled person may optimize Mg2+ or Ca2+ concentration to allow use of only one of the cations and obtain similar or almost similar glycomodification and in another embodiment optionally including additional divalent cation under non-toxic or harmful concentration. Such conditions within the preferred or suitable to cells concentration ranges are within the scope of the present invention Glycomodification of Cells in the Presence of Metabolic Supporting Factors The invention revealed that it is possible to perform enzymatic glycomodification in the presence of "supporting factors", meaning here, for example, (i) vitamins, including enzyme cofactors, (ii) nutrients with energy functions, or (iii) nutrients with structural functions, all preferably in concentrations similar to those in the α-MEM medium.

In a preferred embodiment the reaction is performed in the presence of metabolic factors as present in a serum-free cell culture medium. In a preferred embodiment the cell culture medium is α-MEM for human mesenchymal stem cells. The medium contains only non-glycoproteins according to the invention and no other acceptor glycans or oligosaccharides, which would affect the activity of the modification enzymes.

Prevention of Adherence of Novel Cells

The present cells are adherent cells and modified in a condition preventing adhesion of the cells, especially their clustering and surface adherence. Preferably conditions are shear force involving conditions. It is further realized that the prevention of clustering may be obtained by various chemical factors.

In a preferred embodiment the shear force to the cells is provided by tubing or tubing with a changing flow velocity that detaches the cells, or by tubing comprising a narrowing that provides turning flow direction and a swirl or swirls that detach cells from each other, or by applying a flow of liquid with swirls on cells. The administration of the shear force preferably includes providing a certain flow accelerating and decelerating flow velocity to the cells in the tubing (Example 2).

Increased Modification Time

The preferred method for the production of the cells included a modification step, wherein the cells are modified for at least 0.5 hours, more preferably over 1 hour, even more preferably over 1.5 hours and even more preferably 2 hours or longer, such as 2 to 4 hours. It is realized that present reaction conditions allow maintaining the reactions over one hour, while an incubation of stem cells in salt solutions without divalent cations leads to apparently harmful morphological changes already within one hour (Example 1).

Glycan Modification Including Shear Force

The invention is in a preferred embodiment directed to modification of adherent cells including at least one step of exposing cells to shear force. It is realized that the cells may adhere to each other and/or cell culture support during the modification reagent, and this would reduce the effect of the cell modification reaction(s) and may diminish their viability (Example 2).

More preferably cells are exposed to shear forces for maintaining unicellular cell state in presence of divalent cations, preferably $Ca^{2+}$ and/or $Mg^{2+}$. It is realized that the presence of divalent cations increase cell adhesion by the receptors dependent on divalent cations.

In a preferred embodiment the cells are exposed to the shear stress for at least one period during the modification reaction for time allowing suspension of cell starting to adhere to suspend to unicellular composition. In a preferred embodiment the shear stress is administered for at least three, and more preferably at least four periods. In preferred embodiment the length of the period is at least 5 seconds, more preferably at least 15 seconds, and most preferably at least 30 seconds.

In preferred embodiment the shear force is administered by mechanical agitation of the cell preparation in solution. The mechanical agitation includes administration of the cells through a hole or tube, which is narrow enough to provide shear stress to cells. More preferably the shear stress is administered by sucking cells into a tip structure similar to pipette tip, preferably a tip of a Biohit m1000 pipette with Art 1000E filter tip (Example 2).

Reaction Time and Enzyme Concentration

The invention revealed that optimal reaction can be obtained by using proteolytic enzyme in relatively large concentrations and amount per cells (Example 3).

Spontaneous Glycomodification after Trypsin Treatment

Spontaneous cell modification was observed when trypsin-treated cells were incubated with the non-toxic divalent cations and additional beneficial factors according to the invention (Example 1).

It is realized that the prior art conditions of Sackstein did not reveal spontaneous cell modification according to the present invention, especially spontaneous synthesis of fucosylated structures. Apparently, although the cells are viable under the non-divalent cation conditions of Sackstein, they are not biosynthetically fully active. Furthermore the status of the cells under these conditions is so compromised that the longer reactions appear not possible without additional damage to cells. This may seriously limit the therapeutic use of this method.

The present conditions may be obvious for maintaining metabolic activity of the cells, but the increase of sialyl-Lewis x structures (Example 1), especially the core 2 sialyl-Lewis x epitope was not expected. It is realized that the spontaneous cell surface modification appears partially be related to glycoprotein recovery on cells, furthermore the present media is considered to support the machinery for endogenous glycosylation.

The present invention is further directed to use of the spontaneous modifications together with in vitro modification of the cells.

Modification Conditions for Mesenchymal Stem Cells

Preferably mesenchymal stem cells are modified to increase sialylation and/or fucosylation as a combination method, preferably by preferred transferases for sialyl-LacNAc synthesis and fucosylation such as STGalIII and Fuc-TVI.

Preferred fucosyltransferase conditions include about 4 mU (especially for Fuc-TVI, Calbiochem enzyme and units, fresh enzyme) per 3 million cells, or from 0.5 to 5 mU per million cells, more preferably 0.75-3 mU, and most preferably 1-2 mU per million cells. The preferred range depends on the status of the enzyme (decays during storage) and status and type of the cells. The preferred reaction temperature is about 37° C., preferably between 33-40° C. and more preferably 35-39° C. The preferred reaction times varies from 0.5 to 6 hours preferably between 1-6 hours, more preferably between 2-6 hours, even more preferably between 3-5.5 hours and in a preferred embodiment about 4 hours (3.5-4.5 hours). It is realized that increasing the enzyme amount reduces reaction time needed.

Preferred sialyltransferase conditions includes about 50 mU (especially for α2,3-(N)Sialyltransferase (Calbiochem), Calbiochem enzyme and units, fresh enzyme) per 1 million cells, or from 5 to 200 mU per million cells, more preferably 10-150 mU, and most preferably 25-75 mU per million cells. The preferred range depends on the status of the enzyme (decays during storage) and status and type of the cells. The preferred reaction times varies from 0.5 to 6 hours preferably between 1-6 hours, more preferably between 2-6 hours, even more preferably between 3-5.5 hours and in a preferred embodiment about 4 hours (3.5-4.5 hours). The preferred reaction temperature is about 37° C., preferably between 33-40° C. and more preferably 35-39° C. It is realized that increasing the enzyme amount reduces reaction time needed.

The invention is especially directed to modification of stem cells especially mesenchymal stem cells wherein the cells have unusually low sialylation levels. The cells with low sialylation comprise more than 30% of N-glycans in non-sialylated form. In a preferred embodiment the mesenchymal stem cell with low sialylation is a bone marrow derived mesenchymal stem cell (Example 6, Example 9).

Preferred Glycosylation Levels for Modification of Cells

The present invention revealed that it is possible to glycosylate cells, preferably to silylate cells to over 50% level of available free sialylation sites on N-glycans (when calculated based on the disappearance of the sialylation sites). In a preferred embodiment the invention is directed to sialylation by single sialyltransferase to level over 60%, more preferably over 70%, even more preferably over 75%, even more preferably over 80%, or at least 83%, and most preferably over 85%. The invention is further directed to a novel mesenchymal stem cell population comprising increased sialylation of over 60%, more preferably over 70%, even more preferably over 75%, even more preferably over 80%, or at least 83%, and most preferably over 85%. The cell population is preferably derived from human cord blood or bone marrow.

Characteristics of Novel Cells

Viable, Intact Cells

The invention is directed to the novel cells, wherein the cells are at least 98% viable as indicated by intact plasma membrane, most preferably over 99% as indicated by intact plasma membrane. The invention revealed that under the preferred cell modification condition, including e.g. non-toxic cations, leads to highly viable cells, especially, when the cells are produced under conditions in which adherence is actively inhibited by shear force. The preferred viable mesenchymal cells according to the invention have intact plasma membrane (Example 2).

The invention further revealed that the control cells did suffer from the incubation in the buffer without the beneficial reagent according to the present invention. It is realized that though the control cells have mostly intact membranes their overall viability and normal cell status is compromised.

Preferred Markers of Protease Produced Glycan Modified Cells

The invention revealed referred markers of novel glycan modified cell populations, preferably protease produced glycan modified cell populations. The invention is especially directed to in vitro fucosylation methods, when fucosylation increases amount of core 2 sLex, especially epitope similar to one recognized by antibody CHO-131. This structure is effectively formed under present cell modification conditions. The optimal production is obtained by spontaneous regeneration of glycosylation, preferably fucosylation by endogenous fucosyltransferase, and/or by in vitro glycosylation preferably fucosylation or fucosylation and sialylation, preferably by both.

Effects of Sialylation and Fucosylation

The invention revealed that the sialylation and fucosylation reactions according to the invention increased specific high MAA subpopulation of the mesenchymal cells. MAA recognizes a specific highly α3-sialylated in the novel cell populations (Example 1). The fucosylation and sialylation reactions further provide effectively the production of sialyl-CD15 and core 2 sLex (antibody CHO-131) epitopes.

Cells with Lower Amount of Sialylated Glycomarkers

The invention is in a preferred embodiment directed to modification of specific mesenchymal stem cell preparations, in a preferred embodiment produced by protease, such as trypsin treatment wherein the amount of certain glycan structures are reduced (Example 1): the amount of N-glycans, which can be modified by sialylation on cell surface, or the amount of specific non-N-glycan sLex (sialyl-Lewis x) epitope, preferably O-glycan associated glycans, especially GF526 epitope (antibody clone CHO-131). The GF526 epitope is core 2 O-glycan, comprising sLex on β6-linked arm. The structure is in other context associated with PSGL-1 protein.

Quantitative Change of Sialylation Levels

The invention revealed that it is possible to change quantitatively the sialylation levels of human cells. The signals of monosialylated and disialylated sialic acids of biantennary N-glycan cores were measured by MALDI-TOF mass spectrometry of released non-modified N-glycans. It was observed that the sialylation levels of the N-glycans of cells could be increased at least by 15% units and even by about 20% or 25% by sialylation of the cells by sialyltransferase enzyme. It was also observed that the sialylation levels of the N-glycans of cells could be decreased at least by 15% units and even by about 20% or 25% by sialylation of the cells by sialylidase (neuraminidase) enzyme.

The invention is especially directed to cell populations of quantitatively increased and decreased sialylation levels.

The invention revealed furthermore that the α3-sialylated cells can be fucosylated to produce cells increased in their sialylated and fucosylated levels, comprising sialyl-Lewis x Neu5Acα3Galβ4(Fucα3)GlcNAc (sLex) and related structures. It is realized that sLex content can be further increased by first resialylating the cells and thus reducing α6-sialylated structures blocking sites. Such sialyl-Lewis x cells are especially useful for in vivo targeting as the structures produced in low amounts from endogenous Neu5Acα3Galβ4GlcNAc can redirect the cells (Xia et al. 2004) (Example 1).

Biological Use of the Modified Cells

It is realized that the novel cells produced by the invention are useful for in vivo targeting in human and animal trials, or potentially in therapeutic applications.

The invention is in a specific embodiment directed to altering surface adhesion of glycan modified cells. It is thus realized that glycan modification can be used to change adherence properties of cells. The change of adherence properties is used for e.g.

For in vivo targeting methods such as targeting cells to a particular tissue, as described by Sackstein and colleagues;

In vitro methods requiring altered cell adherence such as attaching cells for detection of cells, in a preferred embodiment as adherent cells e.g. for microscopy or as soluble cells e.g. in flow cytometry or use of the adherent or soluble cells for cell adhesion studies, preferably for adhesion studies with lectins such as selectins;

Ex vivo cell culture methods producing transient cell modifications for subsequent in vivo targeting.

The invention is in a specific embodiment directed to cell culture of glycan modified cells with altered adherence properties. In a preferred embodiment the cells are cultured after modification, meaning increase of sialylation by sialyltransferase or reduction of sialic acids by sialidase enzyme. In a preferred embodiment the invention is directed to modification of naturally adherent cells, preferably mesenchymal stem cells.

Refinements of the Present Invention

Removable Enzymes by Tagging

The invention revealed novel effective methods for modifying cells by glycosyl modifying enzymes such as glycosidases and/or glycosyltransferases, when the enzymes are removed from the cell preparations. The invention is especially directed to use of specific tag-structures for the removal of the enzymes from the cells (Example 5).

Release of Enzymes by Carbohydrate Enzyme Inhibitors

It is realized that enzymes bind cells by their carbohydrate binding sites such as catalytic sites. In another embodiment the enzymes are removed by incubating the cells with an inhibitor of the enzymes, preferably an inhibitor binding to the catalytic carbohydrate recognizing site of the enzyme. Preferred inhibitors include monosaccharides and monosaccharide glycosides such as methyl and ethyl glycosides and more specific inhibitors, which may be designed based on the catalytic site as transition state inhibitors. Preferred inhibitors for sialidases include competitive low activity inhibitors such as sialic acid, and modified or low cost competing substrates such as NeuAcαOMe, NeuNAcαOEt, sialyl-Lactoses available e.g. from bovine milk or polysialic acid available from bacteria (E. coli, colomnic acid): and higher activity inhibitors such as NeuAc2en (NeuNAc with double bond between 2- and 3-positions) or e.g. higher activity inhibitors specific for limited number of enzymes such as influenza virus neuraminidase inhibitors: Tamiflu (oseltamivir, Roche) or Zanamivir (GSK).

The amount of enzyme inhibitor needed can be estimated by inhibition constants. Competitive monosaccharide glycoside or oligosaccharide inhibitors with low millimolar inhibition (or binding constants) are typically needed in amounts of several fold or order of magnitude larger amounts than the inhibition constant. Typical concentrations for the low affinity inhibitors are of about 1-500 mM, more preferably 1-250 mM, and more preferably 2-100 mM, or 2 to 50 mM, even more preferably from about 2 mM to 20 mM. The lower ranges are preferred to maintain the stability and osmotic condition of the cells stable. Typical concentrations for higher affinity inhibitors are from about 1 pM to about 10 mM, depending about the affinity constants. Preferred concentrations for low range micromolar inhibitor are between 10-1000 micromolar. Suitable inhibition concentrations are available from literature.

The invention is directed for removing modification enzyme from modified cells involving a step of incubation of the cells with an inhibitor or substrate of the enzyme. The method preferably further comprises steps of washing cells with a suitable solution such as PBS (phosphate buffered saline) or other solution suitable, optionally containing additional amount of inhibitor, and preferably a step of final washing with the solution not comprising the inhibitor.

In an embodiment the invention is directed to removal of the enzyme by a combination of the enzyme tagging with the use of the inhibitors.

Specifications of Glycomodifications
Desialylation Methods

The invention is specifically directed to desialylation methods for modification of human cord blood cells. The cord blood cells are clearly different of other cell types and no desialylation methods have previously been developed for these cells. Due to cell specific differences any quantitative desialylation methods cannot be generalized from one cell population to another. Thus, any results and data demonstrated by other investigators using other cell types are not applicable to cord blood. The present invention is further directed to desialylation modifications of any human stem cell or cord blood cell subpopulation.

The invention is preferably directed to linkage specific α3-desialylation of the preferred structures according to the invention without interfering with the other sialylated structures according to the present invention. The invention is further directed to simultaneous desialylation α3- and α6-sialylated structures according to the present invention.

Furthermore the present invention is directed to desialylation when both NeuAc and NeuGc are quantitatively removed from cell surface, preferably from the preferred structures according to the present invention. The present invention is specifically directed to the removal of NeuGc from preferred cell populations, most preferably cord blood and stem cell populations and from the preferred structures according to the present invention.

Modification of Cell Surfaces of the Preferred Cells by Glycosyltransferases

The inventors revealed that it is possible to produce controlled cell surface glycosylation modifications on the preferred cells according to the invention.

The present invention is directed to cell modifications by sialyltransferases and fucosyltransferases. Two most preferred transfer reactions according to the invention are α3-modification reactions such as α3-sialylation and α3-fucosylations. When combined these reactions can be used to produce important cell adhesion structures which are sialylated and fucosylated N-acetyllactosamines such as sialyl-Lewis x (sLex).

Possible α6-sialylation has been implied in bone marrow cells and in peripheral blood CD34+ cells released from bone marrow to circulation by growth factor administration, cord blood cells or other stem cell types have not been investigated. Furthermore, the previous study utilized an artificial sialic acid modification method, which may affect the specificity of the sialyltransferase enzyme and, in addition, the actual result of the enzyme reaction is not known as the reaction products were not analyzed by the investigators. The reactions are likely to have been very much limited by the specificity of the α6-sialyltransferase used and cannot be considered prior art in respect to the present invention.

The inventors of the present invention further revealed effective modification of the preferred cells according to the present inventions by sialylation, in a preferred embodiment by α3-sialylation.

The prior art data cited above does not indicate the specific modifications according to the present invention to cells from early human blood, preferably cord blood, to cultured mesenchymal stem cells, or to cultured embryonal type cells. The present invention is specifically directed to sialyltransferase reactions towards these cell types. The invention is directed to sialyltransferase catalyzed transfer of a natural sialic acid, preferably NeuAc, NeuGc or Neu-O—Ac, from CMP-sialic acid to target cells.

Sialyltransferase catalyzed reaction according to Formula:

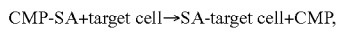

Wherein SA is a sialic acid, preferably a natural sialic acid, preferably NeuAc, NeuGc or Neu-O—Ac and
the reaction is catalysed by a sialyltransferase enzyme preferably by an
α3-sialyltransferase
and
the target cell is a cultured stem cell or early human blood cell (cord blood cell).

Preferably the sialic acid is transferred to at least one N-glycan structure on the cell surface, preferably to form a preferred sialylated structure according to the invention.

In the prior art fucosyltransferase reactions towards unspecified cell surface structures have been studied. The prior art indicates that human cord blood cell populations may be α3-fucosylated by human fucosyltransferase VI and such modified cell populations may be directed to bone marrow due to interactions with selectins.

Methods for Combined Increased α3-Sialylation and α3 Fucosylation

The invention is specifically directed to selection of a cell population from the preferred cell population according to the present invention, when the cell population demonstrate increased amount of α3-sialylation when compared with the baseline cell populations.

The inventors revealed that human cord blood in general is highly α6-sialylated and thus not a good target for α3/4-fucosylation reactions, especially for reactions directed to production of selectin ligand structures.

Fucosylation of α3-Sialylated Cells

The present invention is preferably directed to fucosylation after α3-sialylation of cells, preferably the preferred cells according to the invention. The invention describes for the first time combined reaction by two glycosyltransferases for the production of specific terminal epitopes comprising two different monosaccharide types on cell surfaces.

Production of Preferred Sialylated Structures

Present invention is specifically directed to methods for sialylation to produce preferred structures according to the present invention from the surfaces of preferred cells. The present invention is specifically directed to production preferred NeuGc- and NeuAc-structures. The invention is directed to production of potentially in vivo harmful structures on cells surfaces, e.g. for control materials with regard to cell labelling. The invention is further directed to production of specific preferred terminal structure types, preferably α3- and α6-sialylated structures, and specifically NeuAc- and NeuGc-structures for studies of biological activities of the cells.

The present invention is further directed to preferred methods for the quantitative verification of the sialylation by the preferred analysis methods according to the present invention. The present invention is further directed to linkage specific sialylation and analysis of the linkage specific sialylation on the preferred carbohydrate structures using analytical methods according to the present invention.

The invention is preferably directed to linkage specific α3-sialylation of the preferred structures according to the invention without interfering with the other sialylated structures according to the present invention. The invention is preferably directed to linkage specific α6-sialylation of the preferred structures according to the invention without interfering with the other sialylated structures according to the present invention.

The invention is further directed to simultaneous sialylation α3- and α6-sialylated structures according to the present invention. The present invention is further directed for the production of preferred relation of α3- and α6-sialylated structures, preferably in single reaction with two sialyl-transferases.

Furthermore the present invention is directed to sialylation when either NeuAc or NeuGc are quantitatively synthesized to the cell surface, preferably on the preferred structures according to the present invention. Furthermore the invention is directed to sialylation when both NeuAc and NeuGc are, preferably quantitatively, transferred to acceptor sites on the cell surface.

The present invention is specifically directed to the removal of NeuGc from preferred cell populations, most preferably cord blood cell populations and from the preferred structures according to the present invention, and resialylation with NeuAc.

The invention is further directed to preferred methods according to the present invention for verification of removal of NeuGc, and resialylation with NeuAc, preferably quantitative verification and more preferably verification performed by mass spectrometry with regard to the preferred structures.

Controlled Cell Modification

The present invention is further directed to cell modification according to the invention, preferably desialylation or sialylation of the cells according to the invention, when the sialidase reagent is a controlled reagent with regard of presence of carbohydrate material.

Purification of Cells with Regard to Modification Enzyme

The preferred processes according to the invention comprise of the step of removal of the enzymes from the cell preparations, preferably the sialyl modification enzymes according to the invention. Most preferably the enzymes are removed from a cell population aimed for therapeutic use. The enzyme proteins are usually antigenic, especially when these are from non-mammalian origin. If the material is not of human origin its glycosylation likely increases the antigenicity of the material. This is particularly the case when the glycosylation has major differences with human glycosylation, preferred examples of largely different glycosylations include: prokaryotic glycosylation, plant type glycosylation, yeast or fungal glycosylation, mammalian/animal glycosylation with Galα3Galβ4GlcNAc-structures, animal glycosylations with NeuGc structures. The glycosylation of a recombinant enzyme depends on the glycosylation in the production cell line, these produce partially non-physiological glycan structures. The enzymes are preferably removed from any cell populations aimed for culture or storage or therapeutic use. The presence of enzymes which have affinity with regard to cell surface may otherwise alter the cells as detectable by carbohydrate binding reagents or mass spectrometric or other analysis according to the invention and cause adverse immunological responses.

Under separate embodiment the cell population is cultured or stored in the presence of the modification enzyme to maintain the change in the cell surface structure, when the cell surface structures are recovering from storage especially at temperatures closer physiological or culture temperatures of the cells. Preferably the cells are then purified from trace amounts of the modification enzyme before use.

The invention is furthermore directed to methods of removal of the modification reagents from cell preparations, preferably the modification reagents are desialylation or resialylation reagents. It is realized that soluble enzymes can be washed from the modified cell populations. Preferably the cell material to be washed is immobilized on a matrix or centrifuged to remove the enzyme, more preferably immobilized on a magnetic bead matrix.

However, extraneous washing causes at least partial destruction of cells and their decreased viability. Furthermore, the enzymes have affinity with regard to the cell surface. Therefore the invention is specifically directed to methods for affinity removal of the enzymes. The preferred method includes a step of contacting the modified cells with an affinity matrix binding the enzyme after modification of the cells.

Under specific embodiment the invention is directed to methods of tagging the enzyme to be removed from the cell population. The tagging step is performed before contacting the enzyme with the cells. The tagging group is designed to bind preferably covalently to the enzyme surface, without reduction or without major reduction of the enzyme activity. The invention is further directed to the removal of the tagged enzyme by binding the tag to a matrix, which can be separated from the cells. Preferably the matrix comprises at least one matrix material selected from the group: polymers, beads, magnetic beads, or solid phase surface.

Tagging of Enzyme for Modification Glycan Controlled Enzymes

The invention is furthermore directed to methods of removal of the modification reagents from cells to be depleted of sialic acid and/or resialylated. The preferred modification reagents are desialylation or resialylation reagents. The reagents are tagged to be able to bind the reagents to solid phases comprising specific binder recognizing the tag, the tag binder combination e.g. on microbeads can be removed.

Preferred Tags Include antigens such as peptide FLAG or HA-hemagglutinin peptide tag, or
chemical tags such as His-tag or fluoroalkane or
biotin.

The invention is directed to known specific binders for these, such as specific antibodies for peptides, his-tag binding column for His-TAG, fluoroalkane for hydrogen bond binding of fluoroalkane and avidin or streptavidin for biotin are used.

Preferred modification enzymes and enzymes to be tagged include sialidase (neuraminidases) such as α3-, α6- and multispecific sialidases and α3-, α6-sialyltransferases for example from mammalian or bacterial origin and specific for type I and/or type II N-acetyllactosamines, preferably type two N-acetyllactosamines and N-glycans especially biantennary and triantennary N-glycans known in the art. The invention is specifically directed to preferred tagged enzymes as substances.

Preferred bacterial fucosyltransferases include enzymes homologous to human α3/4-fucosyltransferases, such as *Helicobacter pylori* fucosyltransferases homologous to enzyme described in Sun H-Y. J. Biol. Chem. (2007) manuscript M601285200, published 24.1.2007. The preferred specificities of bacterial such as *H. pylori* fucosyltransferase include reaction with 3' modified lactosamines such as Neu5Acα3Galβ4GlcNAc to synthesize sialyl-Lewis x, known to be produced at least by part of *H. pylori* strains.

Under specific embodiment the invention is directed to methods of tagging the enzyme to be removed from the cells.

Preferably a sialidase enzyme or sialyltransferase is linked to tag-molecule, the tagged enzyme is reacted with the cells to be remodeled and the enzyme is removed after the reaction by immobilizing the enzyme by binding to a molecule specifically binding to the tag and the modified cell(s) are removed from the immobilized enzyme by filtering the cells with matrix of a molecule specifically binding to the tag, preferred matrices include column used for cell purification or magnetic beads used for purification of components from cell mixtures (see protocols or catalogs of Dynal and Miltenyi companies).

The tagging step is preferably performed before contacting the enzyme with the cells. The tagging group is designed to bind preferably covalently to the enzyme surface, without reduction or without major reduction of the enzyme activity. Preferred covalent linkage occurs to amine groups, thiol group or oxidized glycan groups as known from catalogue of Pierce.

The invention is further directed to the removal of the tagged enzyme by binding the tag to a matrix, which can be separated from the cells to be modified. Cells proteins are preferably separated from tag-binder immobilized reagents in aqueous media as known in the art of using the tags. Preferably the matrix comprises at least one matrix material selected from the group: polymers, beads, magnetic beads, or solid phase surface.

Enzymes Acceptable for Humans for Modification of Reagents or Cells

Under specific embodiment the invention is directed to the use for modification of the cells according to the invention, or in a separate embodiment reagents for processes according to the invention, of a human acceptable enzyme, preferably sialidase or sialyltransferase, which is acceptable at least in certain amounts to human beings without causing harmful allergic or immune reactions. It is realized that the human acceptable enzymes may not be needed to be removed from reaction mixtures or less washing steps are needed for desirable level of the removal. The human acceptable enzyme is in preferred embodiment a human glycosyltransferase or glycosidase. The present invention is separately directed to human acceptable enzyme which is a sialyltransferase. The present invention is separately directed to human acceptable enzyme which is a sialidase, the invention is more preferably directed to human sialidase which can remove specific type of sialic acid from cells.

In a preferred embodiment the human acceptable enzyme is purified from human material, preferably from human serum, urine or milk. In another preferred embodiment the enzyme is recombinant enzyme corresponding to natural human enzyme. More preferably the enzyme corresponds to human natural enzyme corresponds to natural cell surface or a secreted form of the enzyme, more preferably serum or urine or human milk form of the enzyme. Even more preferably the present invention is directed to human acceptable enzyme which corresponds to a secreted form of a human sialyltransferase or sialidase, more preferably secreted serum/blood form of the human enzyme. In a preferred embodiment the human acceptable enzyme, more preferably recombinant human acceptable enzyme, is a controlled reagent with regard to potential harmful glycan structures, preferably NeuGc-structures according to the invention. The recombinant proteins may contain harmful glycosylation structures and inventors revealed that these kinds of structures are also present on recombinant glycosyltransferases, even on secreted (truncated) recombinant glycosyltransferases.

Quantitative and qualitative mass spectrometric analysis of modified cells and or reagents The present invention is further directed to the quantitative and qualitative mass spectrometric analysis of modified cells and/or reagents according to the invention.

The invention is directed to production of qualitative glycome analysis of the cell and/or the reagents including determining the monosaccharide composition obtained for the materials.

The present invention is further directed to quantitative mass spectrometric analysis of the materials according to the invention involving determining the intensities of all or part of the mass spectrometric signals verified to be (reasonably) quantitative with regard to the amount of molecules corresponding to the signals, preferably MALDI-TOF mass spectrometric signals.

The invention is further directed to methods, especially research an development methods, such as product development methods, according to the invention for production of reagents or cells as described by the invention involving step of quantitative and/or qualitative glycome analysis, more preferably both quantitative and qualitative analysis.

Preferred Glycan Controlled Reagents and Processes for Preparation Thereof.

Preferred reagents to be controlled include preferably all reagents derived from or produced in connection with biological material; preferably these include all glycoprotein, protein mixture, serum, and albumin preparations present in the process. The inventors found out that albumins known to be non-glycosylated proteins may still contain sufficient glycoproteins for contamination of cell material.

In a preferred embodiment the present invention is directed to the control of animal albumins, preferably bovine serum albumin, and human serum albumin preparations for potential contamination by glycan structures.

Other preferred controlled reagents include controlled transferrin and other serum proteins, even more preferably controlled serum proteins are controlled antibody preparations, preferably Fc blocking antibody preparations.

In yet another embodiment the invention is directed to the production of glycan depleted and/or remodeled protein mixtures preferably glycan remodeled human or animal serum, more preferably a serum from an animal used for production of serum products, preferably cell culture serum or antibodies. Preferred serums to be modified includes serum of cow, horse, sheep, goat, rabbit, rat or mouse, more preferably serum of cow, horse, or sheep, even more preferably fetal bovine serum.

In a preferred embodiment the glycosylation of the serum is altered by a method based on animals with genetically altered glycan production preferably obtained by a) genetic manipulation of the animal or b) breeding a natural or selecting a natural variant of the production animal to used for serum production, preferably the genetic alteration is directed to tissues producing serum proteins.

Controlled Enzyme Preparations for Products Aimed for Use with Transplantable Cells The present invention is directed under specific embodiment to methods for removal of non-desired carbohydrate structures from living cells. The enzyme proteins are usually antigenic, especially when these are from non-mammalian origin, such as bacteria and/or plants. If the material is not of human origin its glycosylation likely increases the antigenicity of the material. This is particularly the case when the glycosylation has large differences with human glycosylation, preferred examples of largely different glycosylations include: prokaryotic glycosylation, plant type glycosylation, yeast or fungal glycosylation, mammalian/animal glycosylation with Galα3Galβ4GlcNAc-structures, animal glycosylation with NeuGc structures. The glycosylation of a recombinant enzyme depends on the glycosylation of the production cell line, these produce partially non-physiological glycan structures in most cases.

Preferred Classes of Controlled Reagents
Glycan Depleted Biological Materials, Preferably Glycoprotein Materials Present invention is specifically directed to use biological materials, preferably glycoprotein material, from which harmful structure is removed or reduced in amount. Glycoproteins are major source of bioactive glycans, in some material presence of glycolipids may be also possible and could be handled similarly. In case the lipid part of glycolipid binds it to the material, released glycan or part of it is water soluble and can be separated. The invention is further directed to glycan depletion methods. In a preferred embodiment the invention is directed to methods including steps of releasing glycan structure and removing released glycan structure.

Preferred methods for removal of the released glycan structure include filtration methods. The filtration methods are based on size difference of the released glycan structure and the glycan depleted protein. A preferred method for removal of the released glycans includes precipitation methods, in a preferred embodiment the invention is directed to precipitation of the protein under conditions where the released glycan structure is soluble.

The glycan depletion may be combined with a step of inactivation of potential harmful proteins such as lectins or antibodies possibly involved in the process. Some reagents such serum in certain cell culture processes may be heat inactivated. The inactivation may be partial. The partial inactivation is in a preferred embodiment performed by releasing glycans inhibiting the harmful binding proteins to the reagent and further to cell involving process. In a preferred embodiment the depleted glycan and the binding protein inhibiting glycan is the same structure. Preferably the released glycans are used when these can not be incorporated to cells to cause further problems in the cell related process. The method of released glycans is not preferred for NeuGc under conditions where it can be incorporated to cells.

Terminally Depleted Glycans

In a preferred embodiment one or several terminal structures are depleted from a biological material, preferably glycoprotein material. The preferred methods to deplete terminal structures include enzymatic and chemical methods. Preferred enzymatic method is hydrolysis by a glycosidase enzyme or by a trans-glycosylating enzyme capable of removing the terminal structure. Terminal depletion may further include release of several terminal monosaccharide units for example by glycosidase enzymes. Preferred chemical hydrolysis is an acid hydrolysis, preferably a mild acid hydrolysis under conditions not destroying protein structure or from which the protein structure can be restored or renatured. The structure to be depleted is in a preferred embodiment a sialic acid. The sialic acid is preferably released by a sialidase enzyme or by mild acid hydrolysis.

Internally Depleted Glycans

The present invention is further directed to internal depletion of glycan material by release of glycans from subterminal linkages by chemical and/or enzymatic methods. Methods to release glycans chemically include base hydrolysis methods such as beta elimination for release of O-linked glycans, hydrazinolysis methods to release O-glycans and N-glycans, oxidative methods such as Smith degradation and ozonolysis (preferred for glycolipids). Preferred enzymatic methods include use of endo-glycosidases such as endoglycosylceramidase for glycolipids, N-glycosidases for N-glycans, and O-glycosidases for O-glycans.

Glycosylated Reagents from Non-Animal Sources

In a preferred embodiment the present invention is directed to the use of reagents from non-animal sources devoid of potentially harmful reagents. Preferred non-animal glycosylated proteins are proteins from yeasts and fungi and from plants. It is notable that even these materials contain glycans, which may have harmful allergenic activities or which may cause problems in analysis of human type glycans. Preferably the invention is further directed to control of the glycosylated reagents from non-animal structures, too. Preferred plant derived proteins include recombinant albumins produced by plant cell culture, more preferably non-glycosylated human serum albumins and bovine serum albumins and recombinant gelatin materials such as collagens produced by plant cell systems. The present invention is specifically directed to the processes according to present invention, when a material containing glycans or harmful glycans according to the present invention is replaced by a reagent, preferably a controlled reagent from non-animal sources.

Non-Glycosylated Reagents from Prokaryotes

Many bacterial recombinant proteins are known for lacking expression of glycans. Present invention is directed to control of glycosylation of bacterial protein, as this happens on certain proteins. The present invention is specifically directed to the processes, when a material containing glycans or harmful glycans according to the present invention is replaced by a reagent, preferably a controlled reagent from prokaryotes.

Under specific embodiment the present invention is directed to use of glycan controlled forms of glycosidase enzymes for modification of transplantable cells according to the invention and removal of the enzymes from reactions as described by the present invention The present invention is also specifically directed to the glycan controlled enzyme preparations, especially when produced in a mammalian cell line/cultivation process and controlled with regard to Gal$\alpha$3Gal$\beta$4GlcNAc-structures, animal glycosylations with NeuGc structures. The preferred enzymes are of human origin, more preferably recombinant enzymes. Most preferably a human serum form of the enzyme is selected and the glycosylation is controlled to be a non-antigenic human-type glycosylation, preferably similar to the glycosylation human natural soluble enzyme.

Preferred Sialyl-Transferases

Preferred sialyltransferases includes mammalian, more preferably human $\alpha$3-, and $\alpha$6-sialyltransferases, preferably in soluble form. In a preferred embodiment the transferase sialylates N-acetyllactose amines such as ST3GalIII and ST3GalIV or ST6GalI or O-glycans core I such as ST3GalI or ST3GalII and ST3GalIV. It is realized that most effective sialylation is obtained with combination of at least two sialyltransferases such as core I sialylating and N-acetyllactosamine sialylating, e.g. ST3GalIII and ST3GalIV or ST3GalI/II and ST3GalV.

Preferred Fucosyltransferases

Preferred fucosyltransferases include mammalian, more preferably human $\alpha$3-, and $\alpha$6-fucosyltransferases, preferably in soluble form. In a preferred embodiment the transferase reacts with N-acetyllactosamines such as FTIII, FTIV, FTV, FTVI, FTVII and FTIX more preferably sialyl-$\alpha$3-N-acetyllactosamines, preferably FTIII, FTIV, FTV, FTVI, FTVII, more preferably FTIII, FTV, FTVI, and FTVII, even more preferably FTVI, and FTVII, and most preferably FTVI. It is realized that most effective fucosylation is obtained with combination of at least two fucosyltransferases.

In a preferred embodiment the galactosylation reaction is performed in the presence $Mg^{2+}$ ions as described in US2005014718, preferably by mammalian GalT, more preferably natural human GalT, or using exogenous transferase such as $Mg^{2+}$ selective β4-Galactosyltransferase of Qasba and Ramakrishnan.

It is realized that it is useful to remove exogenous GalT and/or sialyltransferase by using specific Tags according to the invention and/or by using enzyme inhibitors according to the invention.

Controlled Reagents for the Modification

In another preferred embodiment it is useful to use glycan controlled sialyltransferase or galactosyltransferase. The invention is directed to analysis of glycans of non-human expressed glycosyltransferases. When the transferases comprise non-human glycosylation, the non-human structures are preferably removed by specific glycosidases or modified by chemically e.g. by perjodate oxidation and reduction.

The invention is especially directed to use of controlled enzyme substances, preferably galactosyltransferase or sialyltransferase for reaction according to the invention comprising glycan according to Formula Manα6(Manα3)Manβ4GlcNAcβ4(Fucα6)nGlcNAc-N-E wherein E is enzyme protein, N is glycosidic linkage nitrogen in N-glycosylation site (Asn-X-Ser/Thr), and the non-reducing end mannoses may be further modified by (NeuNAcα3/6)mGalβ4GlcNAcβ2, wherein m and n are 0 or 1.

If the enzyme would comprise NeuNGc instead of NeuNAc, this is preferably removed and changed to NeuNAc.

In another preferred embodiment the enzymes are non-glycosylated preferably from bacterial production e.g. as described by Qasba US2007258986 (included fully as reference) or N-(Asn-X-Ser/Thr/Cys) and possible O-glycosylation sites of the enzymes are mutated for expression in eukaryotic system.

The structure is especially beneficial because Manβ4-residue is devoid of Xylβ2-modification present in plant cells and reducing end GlcNAc is devoid of Fucα3-structure present in insect or plant cell derived material (e.g. when the enzyme would be produced by insect or plant cell culture).

Glycosyltransferase Inhibitors for Release of Glycosyltransferase from Cells

The present invention is especially directed to use of analogs or derivatives of acceptor saccharides or donor nucleotides for inhibitors of glycosyltransferases for washing the transferase effectively from cells after the reaction. The preferred acceptor analogs include carbohydrates oligosaccharides, monosaccharides and conjugates and analogs thereof capable of binding to substrate site and inhibiting the acceptor binding of the enzyme. The preferred concentrations of the carbohydrates includes concentrations tolerable by the cells from 1 mM to 500 mM, more preferably 5 mM to 250 mM and even more preferably 10-100 mM, higher concentrations are preferred for monosaccharides and method involving solid phase bound binders.

Preferred oligosaccharide for sialyltransferase inhibition includes sequences including oligosaccharides and reducing end conjugates includes Galβ4Glc, Galβ4GlcNAc, Galβ3GlcNAc, Galβ3GalNAc depending. GalT inhibitors include GlcNAc and conjugates and GlcNAcβ2Man, GlcNAcβ6Gal and GlcNAcβ3Gal.

In a preferred embodiment sialyltransferase is released by acceptor disaccharide, more preferably by 5-150 mM acceptor, more preferably by 10-100 mM, even more preferably 10-80 mM, more preferably 10-50 mM for high affinity acceptor and 20-100 mM, more preferably 40-100 mM, most preferably 50-100 mM for low affinity acceptor. It is realized that acceptor affinities varies between enzymes, lactose is considered as medium low affinity acceptor for α2,3-(N)-Sialyltransferase (Calbiochem) or ST3GalIII and high affinity acceptors have typically acceptor Km values about 10 fold lower. Preferably washing removes at least 50% of the cell bound enzyme even more preferably at least, 70%, even more preferably at least 85%, even more preferably at least 90% and most preferably at least 95%.

The preferred reducing end structure in conjugates is AR, wherein A is anomeric structure preferably beta for Galβ4Glc, Galβ4GlcNAc, Galβ3GlcNAc, and alfa for Galβ3GalNAc and R is organic residue linked glycosidically to the saccharide, and preferably alkyl such as method, ethyl or propyl or ring structure such as a cyclohexyl or aromatic ring structure optionally modified with further functional group.

Preferred monosaccharides include terminal or two or three terminal monosaccharides of the binding epitope such as Gal, GalNAc, GlcNAc, Man, preferably as anomeric conjugates: as FucαR, GalβR, GalNAcβR, GalnacαR GlcNAcβR, ManαR. For example α3- or α6-sialyltransferase synthesizing sialyl Galβ4GlcNAc is preferably inhibited by Galβ4GlcNAc or lactose. Preferred donor analog includes CMP and derivatives for sialyl-transferases and UDP and derivatives for galactosyltransferases, the analogs preferably interfere also with acceptor binding so that the enzyme is released.

Sialyltransferase Catalyzed Transfer of a Natural Sialic Acid

The invention is directed to sialyltransferase catalyzed transfer of a natural sialic acid, preferably NeuAc, NeuGc or Neu-O—Ac, from CMP-sialic acid to target cells.

The invention provides sialyltransferase catalyzed reaction according to Formula CMP-SA+target cell SA-target cell+CMP, preferably CMP-SA+Galβ4/3GlcNAc–target cell→SAα3/6Galβ4/3GlcNAc–target cell+CMP, wherein SA is a sialic acid, preferably a natural sialic acid, preferably NeuAc, NeuGc or Neu-O—Ac and
the reaction is catalysed by a sialyltransferase enzyme preferably by an
α3-sialyltransferase
and
the target cell is a cultured stem cell or stem cell or early human blood cell (cord blood cell).

Preferred fucosyltransferase reactions synthesis of Lewis a and Lewis x and sialylated variant thereof are:

GDP-Fuc+Galβ4/3GlcNAc–target cell Galβ4/3(Fucα3/4)GlcNAc–target cell+GDP, and/or GDP-Fuc+SAα3Galβ4/3GlcNAc–target cell→SAα3Galβ4/3(Fucα3/4)GlcNAc–target cell+GDP.

Both synthesis of sialyl-Lewis x, SAα3Galβ4(Fucα3)GlcNAc, and sialyl-Lewis a, SAα3Galβ3(Fucα4)GlcNAc, are preferred, sLex more preferred, when the cells comprise mainly type 2 lacNAc acceptors common on mesenchymal stem cells.

The reaction is catalysed by a fucosyltransferase enzyme preferably by an α3/4-fucosyltransferase. α4-fucosyltransferases (Fuc-TIII and -TV) are preferred for synthesis of Lewis a. The novel fucosylated cell populations are preferred for functional studies of the structure.

Specifically Protein Conjugated Glycosyltransferases

The present invention is directed to glycosyltransferases, especially mammalian sialyl-transferases and fucosyltransferases which are effectively modified on lysine residues by NHS-biotin. This is unexpected as the enzymes contain lysine residues in active site regions, and modification of these would have been likely to reduce substantially or destroy the enzyme activities to non-useful levels.

The invention revealed useful but unexpectedly high reagent amounts needed to obtain effectively biotinylated proteins. The invention further revealed that it is possible to obtain unexpectedly high biotinylation level and retaining useful enzyme activity.

Preferred protein modified sialyltransferase enzymes or other transferase according to the invention are homologous N-acetyllactosamine sialylating α3-sialyltransferases including ST3GalIII, ST3GalIV and ST3GalVI, most preferably ST3GalIII-family enzymes. Preferred specifically protein modified fucosyltransferases include α3/4-fucosyltransferases Fuc-TIII, Fuc-TIV, Fuc-TV, Fuc-TVI, Fuc-TVII and Fuc-TIX, more preferably Fuc-TVI and Fuc-TVII and most preferably Fuc-TVI. In a preferred embodiment the invention is directed to biotinylated forms of bacterial glycosyltransferases, especially sialyltransferases and fucosyltransferases.

The invention is directed to novel substances according to the formula

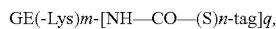
GE(-Lys)$m$-[NH—CO—(S)$n$-tag]$q$, wherein GE is glycosylation modification enzyme, including glycosyltransferring enzymes, glycocosidases and in separate embodiment also proteases and protease inhibitors;
more preferably glycosyltransferase, more preferably sialidase,
sialyltransferase or fucosyltransferase according to the invention,
Lys is lysine residue, presenting reactive primary amine on side chain,
alternatively an amine group may be represented by other structure preferably N-terminus of the protein,
S is spacer, n is 0 or 1, indicating either presence or absence of spacer, m is integer from 0 to about 20, varying between enzymes, and indicating the average number of lysines modified, q is integer from 1 to about 20, varying between enzymes, and indicating the number of tag molecules conjugated.

In a preferred embodiment GE is sialyltransferase or fucosyltransferase. In a preferred embodiment a low average level biotinylation is performed so that m is at least 0.8, more preferably at least 1.0, even more preferably at least 1.1, but less than 2. Preferred lower range average biotinylation levels for sialyltransferase are about 1.1. (preferably in range 0.8-1.4) and about 1.6 for fucosyltransferase (preferably in range 1.3.-1.9). The lower fucosylation is preferred especially for analysis purposes for observing enzymes on cell surfaces, when quantitative biotinylation of all enzyme proteins is not needed. It is realized that the lower level biotinylated enzymes have properties closer to the native enzyme, e.g. with regard to molecular weight.

In another preferred embodiment unexpected high biotinylation is targeted, so that m is preferably at least 2, even more preferably at least 2,5, even more preferably at least 3. In a specific embodiment GE is sialyltransferase and m is between 3 and 5, more preferably between 3.2 and 4, even more preferably between 3.25 and 3.8. In a preferred embodiment GE is α3-sialyltransferase, preferably ST3GalIII and it is modified to amine groups to contain about 3.5, more preferably about 3.4 (3.1-3.7 biotin residues). In other specific embodiment GE is fucosyltransferase and m is between 3 and 5, more preferably between 3.5 and 4.8 even more preferably between 3.6 and 4.5. In a preferred embodiment α3-fucosyltransferase, preferably Fuc-TVI is modified to amine groups to contain about 4, more preferably about 4.3 (4.0-4.6 biotin residues).

The invention revealed that it is possible to produce highly biotinylated sialyltransferases with useful activity. The high biotinylation level was revealed to include range of biotin residues so that practically each enzyme protein contains a biotin. The highly biotinylated enzymes are especially preferred for removal from the cell modification reactions, practically no enzyme was left. The invention revealed extremely efficient removal of the enzymes from reaction by solid phase conjugated binding reagent for the tag, especially streptavidin coated magnetic particles. The highly biotinylated active enzymes are thus preferred by the invention.

The invention is further directed to use of biotinylated enzymes with the reagents revealed to be effective in cell modification such as divalent cations and/or magnesium and/or calcium, supporting factors and non-glycoprotein. In a preferred embodiment highly biotinylated enzyme is used in a medium comprising biotin. The invention is especially directed to removal of the highly biotinylated enzymes even from biotin containing solutions, at least when the biotin concentration is not substantially higher than that in α-MEM, and optionally 1-2 washing steps are included to remove excess biotin, before the removal of the enzyme. In another preferred embodiment the invention is directed to the use of the supporting factors according to the invention and excluding biotin or using another tag such as fluorocarbon or peptide tag not included in the reaction mixtures.

Combined Sialyltransferase and Fucosyltransferase Reaction

The invention is further in a preferred embodiment directed to combined fucosyltransferase and sialyltransferase reaction with a broad specificity, sialyltransferase sialylating α3/4-fucosylated terminal oligosaccharide sequences such as Lewis x and/or Lewis a, preferably at least Lewis x, and an α3/4-fucosyltransferase reacting with both sialylated and non-sialylated acceptors.

Combined sialyltransferase and fucosyltransferase reactions for synthesis of sialyl-Lewis x and/or sialyl-Lewis a
Galβ4/3GlcNAc (Sialyltransferase and fucosyltransferase)
→NeuNAcα3Galβ4/3(Fucα3/4)GlcNAc.
More preferably synthesis of sLex
Galβ4GlcNAc (Sialyltransferase and fucosyltransferase)
→NeuNAc α3Galβ4(Fucα3)GlcNAc.

In a preferred embodiment broad specificity microbial enzyme is used for sialylation of Lewis x and optionally also LacNAcs on cell surface
Galβ4(Fucα3)GlcNAc (broad specificity Sialyltransferase)
→NeuNAcα3Galβ4(Fucα3)GlcNAc It is realized that these reactions are more effective than reactions with mammalian transferases, because the fucosylated sequences are not effective acceptors for mammalian sialyltransferases.

Conjugated Enzymes

The present invention is directed to the use of the specific enzyme for or in context of modification of the stem cells wherein the enzyme is covalently conjugated to a tag. The conjugation according to the invention may be performed non-specifically, e.g. by biotinylation one or several of multiple amines on the cell surface, or specifically.

Specific Conjugation

The specific conjugation aims for conjugation from protein regions, which does not disturb the binding of the binding site of the enzyme to its ligand glycan and/or donor nucleotide binding site of a glycosyltransferase to be modified on the cell surface glycans of stem cells according to the invention.

Preferred specific conjugation methods include chemical conjugation from specific amino acid residues from the surface of the enzyme protein/peptide. In a preferred method specific amino acid residue such as cysteine is cloned to the site of conjugation and the conjugation is performed from the cysteine. In another preferred method N-terminal cysteine is oxidized by periodic acid and conjugated to aldehyde reactive reagents such as amino-oxymethyl hydroxylamine or hydrazine structures, further preferred chemistries include "Click" chemistry marketed by Invitrogen and amino acid specific coupling reagents marketed by Pierce and Molecular probes.

A preferred specific conjugation occurs from protein linked carbohydrate such as O- or N-glycan of the enzyme, preferably when the glycan is not close to the binding site of enzyme substrates or longer spacer is used.

Glycan Conjugated Enzyme Protein

Preferred glycan conjugation occurs through a reactive chemoselective ligation group R1 of the glycans, wherein the chemical group can be specifically conjugated to second chemoselective ligation group R2 without major or binding destructive changes to the protein part of the enzyme. Chemoselective ligation groups reacting with aldehydes and/or ketones include as amino-oxy-methyl hydroxylamine or hydrazine structures. A preferred R1-group is a carbonyl such as an aldehyde or a ketone chemically synthesized on the surface of the protein. Other preferred chemoselective groups include maleimide and thiol; and "Click"-reagents (marketed by Invitrogen) including azide and reactive group to it.

Preferred synthesis steps include
chemical oxidation by carbohydrate selectively oxidizing chemical, preferably by periodic acid or
enzymatic oxidation by non-reducing end terminal monosaccharide oxidizing enzyme such as galactose oxidase or by transferring a modified aldehyde or ketone group comprising monosaccharide residue (such as Gal Comprising $CH_3COCH_2$— instead of OH on position 2) to the terminal monosaccharide of the glycan.

Use of oxidative enzymes or periodic acid are known in the art having been described in patent application directed conjugating HES-polysaccharide to recombinant protein by Kabi-Frensenius (WO2005EP02637, WO2004EP08821, WO2004EP08820, WO2003EP08829, WO2003EP08858, WO2005092391, WO2005014024 included fully as reference) and a German research institute.

Preferred methods for the transferring the terminal monosaccharide reside includes use of mutant galactosyl-transferase as described in patent application by part of the inventors US2005014718 (included fully as reference) or by Qasba and Ramakrishman and colleagues US2007258986 (included fully as reference) or by using method described in glycopegylation patenting of Neose (US2004132640, included fully as reference).

Conjugates Including High Specificity Chemical Tag

In a preferred embodiment the enzyme is, specifically or non-specifically conjugated to a tag, referred as T, specifically recognizable by a ligand L, examples of tag includes such as biotin binding ligand (strept)avidin or a fluorocarbonyl binding to another fluorocarbonyl or peptide/antigen and specific antibody for the peptide/antigen Tag-Conjugate Structures The preferred conjugate structures are according to the Formula CONJ B-(G-)$m$R1-R2-(S1-)$n$T, Wherein B is the enzyme, G is glycan (when the enzyme is glycan conjugated), R1 and R2 are chemoselective ligation groups, T is a tag, preferably biotin; S1 is an optional spacer group, preferably $C_1$-$C_{10}$ alkyls,
m and n are integers either 0 or 1, independently.

Methods to chemically attach spacer structures ligation groups or ligand such as (strept)avidin to solid phases is known in the art.

Complex Structure

When the enzyme is removed by using the tag following complex structure is preferably formed according to Formula COMP B-(G-)$m$R1-R2-(S1-)$n$T-L-(S2)$s$-SOL, Wherein B is the enzyme, SOL is solid phase or affinity matrix or polymer or other matrix useful for removal of the enzyme, G is glycan (when the enzyme is glycan conjugated), R1 and R2 are chemoselective ligation groups, T is tag, preferably biotin, L is specifically binding ligand for the tag; S1 and S2 are optional spacer groups, preferably C1-C10 alkyls, m, n, and s are integers being either 0 or 1, independently and linkage between T-L can be non-covalent high affinity binding.

Methods to chemically attach spacer structures or ligand such as (strept)avidin to solid phases are known in the art.

Use of the Tag Conjugates

A preferred method of the tag conjugate involves following steps:
1) Incubating the tagged enzyme with cells
2) Optional addition of enzyme inhibitor for the release of the enzyme from the cells
3) Contacting the releases tagged enzyme with a matrix comprising the specific ligand for the tag
4) Isolating the enzyme-matrix complex from the cells.

The matrix comprising the ligand may be solid phase or affinity matrix or polymer or other matrix useful for removal of the enzyme. The matrix may be used in form of magnetic particles, column, surface of tubing or vessel, soluble or insoluble preferably water miscible polymer.

In yet another preferred embodiment the tagged enzyme is used together with non-tagged enzyme in order to establish the level of non-tagged enzyme with same or very similar cell binding properties in a cell preparation, preferably aimed for therapeutic use, and removal of the tagged enzyme.

Novel Glycan Conjugates

The invention further revealed novel glycan conjugated enzymes. It is realized that the glycan conjugation surprisingly maintained the enzyme activity and allows effective reactions. The invention is further directed multiply Tag conjugated glycans preferably being on average about 3-15 tags, more preferably 4-12, most preferably 4-10 tags per enzyme.

The invention is especially directed to multiply conjugated tags on enzymes and/inhibitors according to the invention according to the Formula B-(G-)$m$[R1-R2-(S1-)$n$T]$q$     Formula CONJm Wherein B is the enzyme, SOL is solid phase or affinity matrix or polymer or other matrix useful for removal of the enzyme, G is glycan (when the enzyme is glycan conjugated), R1 and R2 are chemoselective ligation groups, T is tag, preferably biotin, L is specifically binding ligand for the tag; S1 is an optional spacer group, preferably C1-C10 alkyls,
m is integer from 1-50, indicating number of glycan epitopes to be modified,
n is integer being either 0 or 1, independently, q is integer from 1 to about 20, varying between enzymes, and indicating the number of tag molecules conjugated.

Methods to chemically attach spacer structures ligation groups or ligand such as (strept)avidin to solid phases are known in the art.

The invention is further directed to multivalent conjugates. When the enzyme is removed by using the tag following complex structure is preferably formed according to Formula COMPm

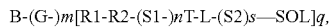
B-(G-)m[R1-R2-(S1-)nT-L-(S2)s—SOL]q, q is integer from 1 to about 20, varying between enzymes, and indicating the number of tag molecules conjugated,
other variables are as described for Formula COMP.

Novel Microbial Enzymes

The preferred bacterial enzymes includes α2,3-sialyltransferase from *Photobacterium phosphorium* and α2,6-sialyltransferase from *Photobacterium damselae*.

In a preferred embodiment the invention is directed to use of sialyltransferase which can sialylate (i) both fucosylated and non-fucosylated type II N-acetyllactosamines Galβ4GlcNAc and Galβ4(Fucα3)GlcNAc and (ii) optionally terminal type I N-acetyllactosamines Galβ3GlcNAc and Galβ3(Fucα3)GlcNAc and (iii) even more preferably also Galβ3GalNAcα sequences in O-glycans and/or Galβ3GalNAcβ in glycolipids.

Bacterial enzyme form α2,3-sialyltransferase from *Photobacterium* sialylates both type 1 and type II N-acetyllactosamines. A preferred sialyltransferase for sialylation for all the preferred acceptor types including type I and type II lactosamines, and glycolipid Galβ3GalNAcβ and fucosylated acceptors Galβ4(Fucα3)GlcNAc is a viral sialyltransferase from myxoma virus v-ST3GalI (Sujino et al. Glycobiology 2000 10 (3) 313-20). It is realized that the broad specificity sialyltransferases sialylate cells most effectively to multiple acceptor sites.

Synthesis and Analysis of Novel Sulfated Epitopes

Analysis of glycan structures of mesenchymal stem cells revealed presence of sulfated type II N-acetyllactosamine epitopes with sulfate on galactose residue and/or GlcNAc residue, PCT/FI2008/050019. The applicants further had O-glycan structures analyzed, and the positions of the sulfate modification in sulfated N-acetyllactosamines was determined by specific galactosidases either cleaving galactose from Galβ4(SE6)GlcNAc or not cleaving it. The analysis revealed that the sulfated N-acetyllactosamines of human mesenchymal cells, preferably mesenchymal stem cells contain sulfate on both Gal and GlcNAc residues of the N-acetyllactosamines (LacNAcs).

It is realized that the sulfated N-acetyllactosamines and their fucosylated and/or sialylated derivatives are useful markers for the analysis of glycomodified cells.

Preferred reactions with (SE6)GlcNAc containing structures includes fucosylation, sialylation or fucosylation and sialylation to synthesize
a) 6-sulfo-sialyl-LacNAc, b) 6-sulfo-Lewis x and c) 6-sulfo-sialyl-Lewis x: according to formulas:

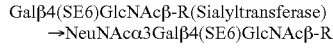
Galβ4(SE6)GlcNAcβ-R(Sialyltransferase)
→NeuNAcα3Galβ4(SE6)GlcNAcβ-R     a)

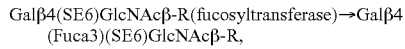
Galβ4(SE6)GlcNAcβ-R(fucosyltransferase)→Galβ4
(Fucα3)(SE6)GlcNAcβ-R,     b)

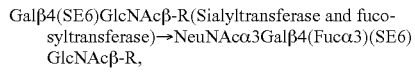
Galβ4(SE6)GlcNAcβ-R(Sialyltransferase and fucosyltransferase)→NeuNAcα3Galβ4(Fucα3)(SE6)
GlcNAcβ-R,     c)

wherein R is reducing end part of the glycan preferably 2Manα3/6-linked to N-glycan core or an O-glycan structure, preferably 6(Gal)GalNAcαSer/Thr.

Preferred reactions with (SE3)Gal containing structures include fucosylation,
a) 3' sulfo-fucosyl-LacNAc
according to the reaction formula:

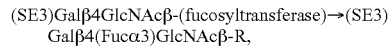
(SE3)Galβ4GlcNAcβ-(fucosyltransferase)→(SE3)
Galβ4(Fucα3)GlcNAcβ-R,     a)

wherein R is reducing end part of the glycan preferably 2Manα3/6-linked to N-glycan core or an O-glycan structure, preferably 6(Gal)GalNAcαSer/Thr.

Preferred reactions with (SE3)Galβ4(SE6)GlcNAc containing structures includes fucosylation,
a) 3'-,6-sulfo-fucosyl-LacNAc
according to the reaction:

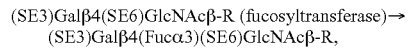
(SE3)Galβ4(SE6)GlcNAcβ-R (fucosyltransferase)→
(SE3)Galβ4(Fucα3)(SE6)GlcNAcβ-R,     a)

wherein R is reducing end part of the glycan preferably 2Manα3/6-linked to N-glycan core or an O-glycan structure, preferably 6(Gal)GalNAcαSer/Thr.

The invention is further directed to spontaneous fucosylation reactions to synthesize sialylated and/or fucosylated sulfo-N-acetyllactosamines.

Preferred reagents for the recognition of acceptor structures, preferably on non-modified cells according to the invention include sulfo-lactosamine structure recognizing antibodies, preferably 3' sulfo-LacNAc and 6-sulfo LacNAc, 3'-,6-sulfo-LacNAc specific antibodies and for the recognition of product structures antibodies for the corresponding fucosylated and/or sialylated structures. Examples of antibodies are in Table 3, in case specific antibody is not available combinations of the antibodies can be used or combinations of antibody and glycosidase analysis.

Effective Desialylation Reactions, and Reaction with Unusual Specificity and Novel Cell Products The present invention reveals an effective method to produce highly desialyated mesenchymal stem cells. It is realized that there are different sialylated structures on cell surface and these are differentially available for enzymes. α3-sialidase such as *Streptococcus* sp. sialidase could be used for specific α3-desialylation. Surprisingly the inventors revealed that a more general sialidase from *Vibrio cholerae* is capable of removing effectively and selectively sialic acid residues recognized by SNA (*Sambucus nigra* agglutintin) lectin, which correspond to α6-linked sialic acids. The invention is directed to use and method including α6-linkage favoring sialidase, preferably *Vibrio cholerae* type sialidase (neuraminidase) to remove with reasonable selectivity α6-linked sialic acids from cell surface to obtain novel preferred cell population with substantially reduced amount of α6-linked sialic acids. It was also revealed that the enzyme has some preference for sialic aid(s) on CHO131-antibody epitope but the α6-sialic acid is most effectively removed. In a preferred embodiment the invention is directed to sialylation alteration method wherein major part on first silic acid structure is removed from cell surface and substantial amount of second sialylglycan is added to the cell surface. In a preferred embodiment α6-linked sialic acid is removed by at least 10%, or other preferred amount according to the invention and sialic acid with α3- or α8-linkage, preferably α3-linked sialic acid is added preferably by a α3-sialyltransferase. In another preferred embodiment α3-linked sialic acid is removed by at least 10%, or other preferred amount according to the invention and sialic acid with α6- or α8-linkage, preferably α6-linked sialic acid is added preferably by a α6-sialyltransferase such as ST6Gal1.

The invention is especially directed to effective reduction of a sialylated epitope selected from a group α3-linked sialic acid, and/or α6-linked sialic acid and/or α-linked sialic acid, more preferably α3- and/or α6-linked on a cell surface, preferably on a human mesenchymal cell surface. The amount of sialic acid or α3-linked sialic acid detectable by α3-sialic acid binding lectin or antibody, preferably binding reagent selected from the group lectin MAA (Maackia amurensis agglutinin), MAL1 and a sialyl-lewis x recognizing antibody, preferably CHO131.

The specific sialic acid structure is removed preferably by at least 5% more preferably at least by 7.5%, even more preferably at least by about 9%, even more preferably by at least by 15%, even more preferably at least 20%. In a preferred embodiment α6-linked sialic acid is removed by at least 10%, more preferably by 20%, even more preferably by 30%, even more preferably by 40%, even more preferably by 50%, even more preferably by 60%, and most preferably at least by 70%. The invention is further directed to novel cell populations especially stem cells, more preferably mesenchymal stem cells comprising the reduced sialic acid amounts. In a preferred embodiment the invention is directed to cells with more than 35% (or other preferred amount described above), more preferably at least about 50%, and most preferably at least about 60% reduced α6-sialylation and optionally about 5-30% reduced α3-sialylation. In a preferred embodiment the sialylation is altered and the novel cell population is produced by method(s) according to the invention including use of specifically selected enzymes, in a preferred embodiment $V.$ $cholerae$ sialidase or a sialidase with similar specificity and in another preferred embodiment by sialidase with similar protein structure and/or by including present cell culture reagents such as calcium and/or magnesium 2+ cation and a non-glycoprotein, and preferably further containing other molecules of invention supporting the cells.

In a preferred embodiment the sialic acid amount reduction to be observed in analysis of the novel cells and/or characterizing the novel cell product with specific binder (antibody/lectin) reagents is within + or −5% units of the values for MAA and/or Mal 1 lectins and within + or −10% units for CHO antibody and within + or −25% units more preferably with 20% units of the sialic acid reduction values measured by lectin SNA as indicated in examples and preferably the cell is human mesenchymal cells.

The invention is in general directed to novel cell preparations according to the invention herein the modification levels measures by specific binder reagents (lectin or antibody) or mass spectrometry is within + or −50%, more preferably with + or −35, even more preferably within + or −25% of the given value (e.g. with 50% the range would be 5-15% for value 10% for e.g. value cell portion obtainable by fax or change of sialylation measured by alteration of glycan sialylation by mass spectrometry, preferably N-glycans sialylation).

The invention is directed also to the preferred enzyme reaction conditions selected from a group a buffer with similar pH, preferably with 1.5, more preferably with 1 pH unit, and similar salt concentrations and enzyme amounts (as Units defined in example and/or producer of the specific enzyme) within + or −75%, + or −50%, more preferably with + or −35, even more preferably within + or −25% of the given value. It is further realized that enzymes can be substituted by enzymes with higher specific activity. It is further realized that reaction can be optimized outside these ranges to obtain higher glycosylation modification levels, considering the viability of the cells, and enzyme amount can be added to 2, 3 or 5 fold, preferably using purified enzyme preparations and preferably removing the enzymes after reaction as defined in invention and copending application of applicants, e.g. PCT/FI2008/050015.

EXAMPLES

Example 1

Reaction Composition for Glycan Modification of Adherent Cells in the Presence of Divalent Cations Materials and Methods Cell detachment before enzymatic reactions: Bone marrow-derived mesenchymal stem cells (BM-MSC) in 70% confluency were detached with 0.25% trypsin/1 mM EDTA in $Ca^{2+}/Mg^{2+}$-free PBS (Invitrogen) or 0.05% trypsin/0.5 mM EDTA in $Ca^{2+}/Mg^{2+}$-free HBSS for 3 minutes. The trypsinization was inhibited by adding excess of α-MEM supplemented with 10% human serum albumin (HSA) (Albumin SPR, Sanquin, the Netherlands). Viability of the detached BM-MSCs was studied by Trypan blue exclusion. Immunophenotypic markers for MSC, binding of conjugated lectins and glycoform-specific antibodies for Lex and sLex glycan epitopes were analyzed by flow cytometry directly after trypsinization. The detached cells were centrifuged 300×g for 5 min, the supernatant was completely removed and 1×106 cells were resuspended in 300 μl enzyme reaction buffer composed of Minimum Essential Medium (MEM) cc medium supplemented with 0.5% HSA (reaction buffer control).

Enzymatic reactions: Glycosylation enzymes and sugar donors were added into the reaction buffer (Minimum Essential Medium (MEM) cc medium supplemented with 0.5% HSA) in the following concentrations: 50 or 100 mU rat recombinant ($Spodoptera$ $frugiperda$) α2,3-(N)-Sialyltransferase III (SAT) (Calbiochem) and 1 mg CMP-NeuAc, 15 or 30 mU human recombinant ($Spodoptera$ $frugiperda$) α1,3-Fucosyltransferase VI (FUT) (Calbiochem)+1 mg GDP-fucose, both SAT and FUT or 30 or 60 mU Sialidase (Neuramimidase) $C.$ $perfringens$ (α2, 3-6 specific). The original enzyme buffers were exchanged to the above mentioned reaction buffer or PBS (for Sialidase $C.$ $perfringens$) by dialysis. The BM-MSC cell suspensions were incubated in 24-well cell culture vessels for maximally 2 hours in +37° C. cell incubator, except in the double SAT+FUT reactions, wherein FUT and GDP-Fucose were added after one hour prior incubation with SAT. To prevent cells to re-adhere to each others or surface of culture vessels, the reactions were resuspended by mechanical pipetting using ART 1000E filter tips (Molecular BioProducts) with M1000 micropipette (Biohit) every 20 minutes during the incubation. Parallel reactions with cells only in the reaction buffer without the enzymes were always included in each experiment. The reactions were collected after 2 hours and cell viability and the number of cells were determined with trypan blue exclusion.

FACS analysis: For immunophenotypic characterization of MSC by flow cytometry (FACSAria, Becton Dickinson), antibodies against the following molecules were used (table x): CD90, CD73, CD105, HLA-ABC, CD34, CD45, CD14, CD19 and HLA-DR. Cell surface lectin binding profile of the BM-MSCs was studied with FITC- or biotin-conjugated MAA, SNA, RCA and ECA lectins before and after the enzymatic modifications of cell glycans. FITC-conjugated anti-streptavidin secondary antibody staining was done when biotin-conjugated lectins were used. The following Alexa 488-conjugated antiLex/sLex glycoform antibodies were also used for FACS analysis: CD15 (TG-1) Lex, PSGL-1 (core 2 O-glycan) sLex and sCD15 (sLex). $1\times10^5$ BM-MSCs were labelled in $Ca^{2+}$-free PBS supplemented with 2 mM EDTA and 1% BSA. Analysis was performed using the FACSDiva software (Beckton Dickinson).

Results

BM-MSC viability and immunophenotypic markers after in vitro glycomodification Viability of the BM-MSCs never fell below 98% and their cell surface expression of CD90, CD73, CD105, HLA-ABC, CD34, CD45, CD14, CD19 and HLA-DR remained unaltered after the α2,3-sialylation (SAT) or α1,3-fucosylation (FUT) reactions carried out in the reaction conditions described above (data not shown).

Effects of Glycomodifications on BM-MSC Cell Surface Binding of Plant Lectins and Lex and sLex Identifying Antibodies The glycomodifications were validated by FACS analysis of the binding of plant lectins and glycoform specific antibodies (Table 1) onto the cell surface. The results are summarized in FIG. 1.

A small increase in the percentage of MAA high-binding cells was noted after 2 h 50 mU α2,3-SAT reactions in the divalent cation containing buffer. Simultaneously, the RCAPE population staining was reduced with similar percentage values. The use of a higher amount of the enzyme, 100 mU for 2 h, for the sialylation produced a more robust increase in the MAA binding.

Figure 1:
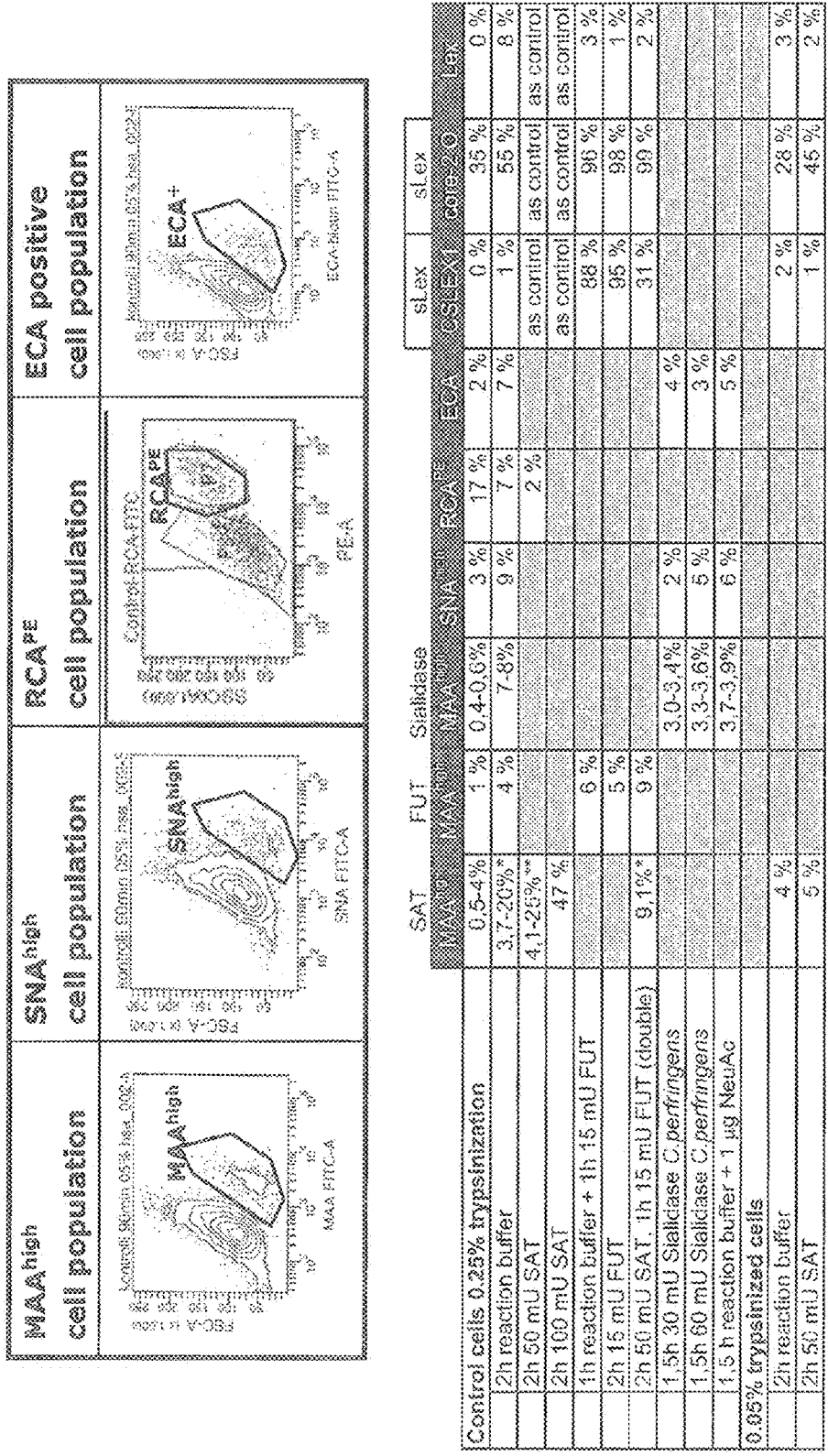
FIG. 1. Surface glycan profiles of BM-MSC demonstrated by FACS analysis of binding of plant lectins and glycoform-specific antibodies after α2,3-sialylation (SAT), α1,3-fucosylation (FUT), double SAT+ FUT and sialidase (*C. perfringens*) treatments. BM-MSC were detached with 0.25% or 0.05% trypsin. The control cells were analyzed directly after trypsinization. For the enzyme reactions, $1 \times 10^6$ cells were suspended in 300 μL of α-MEM+0.5% human serum albumin, i.e., containing divalent cations. The reactions were incubated for 1.5 or 2 hours at +37° C. and the reactions were resuspended every 20 minutes. The analyzed lectin populations are shown in the upper panel.

It is noteworthy that an increase in cell surface sialylation (both α2,3- and 6 linked sialic acids) directly after 0.25% trypsinization could be produced merely with the reaction buffer composition as compared to the control cells (FIG. 1). This was demonstrated by the MAA and SNA stainings, which were comparable to the decrease in the RCAPE staining. An increase in the staining intensity after incubating BM-MSC in the reaction buffer as compared to the control cells could also be observed for the core-2 sLex antibody, but not for the sLex/CSLEX1, or the CD90, CD105 and CD73 antibodies. The α1,3-fucosylation reaction was very efficient and >90% of the cells expressed the sLex/CSLEX1 epitope in the reaction composition and time chosen (FIG. 1, sLex/CSLEX1 antibody). Also the core-2 sLex antibody stained >90% of the cells after the α1,3-fucosylation reaction. A proceeding 1 h α2,3-sialylation inhibited the fucosylation reaction (FIG. 1).

There were no differences between the strong and mild trypsinization protocols before the 2 h reactions with or without enzyme concerning MAAhigh and core-2 O-glycan sLex antibody cell surface binding (FIG. 1). The sialidase reaction reduced the MAAhigh and SNAhigh lectin cell surface binding (FIG. 1). The sialidase reaction, however, also reduced ECA binding. Incubating the cells in the reaction buffer and excess NeuAc increased MAAhigh and especially SNAhigh binding (FIG. 1).

Example 2

Effect of Divalent Cations and Shear Stress to Aggregation and Morphology of Bone Marrow Mesenchymal Stem Cells (BM-MSCs)

Materials and Methods

BM-MSCs in 70% confluency were detached with 0.25% trypsin/1 mM EDTA in $Ca^{2+}/Mg^{2+}$-free PBS (Invitrogen) for 3 minutes. Trypsinization was inhibited by adding excess α-MEM+10% human serum albumin HSA (Albumin SPR, Sanquin, the Netherlands). The cell suspension was centrifuged, supernatant removed and $1.75 \times 10^6$ cells were resuspended in either 300 μl Minimum Essential Medium (MEM) cc medium supplemented with 0.5 HSA or $Ca^{2+}/Mg^{2+}$-free Hanks' Balanced Salt Solution (HBSS) supplemented with 0.1% HSA. The BM-MSC cell suspensions were incubated in 24-well cell culture vessels for 2 hours in +37° C. cell incubator. In a part of the culture wells, the cells were resuspended by mechanical pipetting through ART 1000E filter tips (Molecular BioProducts) attached to M1000 micropipette (Biohit) every 20 minutes during the incubation. Representative phase contrast microscope pictures of cells in suspension were taken at the beginning of the experiment and after 1 h and 2 h. The cells in suspension were collected at the end of the experiment and cell viability and the number of cells were determined by the trypan blue exclusion.

Results

Figure 2:
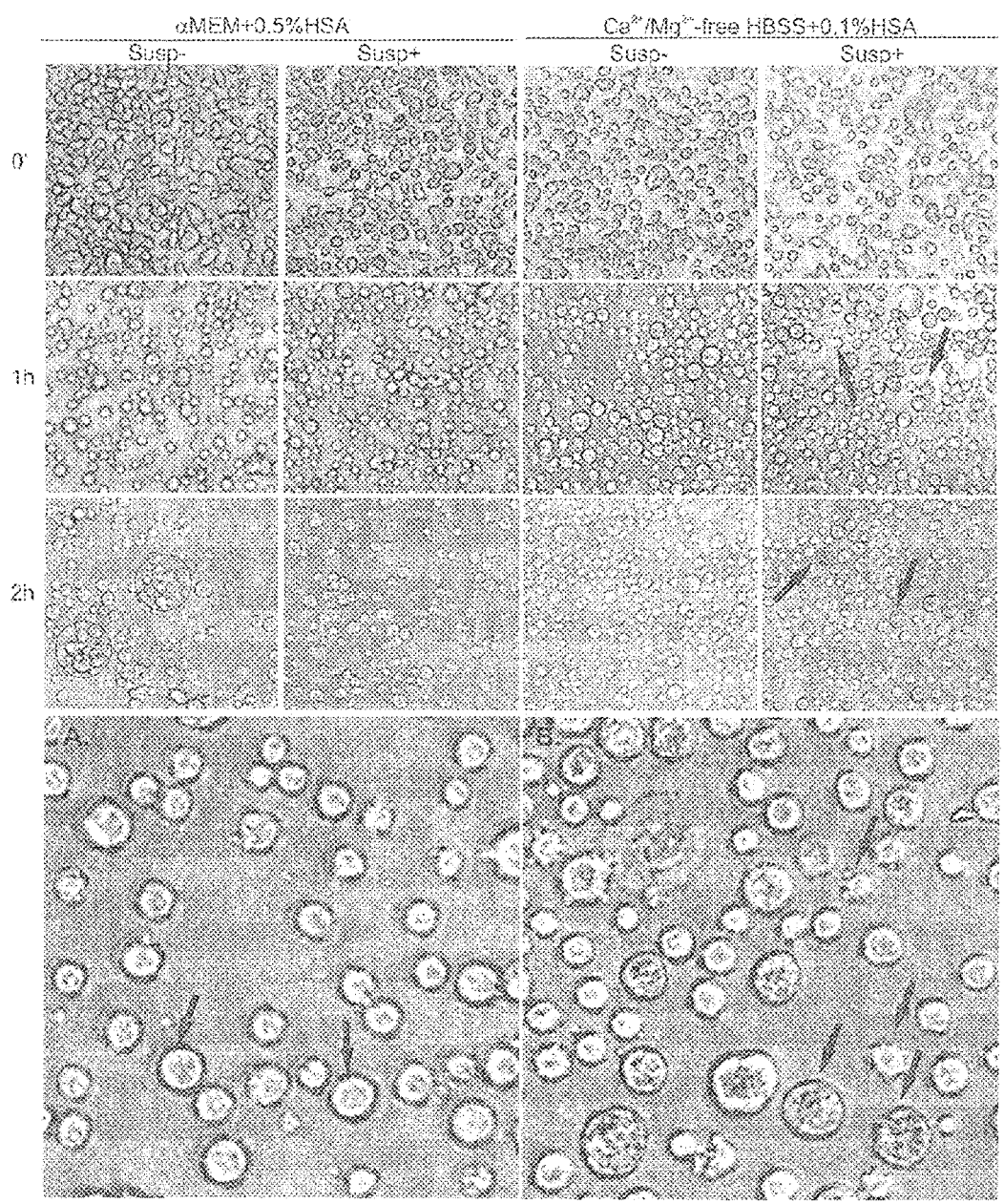
FIG. 2. Microscopic visualization of BM-MSC in different reaction buffer compositions (with and without divalent cations).

As shown in FIG. 2, BM-MSCs in suspension exhibited a heterogeneous cell population with cells of different sizes directly after trypsinization (time point 0'). After 1-2 hour incubation a change in cell morphology could be observed between cells in the α-MEM reaction buffer and $Ca^{2+}/Mg^{2+}$-free HBSS. The cell suspension in $Ca^{2+}/Mg^{2+}$-free HBSS contained more large, granular cells and small cells with bleb-like structures on their plasma membrane. The cells suspended in the $Ca^{2+}$- and $Mg^{2+}$-containing α-MEM reaction buffer contained more cells characterized by a round and clear, mononuclear cell-like morphology and intact plasma membranes (in FIG. 2, compare cells marked with arrows in panels). The cells aggregated more to each others in the α-MEM reaction buffer, but the aggregation could be inhibited by mechanical resuspension every 20 min. None of the reaction conditions could completely inhibit the cells from adhering to the cell culture vessel bottom as indicated in the total number of cells in suspension after 2 h incubation (Table 2). The adherence to cell culture bottom could also be inhibited by the sequential resuspension. There were a higher number of viable cells in the suspension phase, when the cells were incubated in the α-MEM+0.5% HSA reaction buffer than when incubated in the $Ca^{2+}/Mg^{2+}$-free HBSS (Table 2).

Example 3

Mild or Strong Trypsinization of BM-MSCs and the Inhibition of the Trypsinization Materials and Methods BM-MSC in 70% confluency were detached with either 0.25% trypsin/1 mM EDTA in $Ca^{2+}/Mg^{2+}$-free PBS (Invitrogen) or 0.05% trypsin/0.5 mM EDTA in $Ca^{2+}/Mg^{2+}$-free HBSS for 3 minutes. Trypsinization was inhibited by adding excess of either α-MEM+10% fetal calf serum (FCS) (Invitrogen) or α-MEM+10% human serum albumin (HSA) (Albumin SPR, Sanquin, the Netherlands). Cell viability and the number of cells were determined with trypan blue exclusion and representative phase contrast microscope pictures were taken with 10× objective.

Results

Both mild (0.05% trypsin) and 5× stronger (0.25% trypsin) trypsinization detached the cells into the unicellular cell suspension. Their viability in both cases were >98%. Equally viable cells could be produced if trypsinization was inhibited by adding 10% HSA or 10% FCS (FIG. 3). Human serum albumin can thus be used as a xenoantigen-free inhibitor of trypsinization.

Example 4

Glycan Controlled Enzyme

Glycosylation of commercial sialyl- or fucosyltransferase (Calbiochem Calif.) enzyme produced in insect cells is controlled by releasing the glycans, purifying the glycans and MALDI-TOF mass spectrometry (WO publication by the inventors, filed 11.7.2005). Potentially allergenic insect type glycans are observed and released by exoglycosidase enzymes as described for the insect glycans such as α-mannosidase, β-mannosidase α3- or α3/α6-fucosidases and hexosaminidase (such as Jack bean hexosaminidase), (WO publication by the inventors, filed 11.7.2005).

Glycosyltransferase-derived glycan structures. We detected that glycosylated glycosyltransferase enzymes can contaminate cells in modification reactions. For example, when cells were incubated with recombinant fucosyltransferase or sialyltransferase enzymes produced in *S. frugiperda* cells, N-glycosidase and mass spectrometric analysis of cellular and/or cell-associated glycoproteins resulted in detection of an abundant neutral N-glycan signal at m/z 1079, corresponding to $[M^+Na]^+$ ion of Hex3HexNAc2dHex1 glycan component (calc. m/z 1079.38). Typically, in recombinant glycosyltransferase treated cells, this glycan signal was more abundant than or at least comparable to the cells' own glycan signals, indicating that insect-derived glycoconjugates are a very potent contaminant associated with recombinant glycan-modified enzymes produced in insect cells. Moreover, this glycan contamination persisted even after washing of the cells, indicating that the insect-type glycoconjugate corresponding to or associated with the glycosyltransferase enzymes has affinity towards cells or has tendency to resist washing from cells. To confirm the origin of the glycan signal, we analyzed glycan contents of commercial recombinant fucosyltransferase and sialyltransferase enzyme preparations and found that the m/z 1079 glycan signal was a major N-glycan signal associated with these enzymes. Corresponding N-glycan structures, e.g. Manα3(Manα6)Manβ4GlcNAc(Fucα3/6)GlcNAc(β-N-Asn), have been described previously from glycoproteins produced in *S. frugiperda* cells (Staudacher et al., 1992; Kretzchmar et al., 1994; Kubelka et al., 1994; Altmann et al., 1999). As described in the literature, these glycan structures, as well as other glycan structures potentially contaminating cells treated with recombinant or purified enzymes, especially insect-derived products, are potentially immunogenic in humans and/or otherwise harmful to the use of the modified cells. It is concluded that glycan-modifying enzymes must be carefully selected for modification of human cells, especially for clinical use, not to contain immunogenic glycan epitopes, non-human glycan structures, and/or other glycan structures potentially having unwanted biological effects or in a preferred embodiment the glycan structures are removed or degraded to non-harmful ones.

Example 5

Enzymes and Conjugations

Conjugated Sialyltransferase and Fucosyltransferase Enzymes

The SAT and FUT enzymes were recombinant rat α2,3-N-sialyltransferase and recombinant α1,3-fucosyltransferase VI, respectively, expressed in *S. frugiperda* insect cells (Calbiochem).

Conjugation to Protein

The enzymes were biotinylated with N-hydroxysuccinimide-activated sulfo-biotin with aminocaproate spacer (sulfo-NHS-LC-biotin; Pierce). In the reaction, 5 µg of enzyme was incubated with either 0.65 nmol (about 5 times molar excess) or 6.5 nmol (about 50 times molar excess) biotinylation reagent in 50 µl of 50 mM HEPES buffer pH 8 at +4° C. for 2 hours. The reactions were stopped by adding a molar excess of Tris-HCl buffer pH 7.5.

Conjugation to Glycan

For periodate oxidation, the commercial glycerol-containing enzyme preparates were transferred into phosphate buffered saline solution with gel filtration chromatography in NAP-5 columns (Amersham-Pharmacia/GE Healthcare). Periodate oxidation of glycan chains was performed for 5 µg of either SAT or FUT in 40 µl of phosphate buffered saline (PBS) containing 8 mM $NaIO_4$, at +4° C. in the dark for 2-3 hours. Biotin conjugation to oxidized glycan chains was performed by adding 6.5 nmol (about 100 times excess) of biotin-amidohexanoic acid hydrazide (BAAH; Pierce) to the glycan-oxidized enzymes and incubating at +4° C. for 2-16 hours. The enzymes were isolated for subsequent use.

Activity Assays

Activity of conjugated enzymes was measured by performing standard reactions and comparing the amount of sialylated products to non-conjugated enzyme.

In a typical radiochemical SAT assay, 0.4 mU/µl enzyme was incubated with 1 mM CMP-[C-14]Neu5Ac and 0.5 mM acceptor glycoprotein (asialofetuin from Sigma-Aldrich) in 50 mM MOPS buffer pH 7.4 at +37° C. Aliquots from various time points were collected. Protein fraction was separated from the donor substrate by reversed phase solid-phase extraction and measured by liquid scintillation counting according to standard procedures. The amounts of radioactivity transferred to protein were compared. FUT activity was measured similarly using 0.04 mU/µl FUT, radiolabeled GDP-Fuc donor, and additionally 20 mM $MnCl_2$.

In a typical mass spectrometric assay, 0.2 mU/µl enzyme was incubated with 8 mM CMP-Neu5Ac and 4 mM LacNAc acceptor glycan (lacto-N-neotetraose) in 50 mM MOPS buffer pH 7.4 at +37° C., optionally containing 0.2 mg/ml albumin. Aliquots from various time points were collected. FUT activity was measured similarly using 0.05 mU/µl FUT, 8 mM GDP-Fuc donor, 4 mM acceptor, optionally with 20 mM MnCl2, and preferentially without albumin. The reaction level was analyzed by MALDI-TOF mass spectrometry using standard procedures, and relative signal intensities (correlating with corresponding relative molar amounts in the sample) of acceptor and product glycans were compared.

Enzymes in Cell-Optimized Liquid Compositions

SAT and FUT were optionally changed into cell-optimized solutions, preferentially α-MEM (Gibco/Invitrogen) and optionally using filtration concentration or dialysis. Optionally, human serum albumin (HSA; Finnish Red Cross Blood Service) was added, most commonly to concentration of 0.56% (5.6 mg/ml).

Conjugation Level Analysis

Conjugation level was analyzed by comparing molecular mass of non-conjugated and conjugated proteins in MALDI-TOF mass spectrometry using standard procedures.

Removal of Conjugated Enzyme

Biotinylated enzymes were removed from solution by contacting them with affinity matrix, preferentially with streptavidin-coated magnetic particles (Dynal). Removal of enzyme was visualized by SDS-PAGE and blotting with streptavidin-peroxidase conjugate and color reaction according to standard procedures.

Results

Protein-conjugated SAT and FUT, 5 times molar excess of biotinylation reagent:

SAT: on average 1.1 biotin unit was conjugated (+360 Da mass increase observed in MALDI-TOF MS) and comparable activity was retained as measured by the mass spectrometric assay;

FUT: on average 1.6 biotin unit was conjugated (+540 Da mass increase observed in MALDI-TOF MS) and comparable activity was retained as measured by the mass spectrometric assay.

Protein-conjugated SAT and FUT, 50 times molar excess of biotinylation reagent:
SAT: on average 3.4 biotin units were conjugated (+1170 Da mass increase observed in MALDI-TOF MS) and comparable activity was retained as measured by the mass spectrometric assay;
FUT: on average 4.3 biotin units were conjugated (+1450 Da mass increase observed in MALDI-TOF MS) and comparable activity was retained as measured by the mass spectrometric assay.

Glycan-conjugated glycosyltransferases:
The glycan-conjugated SAT showed similar activity as non-conjugated SAT when analyzed by the mass spectrometric assay. Mass spectrometric analysis of glycan conjugated sialyltransferase indicated high conjugation to glycans being about 5-10 biotins per enzyme.

Removal of Conjugated Enzymes from Solution

The biotin-conjugated proteins could be readily removed from solution by streptavidin-coated magnetic particles, as visualized for protein-biotin-conjugated SAT in FIG. 5. The results demonstrated that no enzyme could be detected in solution after the affinity-adsorption step, translating into nearly 100% efficiency, preferentially over 95% efficiency, and more preferentially over 99% efficiency in enzyme removal (FIG. 5).

Cell-Optimized Liquid Compositions

The SAT and FUT enzyme preparations in α-MEM and in α-MEM supplemented with HSA (0.56%) were active as measured by the mass spectrometric assay. Further, they showed good stability. For example, the HSA-containing SAT preparation in α-MEM was stable at +4° C. for over 16 days (in which time over 75% of original activity was retained as measured by the mass spectrometric assay). Further, FUT in HSA-containing α-MEM was active without adding $Mn^{2+}$ or other divalent cations to the standard α-MEM.

Bacterial Sialyltransferases in Cell Modification

The SAT enzymes were recombinant α2,3-sialyltransferase (JT-ISH-224 and JT-ISH-467) from *Photobacterium phosphonium* and α2,6-sialyltransferase (JT160) from *Photobacterium damselae* expressed in *E. coli* (Japan Tobacco Inc., Shizuoka, Japan).

Sialylation of Human Type Glycan Acceptors

In a typical assay reaction, 0.2 mU/μl enzyme was incubated with 8 mM CMP-Neu5Ac and 4 mM LacNAc acceptor glycan (lacto-N-neotetraose) in 20 mM Tris-HCl buffer pH 7.5 at +37° C., containing 0.2 mg/ml albumin and sodium chloride concentration of 150 mM (up to 0.5M was advised by the manufacturer). Aliquots were collected from several time points. The reaction level was analyzed by MALDI-TOF mass spectrometry using standard procedures, and relative signal intensities (correlating with corresponding relative molar amounts in the sample) of acceptor and product glycans were compared, and the enzymes were highly active towards the acceptor.

Novel Bacterial Enzymes in Cell-Optimized Liquid Compositions

SATs were optionally changed into cell-optimized solutions, preferentially α-MEM (Gibco/Invitrogen) and optionally using filtration concentration or dialysis. Human serum albumin (HSA; Finnish Red Cross Blood Service) was added to concentration of 0.2 mg/ml. The salt concentration was lowered to physiological salt contained within the α-MEM. The enzyme was highly active when analyzed by MALDI-TOF mass spectrometry with lacto-N-tetraose acceptor as described above.

Activity Compared to Mammalian Recombinant Enzyme

The activity of the enzymes was measured relative to equivalent nominal activities according to manufacturer's specifications. The bacterial enzyme was over 10 times more active than the recombinant mammal α2,3-N-sialyltransferase produced in insect cells by Calbiochem.

Neuraminidase or sialyltransferase is biotinylated as described in catalog of Pierce. Biotinylated neuraminidase or sialyltransferase enzyme is incubated with cells to modify the glycosylation of the target cells as described in the invention. The enzyme is removed by (strept)avidin magnetic beads (e.g. Miltenyi or Dynal) optionally with presence of neuraminic acid and or sialyltransferase acceptor (N-acetyllactosamine or lactose).

Example 6

Modification of BM-MSC Cells

Materials and Methods

Cells: Bone marrow-derived mesenchymal stem cells (BM-MSCs) were obtained as described by Leskelä et al. (2003). After initial culture establishment, BM-MSCs (<passage 10) were cultured in a humidified 5% $CO_2$ atmosphere at +37° C. in Minimum Essential Alpha-Medium (α-MEM) (Gibco) supplemented with 10% FCS, 20 mM Hepes, 10 ml/l penicillin/streptomycin and 2 mM L-glutamine.

α2,3-Sialyltransferase enzymatic modification: Cell culture media was collected for further analysis before the detachment. For the enzymatic modifications, BM-MSCs at 70-80% confluency were detached with PBS+2 mM Na-EDTA (Versene) for 30 min at +37° C. The number of detached cells were calculated in Bürker chamber and control (0-) cells were washed four times in cold $Ca^{2+}$-free PBS and frozen as cell pellets at −70° C. for mass spectrometric analysis. All centrifugation steps were performed at 300×g for 5 min. $1×10^6$ BM-MSCs were suspended in 300 μl reaction buffer consisting of α-MEM and 0.5% bovine serum albumin (BSA, >=99% pure). The enzymatic reactions were performed in 24-well cell culture plates in a humidified 5% CO2 atmosphere at +37° C. for either 2 or 4 hours. The reactions were controlled for attachment to the cell culture dish by suspending the cells every 30 min during the incubations. Control reactions were performed simultaneously with cells in reaction buffer only for 2 or 4 hours. The following enzymatic conditions were tested (i) 50 mU recombinant α2,3-(N)-Sialyltransferase (Calbiochem) and 1 mg CMP-Neu5Ac (donor), (ii) 10 mU (⅕) recombinant α2,3-(N)-Sialyltransferase and 1 mg CMP-Neu5Ac, (iii) 50 mU recombinant α2,3-(N)-Sialyltransferase and 0.2 mg (⅕) CMP-Neu5Ac, and (iv) 50 mU inactivated (boiled for 5 min and transferred directly to ice) recombinant α2,3-(N)-Sialyltransferase and 1 mg CMP-Neu5Ac. The enzymatic reactions were stopped by adding excess (2 ml) of cold $Ca^{2+}$-free PBS or $Ca^{2+}$-free PBS supplemented with 75 mM lactose to the reactions. Cell viability was determined by trypan blue staining and microscopic analysis in a Bürker chamber. The cells were centrifuged at 300×g for 5 min and washing was repeated additionally 3 times. After the last wash the cells were divided in two and half the cells were pelleted by centrifugation and frozen at −70° C. for further mass spectrometric N-glycan analysis and half the cells were used subsequently in flow cytometric analysis. The MALDI-TOF mass spectrometric analysis was performed for N-glycosidase F liberated N-glycans essentially as described (Hemmoranta H. et al., 2007. Exp. Hematol.).

Results

Cellular glycan modification with sialyltransferase: In the reaction, cell surface terminal N-acetyllactosamine (LN) units were sialylated as demonstrated by N-glycan structural analyses as follows. Reaction efficiency and level of terminal LN modification was followed by MALDI-TOF mass spectrometric profiling of the neutral N-glycan fraction. Three glycan signals were used as indicators of the reaction efficiency, namely at m/z 1622 (corresponding to hybrid-type N-glycan Hex6HexNAc3 Na-adduct signal, with documented one terminal LN unit), m/z 1663 (corresponding to complex-type N-glycan Hex5HexNAc4 Na-adduct signal, with documented two terminal LN units), and m/z 2028 (corresponding to complex-type N-glycan Hex6HexNAc5 Na-adduct signal, with documented three terminal LN units). These three indicator signals were good indicators for the overall sialylation level change. In the table below, reaction level is calculated by the equation:

$$100\% - 100\% * (I1622 + I1663 + I2028)a / (I1622 + I1663 + I2028)b$$

wherein Ix is relative proportion of glycan signal x (% of total glycan profile), "a" indicates signals after the enzyme reaction and "b" indicates those in the control reaction. The disappearance of sialic acid from the molecules indicated an increase of sialylation level. The glycan signal at m/z 1257 (control, corresponding to Na-adduct of Hex5HexNAc2 high-mannose type N-glycan) stayed between 5.7%-6.8% in all conditions, showing that modification was specific.

| | relative amount of glycan signals (% of total glycan profile): | | | |
|---|---|---|---|---|
| condition: | 1622 | 1663 | 2028 | reaction level (%) |
| 0-(cells in culture) | 1.33% | 2.10% | 0.40% | 3% |
| buffer control | 1.54% | 2.02% | 0.40% | 0% |
| inactivated enzyme | 1.34% | 1.94% | 0.48% | 5% |
| 2 h reaction | 0.77% | 0.32% | 0.00% | 72% |
| 4 h reaction | 0.52% | 0.32% | 0.00% | 79% |
| 1:5 donor | 0.89% | 0.54% | 0.00% | 64% |
| 1:5 enzyme | 0.95% | 0.67% | 0.00% | 59% |

The results indicated that:
1) an exogenous, functional enzyme was needed for an efficient reaction. This was indicated by negligible levels of the reaction with a heat-inactivated enzyme (5% reaction level), as compared to both the control cells (3%, by reference) and buffer control (0%).
2) the highest effective reaction level was about 80% (79%) in the 4 h optimized reaction conditions,
3) a 2 h reaction time (72%) was nearly as efficient as 4 h reaction (79%), however, a longer reaction time produced a higher reaction level,
4) a lower amount of either enzyme (1:5 enzyme) or donor substrate (1:5 donor) resulted in less efficient reactions, 59% and 64%, respectively, showing that the optimized reaction conditions were critical for an efficient removal of LN units from cells.

When the cell culture and reaction media were analyzed by the same method, it was additionally detected that glycoprotein components containing a LN group when added to the medium, were efficient substrates of the enzymatic modification, therefore competing with the cellular modification if added to the reaction solution.

Contamination with insect derived enzyme and its removal: m/z 1079, corresponding to sodium adduct ion of Hex3HexNAc2dHex1, a paucimannosidic insect N-glycan/low-mannose type human N-glycan. Below are results from mass spectrometric measurements of the relative amounts of m/z 1079 glycan signal in different reaction/wash conditions.

| | relative amount of m/z 1079 glycan signal (% of total glycan profile): | | |
|---|---|---|---|
| condition: | | Difference to control % | Relative difference to 4 h |
| buffer control | 0.75% | | |
| 4 h reaction | 1.45% | 0.70 | |
| inactivated enzyme | 1.48% | 0.73 | |
| 1:5 donor | 1.47% | 0.72 | |
| 1:5 enzyme | 1.09% | 0.34 | 49% |
| wash opt A | 0.84% | 0.09 | 12% |

The results indicated that:
1) low level of the m/z 1079 glycan signal were present in the cells before addition of the enzyme due to endogenous low-mannose N-glycans (0.75% relative amount in the "buffer control" condition),
2) all reaction conditions with full amount of enzyme resulted in contamination with insect-derived glycan (c. 1.5% relative amount in the "4 h reaction", "inactivated enzyme", and "1:5 donor" conditions),
3) a lower amount of added enzyme resulted in a lower level of contamination (1.1% relative amount in the "1:5 enzyme" condition),
4) 75 mM lactose included in the washing buffers resulted in efficient wash of the insect-derived glycan contamination (0.84% relative amount in the "wash opt A" condition), and
5) incomplete reaction may increase enzyme contamination (1.47% versus 1.45% in the "1:5 donor" and "4 h reaction" conditions, respectively).

Example 7

Production of a Tag Glyco-Conjugated Enzyme

Mammalian glycosyltransferase (e.g. β4-galactosyltransferase, bovine GalT1) is treated with α-sialidase, and β-galactosidase. Ketone modified Gal is transferred from ketone modified Gal-UDP to the terminal monosaccharide GlcNAc-residue by mutant galactosyltransferase as described in patent application by part of the inventors US2005014718 (included fully as reference) or by Qasba and Ramakrishman and colleagues US2007258986 (included fully as reference) or by using methods described in glycopegylation patenting of Neose (US2004132640, included fully as reference). The ketone is reacted with excess of amino-oxy-biotin (or hydrazide-biotin).

Example 8

Production of Cells

Cord Blood Mesenchymal Stem Cell Lines

Collection of umbilical cord blood. Human term umbilical cord blood (UCB) units were collected after delivery with informed consent of the mothers and the UCB was processed within 24 hours of the collection. The mononuclear cells (MNCs) were isolated from each UCB unit diluting the UCB 1:1 with phosphate-buffered saline (PBS) followed by Ficoll- Paque Plus (Amersham Biosciences, Uppsala, Sweden) density gradient centrifugation (400 g/40 min). The mononuclear cell fragment was collected from the gradient and washed twice with PBS.

Umbilical cord blood cell isolation and culture. CD45/ Glycophorin A (GlyA) negative cell selection was performed using immunolabeled magnetic beads (Miltenyi Biotec). MNCs were incubated simultaneously with both CD45 and GlyA magnetic microbeads for 30 minutes and negatively selected using LD columns following the manufacturer's instructions (Miltenyi Biotec). Both CD45/GlyA negative elution fraction and positive fraction were collected, suspended in culture media and counted. CD45/GlyA positive cells were plated on fibronectin (FN) coated six-well plates at the density of $1 \times 10^6/cm^2$. CD45/GlyA negative cells were plated on FN coated 96-well plates (Nunc) about $1 \times 10^4$ cells/well. Most of the non-adherent cells were removed as the medium was replaced next day. The rest of the non-adherent cells were removed during subsequent twice weekly medium replacements.

The cells were initially cultured in media consisting of 56% DMEM low glucose (DMEM-LG, Gibco, 40% MCDB-201 (Sigma-Aldrich) 2% fetal calf serum (FCS), 1× penicillin-streptomycin (both from Gibco). 1×ITS liquid media supplement (insulin-transferrin-selenium), 1× linoleic acid-BSA, 5×10-8 M dexamethasone, 0.1 mM L-ascorbic acid-2-phosphate (all three from Sigma-Aldrich). In later passages (after passage 7) the cells were also cultured in the same proliferation medium except the FCS concentration was increased to 10%.

Plates were screened for colonies and when the cells in the colonies were 80-90% confluent the cells were subcultured. At the first passages when the cell number was still low the cells were detached with minimal amount of trypsin/EDTA (0.25%/1 mM, Gibco) at room temperature and trypsin was inhibited with FCS. Cells were flushed with serum free culture medium and suspended in normal culture medium adjusting the serum concentration to 2%. The cells were plated about 2000-3000/cm2. In later passages the cells were detached with trypsin/EDTA from defined area at defined time points, counted with hematocytometer and replated at density of 2000-3000 cells/cm².

Bone Marrow-Derived Stem Cells.

Bone marrow (BM)-derived MSCs were obtained as described by Leskelä et al. (2003). Briefly, bone marrow obtained during orthopedic surgery was cultured in Minimum Essential Alpha-Medium (α-MEM), supplemented with 20 mM HEPES, 10% FCS, 1× penicillin-streptomycin and 2 mM L-glutamine (all from Gibco). After a cell attachment period of 2 days the cells were washed with $Ca^{2+}$ and $Mg^{2+}$ free PBS (Gibco), subcultured further by plating the cells at a density of 2000-3000 cells/cm² in the same media and removing half of the media and replacing it with fresh media twice a week until near confluence.

Flow cytometric analysis of mesenchymal stem cell phenotype.

Both UBC and BM derived mesenchymal stem cells were phenotyped by flow cytometry (FACSCalibur, Becton Dickinson). Fluorescein isothicyanate (FITC) or phycoerythrin (PE) conjugated antibodies against CD13, CD14, CD29, CD34, CD44, CD45, CD49e, CD73 and HLA-ABC (all from BD Biosciences, San Jose, Calif., CD 105 (Abcam Ltd., Cambridge, UK, and CD 133 (Miltenyi Biotec) were used for direct labeling. Appropriate FITC- and PE-conjugated isotypic controls (BD Biosciences) were used. Unconjugated antibodies against CD90 and HLA-DR (both from BD Biosciences) were used for indirect labeling. For indirect labeling FITC-conjugated goat anti-mouse IgG antibody (Sigma-Aldrich) was used as a secondary antibody.

The UBC derived cells were negative for the hematopoietic markers CD34, CD45, CD14 and CD133. The cells stained positively for the CD13 (aminopeptidase N), CD29 ((β-integrin), CD44 (hyaluronate receptor), CD73 (SH3), CD90 (Thy1), CD105 (SH2/endoglin) and CD 49e. The cells stained also positively for HLA-ABC but were negative for HLA-DR. BM-derived cells showed to have similar phenotype. They were negative for CD14, CD34, CD45 and HLA-DR and positive for CD13, CD29, CD44, CD90, CD105 and HLA-ABC.

Cell Harvesting for Glycome Analysis.

1 ml of cell culture medium was saved for glycome analysis and the rest of the medium removed by aspiration. Cell culture plates were washed with PBS buffer pH 7.2. PBS was aspirated and cells scraped and collected with 5 ml of PBS (repeated two times). At this point small cell fraction (10 µl) was taken for cell-counting and the rest of the sample centrifuged for 5 minutes at 400 g. The supernatant was aspirated and the pellet washed in PBS for an additional 2 times.

The cells were collected with 1.5 ml of PBS, transferred from 50 ml tube into 1.5 ml collection tube and centrifuged for 7 minutes at 5400 rpm. The supernatant was aspirated and washing repeated one more time. Cell pellet was stored at −70° C. and used for glycome analysis.

Biological Use of Novel Cells

The cells can be used for in vivo imaging trials and in animal models such as PET imagining e.g. as described in Min J J et al. (2006) Ann Nucl Med 20,(3) 165-70 or Kang W J et al. (J Nucl Med 47, 1295-1301).

Example 9

Modification of Adherent or Detached Stem Cells

Materials and Methods

Cells: Bone marrow-derived mesenchymal stem cells (BM-MSCs) line 168 were obtained as described by Leskelä et al. (2003). After initial culture establishment, BM-MSCs (<passage 10) were cultured in a humidified 5% $CO_2$ atmosphere at +37° C. in Minimum Essential Alpha-Medium (α-MEM) (Invitrogen) supplemented with 10% FCS, 20 mM Hepes, 10 ml/l penicillin/streptomycin and 2 mM L-glutamine.

α2,3-Sialyltransferase enzymatic modification: For the enzymatic modifications, BM-MSCs at 70-80% confluency were either detached with PBS+0.54 mM Na-EDTA (0.02% Versene) for 20 min at +37° C. or were washed once with PBS. The number of detached cells were calculated in Bürker chamber and control (sample Versene 0-) cells were washed four times in cold $Ca^{2+}$-free PBS and frozen as cell pellets at −70° C. for mass spectrometric analysis. All centrifugation steps were performed at 300×g for 5 min. 300 µl SAT reaction buffer consisting of α-MEM (Invitrogen), 0.5% human serum albumin (Albumin SPR, Sanquin), 50 mU rat recombinant α2,3-(N)-Sialyltransferase (SAT, Calbiochem) and 1 mg CMP-Neu5Ac (donor) was added to either adherent cells in one Ø10 cm cell culture vessel (sample α2,3SAT+Versene) or to detached cells in suspension from one Ø10 cm cell culture vessel transferred to a 24-well cell culture plate (sample Versene+α2,3SAT). The reactions were performed in a humidified 5% CO2 atmosphere at +37° for 2 hours. The cells in suspension were resuspended every 20 min during the incubation. The enzymatic reactions were stopped by adding excess of cold PBS. The adherent cells were subsequently detached as described previously. Cell viability was determined by Trypan blue exclusion and microscopic analysis in a Bürker chamber for all cells after modifications and detachment. The cells were centrifuged and washing with PBS was repeated additionally 3 times. The cells were finally pelleted by centrifugation and frozen at −70° C. for further mass spectrometric N-glycan analysis. The MALDI-TOF mass spectrometric analysis was performed for N-glycosidase F liberated N-glycans essentially as described (Hemmoranta H. et al., 2007. Exp. Hematol.).

Results

The results are presented in FIG. 6. Chosen cell surface terminal N-acetyllactosamine (LN) units were studied as proof of sialylation by N-glycan structural analyses (FIG. 6). Reaction efficiency and level of terminal LN modification was followed by MALDI-TOF mass spectrometric profiling of the neutral N-glycan fraction. The chosen terminal LN units are marked with red arrows in FIG. 6. The results clearly show that for the chosen terminal LN, α2,3-sialylation is more efficient if the cells are detached before the enzymatic reaction. The cell viability was not affected by the modifications as compared to the control (0-) cells.

Example 10

Optimal Modification Vessel and Applied Shear Force

The Isolation, Culture and Characterization of Human Cord Blood-Derived MSCs (UCBMSC)

Cord blood was collected in a multiple bag system containing 17 ml of citrate phosphate dextrose buffer (Cord Blood Collection System; Eltest, Bonn, Germany). Collections were performed at the Helsinki University Central Hospital, Department of Obstetrics and Gynecology, and Helsinki Maternity Hospital. All donors gave informed consent and the study protocol was approved by ethical review board of Helsinki University Central Hospital and the Finnish Red Cross Blood Service. Prior to the isolation of mononuclear cells, the anti-coagulated cord blood was diluted 1:2 with 2 mM EDTA-PBS. Mononuclear cells were isolated using Ficoll-Hypaque (Amersham Biosciences, Piscaway, N.J., USA) gradient centrifugation. $1 \times 10^6/cm^2$ mononuclear cells were plated on fibronectin (Sigma) coated tissue culture plates (Nunc) in proliferation medium consisting of minimum essential medium α(αMEM) with Glutamax (Gibco, Grand Island, N.Y., USA) and 10% fetal calf serum (FCS) (Gibco) supplemented with 10 ng/mL epidermal growth factor (EGF, Sigma), 10 ng/mL recombinant human platelet-derived growth factor (rhPDGF-BB; R&D Systems, Minneapolis, Minn., USA), 50 nM Dexamethasone (Sigma), 100 U/mL penicillin+100 µg/mL streptomycin (Invitrogen). The initial MSC line establishment was performed in a humidified incubator with hypoxic conditions (5% $CO_2$, 3% $O_2$ and 37° C.). Cells were allowed to adhere overnight and non-adherent cells were washed out with medium changes. Proliferation media was renewed twice a week. Established lines were passaged when almost confluent and replated at 1000-3000 cells/cm² in proliferation media in normoxic conditions (5% $CO_2$, 20% $O_2$ and 37° C.).

MSC Minimum Criteria Characterization

To ensure the MSC cell surface expression for critical MSC markers, established MSC lines were analyzed for their cell surface molecule expression by labeling with fluorochrome-conjugated monoclonal antibodies: allophycocyanin (APC)-conjugated CD13 (BD Pharmingen), phycoerythrin (PE)-conjugated CD14, CD19, CD34 and CD45 (BD Pharmingen), fluorescein isothiocyanate (FITC)-conjugated CD90 (clone 5E10, Stem Cell Technologies), FITC-CD105 (Abcam) and FITC-HLA-DR (BD Pharmingen). Appropriate FITC-, PE- and APC-conjugated isotypic controls (BD Biosciences) were used. Labeling was carried out in 1000 of phosphate buffered saline (PBS) with 0.5% ultra pure bovine serum albumin (BSA) on ice for 30 minutes. Flow cytometric analysis was performed on FACSAria (Becton Dickinson Biosciences) with a 488-nm blue laser for (PE and FITC) and a 633-nm red laser for (APC). Florescence was measured using 530/30-nm (FITC), 585/42-nm (PE) and 660/20-nm (APC) bandpass filters. Data were analyzed using FACSDiva software (BD Biosciences). Multipotent differentiation capacity was characterized by inducing differentiation. 4-5$^{th}$ passage cells were cultured in osteogenesis, chondrogenesis or adipogenesis inducing media up to 3 weeks. Differentiation capacity was evaluated with standard staining methods.

Enzymatic Cell Surface Glycomodification with Different Incubation Options

The incubation options tested are presented in Table 4. The incubation strategies were evaluated with and without an enzymatic modification, in this case α2,3-sialyltransferase III (SAT) modification (Calbiochem cat #566218, purification lot GF1061, activity 5.6 mU/µl) reaction for 2 hours together with CMP-NeuAc (Kyowa Hakko, Tokyo) donor. UCBMSC 391P cells were used in these studies in p4. α2,3-SATIII modifications were done with 100 mU enzyme and 1 mg CMP-Neu5Ac donor in 300 µl reaction buffer (αMEM+0.5% human serum albumin HSA)/0.5×10e6 cells.

Analysis of the Glycomodified Cells after Different Incubation Options

After the tested incubation options, cell viability was determined by Trypan blue staining for each sample. The cells were analyzed by flow cytometry for MSC minimum criteria cell characterization markers as described above and for conjugated MAA and MAL-1 plant lectin binding to determine the level of cell surface α2,3-sialylation (α2,3SA). 1 µl of the conjugated α2,3SA-binding lectins MAA-FITC (Ey laboratories) and MAL1-FITC (Vector laboratories, #FL-1311) was used per 1×10e5 cells with the same labeling protocol as described above for the MSC minimum criteria panel. Flow cytometric analysis was performed on FACSAria (Becton Dickinson Biosciences) with a 488-nm blue laser for (PE and FITC) and a 633-nm red laser for (APC). Florescence was measured using 530/30-nm (FITC), 585/42-nm (PE) and 660/20-nm (APC) bandpass filters. Data were analyzed using FACSDiva software (BD Biosciences).

Results and Discussion

Viability was not affected by any of the different incubation strategies (Table 4). Adherence and aggregation of cells can be reduced by using a conical tube instead of a cell culture dish well (plastic is different, surface area is different). Mechanical mixing by gentle pipetting every 30 min reduced adherence significantly (FIG. 7). Enzymatic glycomodification was most successful in a conical tube placed in a humidified cell incubator of tested options (Table 5).

Hypoxic (almost 0% $O_2$) conditions, i.e. cells in tube with closed cap, might quickly affect pH of the reaction buffer used and thus affect enzyme activity. However, buffer-induced alterations in cell surface sialylation levels are evident in hypoxic conditions (Table 5).

The roughest cell incubation strategy, condition #5 i.e. using a shaker at 150 rpm for 2 hours, seems to be too harsh since changes were seen in the cell surface expression of the MSC minimal criteria antigens (positive: CD13, CD44, CD49e, CD29, CD90, CD73, CD105, HLA-ABC; negative: HLA-DR, CD14, CD19, CD34, CD45). Some positive markers were less positive as compared to control cells and some negative markers started to appear on the cell surface, although viability with Trypan blue exclusion was >95% (Table 4). The results indicate that prolonged shaking might affect the level of multipotency.

As a consensus, an open conical tube placed in a humidified cell incubator with normoxic conditions and with mechanical mixing every 30 min is optimal for enzymatic glycomodification reactions.

Example 11

Human Serum Albumin (HSA) is an Optimal Supplement in Enzymatic Glycomodifications A. α2,3-Sialyltransferase Assay
Materials and Methods α2,3SAT (2 mU; Calbiochem) was incubated with lacto-N-neotetraose (LNnT) acceptor and 5 mM CMP-Neu5Ac at 37° C. in minimum essential medium α (αMEM)(Gibco, Grand Island, N.Y., USA) with 0.1% or without human serum albumin (Albumin SPR, Sanquin, the Netherlands). Reaction times were 2 hours and overnight. Aliquots of the reaction mixtures were subjected to size-exclusion chromatography on Superdex Peptide PC 3.2/30 column (GE Healthcare). The effluent was monitored with a UV detector at 214 nm and the amount of the reaction product Neu5Ac-LNnT was quantified by reference to monosaccharide standards (GlcNAc and Neu5Ac).

Results and Discussion

Size-exclusion chromatography of the aliquots from sialyltransferase assay indicated that α2,3SAT was capable of sialylating oligosaccharide acceptor LNnT in αMEM containing human serum albumin. Analysis of aliquots taken from 2 hour reaction showed that 0.9 nmol of reaction product Neu5Ac-LNnT was formed from 10 nmol of acceptor in αMEM containing albumin while the enzyme was totally inactive in αMEM without albumin. When the reaction was continued overnight, the product peak could still be detected only from reaction where albumin was present (FIG. 8).

B. Desialylation of Human Stem Cells: Comparison Between Human or Bovine Albumin Supplements in Reaction Buffer
The Isolation, Culture and Characterization of Human Cord Blood-Derived MSC (UCBMSC)

Cord blood was collected in a multiple bag system containing 17 ml of citrate phosphate dextrose buffer (Cord Blood Collection System; Eltest, Bonn, Germany). Collections were performed at the Helsinki University Central Hospital, Department of Obstetrics and Gynecology, and Helsinki Maternity Hospital. All donors gave informed consent and the study protocol was approved by ethical review board of Helsinki University Central Hospital and the Finnish Red Cross Blood Service. Prior to the isolation of mononuclear cells, the anti-coagulated cord blood was diluted 1:2 with 2 mM EDTA-PBS. Mononuclear cells were isolated using Ficoll-Hypaque (Amersham Biosciences, Piscaway, N.J., USA) gradient centrifugation. $1\times10^6/cm^2$ mononuclear cells were plated on fibronectin (Sigma) coated tissue culture plates (Nunc) in proliferation medium consisting of minimum essential medium α (αMEM) with Glutamax (Gibco, Grand Island, N.Y., USA) and 10% fetal calf serum (FCS) (Gibco) supplemented with 10 ng/mL epidermal growth factor (EGF, Sigma), 10 ng/mL recombinant human platelet-derived growth factor (rhPDGF-BB; R&D Systems, Minneapolis, Minn., USA), 50 nM Dexamethasone (Sigma), 100 U/mL penicillin +100 µg/mL streptomycin (Invitrogen). The initial MSC line establishment was performed in a humidified incubator with hypoxic conditions (5% $CO_2$, 3% $O_2$ and 37° C.). Cells were allowed to adhere overnight and non-adherent cells were washed out with medium changes. Proliferation media was renewed twice a week. Established lines were passaged when almost confluent and replated at 1000-3000 cells/cm² in proliferation media in normoxic conditions (5% $CO_2$, 20% $O_2$ and 37° C.).

MSC Minimum Criteria Characterization

To ensure the MSC cell surface expression for critical MSC markers, established MSC lines were analyzed for their cell surface molecule expression by labeling with fluorochrome-conjugated monoclonal antibodies: allophycocyanin (APC)-conjugated CD13 (BD Pharmingen), phycoerythrin (PE)-conjugated CD14, CD19, CD34 and CD45 (BD Pharmingen), fluorescein isothiocyanate (FITC)-conjugated CD90 (clone 5E10, Stem Cell Technologies), FITC-CD105 (Abcam) and FITC-HLA-DR (BD Pharmingen). Appropriate FITC-, PE- and APC-conjugated isotypic controls (BD Biosciences) were used. Labeling was carried out in 1000 of phosphate buffered saline (PBS) with 0.5% ultra pure bovine serum albumin (BSA) on ice for 30 minutes. Flow cytometric analysis was performed on FACSAria (Becton Dickinson Biosciences) with a 488-nm blue laser for (PE and FITC) and a 633-nm red laser for (APC). Fluorescence was measured using 530/30-nm (FITC), 585/42-nm (PE) and 660/20-nm (APC) bandpass filters. Data were analyzed using FACSDiva software (BD Biosciences). Multipotent differentiation capacity was characterized by inducing differentiation. 4-5$^{th}$ passage cells were cultured in osteogenesis, chondrogenesis or adipogenesis inducing media up to 3 weeks. Differentiation capacity was evaluated with standard staining methods.

Desialylation Reactions

Human UCBMSCs were desialylated for 2 hours in conical tubes in a 37° C. cell incubator with 200 mU *Vibrio cholerae* neuraminidase per 1×10e6 cells in 600 µl αMEM+0.5% human serum albumin (HSA) (Albumin SPR, Sanquin) or ultrapure (>99%) bovine serum albumin (BSA) (Sigma). The cells were mixed by mechanical suspension every 30 min.

Validation of Glycomodification by Flow Cytometry

MSC minimum criteria characterization was performed as described above. Cell surface lectin binding profile was studied with FITC- or biotin conjugated MAA, MAL-1 or SNA plant lectins before and after enzymatic glycomodifications. FITC-conjugated streptavidin secondary antibody staining was done when using biotin-conjugated lectins. The following Lewis X (Lex)/sialyl Lewis X (sLex) glycoform specific antibodies were also used: CD15 (TG-1) for Lex (BD Pharmingen), PSGL-1 (core 2 O-glycan) for sLex (R&D Systems) and CD15s for sLex (BD Pharmingen). $1\times10^5$ cells were labeled in $Ca^{2+}$-free PBS supplemented with 0.5-1% BSA. Flow cytometric analysis was performed on FACSAria (Becton Dickinson Biosciences) with a 488-nm blue laser for (PE and FITC) and a 633-nm red laser for (APC). Analysis was performed using the FACSDiva software (Beckton Dickinson)

Results and Discussion

The results are presented in Table 6. Control1 indicates cells at time point 0, analyzed directly after trypsinization. Control2 indicates reaction buffer incubated cells with no enzyme. Desialylation for 2 hours with *V. cholera* sialidase efficiently reduces binding of both the α2,3-sialic acid binding lectins MAA and MAL1 and α2,6-sialic acid binding lectin SNA with an over 20% more effective result in reactions supplemented with HSA than BSA (Table 6). However, the binding of the sLex-binding glycoform antibody CHO-131 is reduced more when the reaction has been supplemented with BSA as compared with HSA. Interestingly, the BSA supplemented reaction induces more spontaneous changes in cell surface α2,3-sialylation levels as studied by MAA and MAL lectin binding (Table 6, control1 versus control2). This also indicates that HSA stands out as a better supplement than BSA, since the levels of "spontaneous" cell surface sialylation induced by buffer only are more moderate in HSA supplemented reactions. In conclusion, the results clearly indicate than HSA is a superior choice as a supplement in glycomodification reactions of human stem cell. Supplementing the glycomodification buffer with HSA also gives a xeno-free glycomodification buffer for stem cells.

Example 12

MSC Optimal Suspension Density

Materials and Methods

Human umbilical cord blood-derived mesenchymal stem cells (UCBMSC) were detached with TrypLE (Invitrogen) and incubated as suspension cells in αMEM+0.5% human serum albumin (HSA) (Albumin SPR, Sanquin, the Netherlands) either with 0.5×10e6 (1.7×10e6 cells/ml) or 1×10e6 cells/300 µl (3.3×10e6 cells/ml) cell densities. The cells were kept in conical tubes with open caps in a humidified cell incubator for 2 hours with a mechanical mixing by pipetting every 30 min. At the end of the incubation the cells were transferred to cell culture dishes and were photographed by phase contrast microscopy.

Results and Discussion

FIG. 9 demonstrates clearly that a suspension cell density of 1×10e6 UCBMSCs in 300 (3.3×10e6/ml) is too high for UCBMScs since a lot of small cell aggregates are formed although repeated mechanical mixing. An optimal cell density seems to be 0.5×10e6 UCBMSCs cells in 300 µl (1.7×10e6/ml) as demonstrated in FIG. 10. It is noteworthy that bone marrow-derived MSCs (BMMSCs) can tolerate more dense suspension incubations than UCBMSCs.

Example 13

Mild Cell Dissociation Preceding Enforced Enzymatic Glycomodifications

Materials and Methods

Human bone marrow-derived mesenchymal stem cells (BMMSC) (168 p'7) and human umbilical cord blood-derived mesenchymal stem cells (UCBMSC) (391P p4) were detached from culture plates with either porcine Trypsin-0.25% EDTA (Gibco Invitrogen) or TrypLE Express (Gibco Invitrogen, #12605-010) according to the manufacturer's instructions. The cell detachment process was observed by microscopy and stopped with complete culture media when complete. Detached cells were analyzed by flow cytometry by staining 1×10e5 cells in PBS (pH 7.2) and 0.3% BSA with 1 µl of the conjugated plant lectins MAA-FITC, MAL1-biotin (+streptavidin-FITC secondary antibody staining) and SNA-FITC for 30 min on ice. Flow cytometric analysis was performed on FACSAria (Becton Dickinson Biosciences) with a 488-nm blue laser for (PE and FITC) and a 633-nm red laser for (APC). Fluorescence was measured using 530/30-nm (FITC), 585/42-nm (PE) and 660/20-nm (APC) bandpass filters. Data were analyzed using FACSDiva software (BD Biosciences).

Results and Discussion

Standard porcine Trypsin-0.25% EDTA dissociation of MSCs was compared to TrypLE Express (Invitrogen) dissociation. Tryple Express is a recombinant enzyme derived from microbial fermentation, formulated in D-PBS with 1 mM EDTA and offers an improved stability, lower cost and animal-free, protease-free origin compared to standard porcine trypsin. According to the manufacturer, the use of porcine trypsin or TrypLE is similar and cell detachment equal. In our experiments, TrypLE detachment could be performed in 4 minutes, working similar to porcine trypsin, and the cell viability after detachment was very high with both reagents. The lectin labeling of UCBMSC was similar after porcine Trypsin vs. Tryple detachment (FIG. 11). BMMSC had higher MAL-1 and SNA binding after TrypLe detachment, suggesting possibly better preservation of cell surface sialic acid glycostructures on cell surface proteins. In conclusion, TrypLE preserves the cell surface sialylation levels at least as well as standard porcine trypsin and due to the other benefits of TrypLE Express, TrypLE Express stands out as an excellent choice for mild MSC cell dissociation preceding subsequent in vitro glycomodifications.

Example 14

Flow Cytometric Analysis Platform for Cell Surface Sialyl- and Sialyl-Fucosyl-Modifications A flow cytometry-based platform for fast and minimum sample consuming validation of the success of enforced in vitro glycomodifications was developed, especially for changes in cell surface levels of α2,3-sialylation and α1,3-fucosylation. In the absence of validated antibodies against sialic acids, the flow cytometric analyses were based on labeling with conjugated plant lectins (Table 7). The specificity of MAA-lectins, which should only recognize α2,3-linked sialic acid, varies remarkably between different manufacturers and conjugations, thus binding of several MAA lectins were compared and studied thoroughly with serial dilutions. Similarly, other sialic acid recognizing lectins SNA and LFA and terminal galactose recognizing ECA were examined. The secondary label streptavidin-FITC (eBiosciences, #11-4317) was used with biotin-conjugated lectins. α1,3-fucosylated glycan structures are validated with the following antibodies (also presented in Table 8): PSGL-1, clone CHO131 (GF526/VPU037) (R&D systems), CD15/TG-1 (GF525) (abcam), CD15s/CSLEX1 (VPU020) (BD Pharmingen), HECA-452 (CLA) (BD Pharmingen #555947). The cells were fixed in 0.5% paraformaldehyde (PFA) before stainings with plant lectins to avoid biological effects of the lectins. All stainings were performed with PBS (pH 7.2)+0.5% BSA for 30 minutes on ice and with appropriate subsequent secondary antibody stainings as needed.

Example 15

Efficient Desialylation Protocol of Stem Cells

The Isolation, Culture and Characterization of Human Cord Blood-Derived MSC (UCBMSC)

Cord blood was collected in a multiple bag system containing 17 ml of citrate phosphate dextrose buffer (Cord Blood Collection System; Eltest, Bonn, Germany). Collections were performed at the Helsinki University Central Hospital, Department of Obstetrics and Gynecology, and Helsinki Maternity Hospital. All donors gave informed consent and the study protocol was approved by ethical review board of Helsinki University Central Hospital and the Finnish Red Cross Blood Service. Prior to the isolation of mononuclear cells, the anti-coagulated cord blood was diluted 1:2 with 2 mM EDTA-PBS. Mononuclear cells were isolated using Ficoll-Hypaque (Amersham Biosciences, Piscaway, N.J., USA) gradient centrifugation. $1\times10^6/cm^2$ mononuclear cells were plated on fibronectin (Sigma) coated tissue culture plates (Nunc) in proliferation medium consisting of minimum essential medium α (αMEM) with Glutamax (Gibco, Grand Island, N.Y., USA) and 10% fetal calf serum (FCS) (Gibco) supplemented with 10 ng/mL epidermal growth factor (EGF, Sigma), 10 ng/mL recombinant human platelet-derived growth factor (rhPDGF-BB; R&D Systems, Minneapolis, Minn., USA), 50 nM Dexamethasone (Sigma), 100 U/mL penicillin +100 µg/mL streptomycin (Invitrogen). The initial MSC line establishment was performed in a humidified incubator with hypoxic conditions (5% $CO_2$, 3% $O_2$ and 37° C.). Cells were allowed to adhere overnight and non-adherent cells were washed out with medium changes. Proliferation media was renewed twice a week. Established lines were passaged when almost confluent and replated at 1000-3000 cells/$cm^2$ in proliferation media in normoxic conditions (5% $CO_2$, 20% $O_2$ and 37° C.).

MSC Minimum Criteria Characterization

To ensure the MSC cell surface expression for critical MSC markers, established MSC lines were analyzed for their cell surface molecule expression by labeling with fluorochrome-conjugated monoclonal antibodies: allophycocyanin (APC)-conjugated CD13 (BD Pharmingen), phycoerythrin (PE)-conjugated CD14, CD19, CD34 and CD45 (BD Pharmingen), fluorescein isothiocyanate (FITC)-conjugated CD90 (clone 5E10, Stem Cell Technologies), FITC-CD105 (Abcam) and FITC-HLA-DR (BD Pharmingen). Appropriate FITC-, PE- and APC-conjugated isotypic controls (BD Biosciences) were used. Labeling was carried out in 1000 of phosphate buffered saline (PBS) with 0.5% ultra pure bovine serum albumin (BSA) on ice for 30 minutes. Flow cytometric analysis was performed on FACSAria (Becton Dickinson Biosciences) with a 488-nm blue laser for (PE and FITC) and a 633-nm red laser for (APC). Fluorescence was measured using 530/30-nm (FITC), 585/42-nm (PE) and 660/20-nm (APC) bandpass filters. Data were analyzed using FACSDiva software (BD Biosciences). Multipotent differentiation capacity was characterized by inducing differentiation. 4-$5^{th}$ passage cells were cultured in osteogenesis, chondrogenesis or adipogenesis inducing media up to 3 weeks. Differentiation capacity was evaluated with standard staining methods.

Desialylation and Validation of Glycomodification

UCBMSCs (391P p6) were desilylated with 200 mU Vibrio cholerae sialidase/0.5×10e6 in 300 µl of αMEM Glutamax +0.5% human serum albumin (HSA) or 0.5% bovine serum albumin (BSA) for 2 h at 37° C. with mixing by pipetting every 30 min. Desialylation was stopped by adding excess reaction buffer and centrifugation. Cell surface lectin binding profile of the UCBMSCs was studied with FITC- or biotin conjugated MAA, MAL-1 or SNA lectins before and after enzymatic glycomodifications. FITC-conjugated streptavidin secondary antibody staining was done when using biotin-conjugated lectins. Sialic acid-dependent binding of the sLex glycoform antibody CHO-131 (PSGL-1 core 2 o-glycan) was also used together with appropriate conjugated secondary antibody. $1\times10^5$ BM-MSC:s were labeled per in $Ca^{2+}$-free PBS supplemented with 1% BSA. Analysis was performed using the FACSDiva software (Beckton Dickinson)

Results and Discussion

Desialylation of CB MSCs (391P p6) for 2 h in αMEM Glutamax+0.5% HSA showed significant reduction of MAA, MAL1, SNA and CHO131 (VPU037) binding (FIG. 11). Desialylation was more efficient in αMEM+0.5% HSA than αMEM+0.5% BSA (FIG. 11). CHO131 (VPU037) staining was lower in cells desilylated in aMEM Glutamax+0.5% BSA. The difference in desialylation between incubation media correlates with reaction buffer-induced MAA and MAL1 staining that is significantly higher in αMEM supplemented with 0.5% BSA. Desialylation using Vibrio cholerae sialidase was significantly more efficient than desialylation with Clostridium perfringens sialidase.

Example 16

Cell Surface Enzymatic Modification of Mesenchymal Stem Cells in Different Cell Culture Media Materials and Methods The Isolation, Culture and Characterization of Human Cord Blood-Derived MSC (UCBMSC)

Cord blood was collected in a multiple bag system containing 17 ml of citrate phosphate dextrose buffer (Cord Blood Collection System; Eltest, Bonn, Germany). Collections were performed at the Helsinki University Central Hospital, Department of Obstetrics and Gynecology, and Helsinki Maternity Hospital. All donors gave informed consent and the study protocol was approved by ethical review board of Helsinki University Central Hospital and the Finnish Red Cross Blood Service. Prior to the isolation of mononuclear cells, the anti-coagulated cord blood was diluted 1:2 with 2 mM EDTA-PBS. Mononuclear cells were isolated using Ficoll-Hypaque (Amersham Biosciences, Piscaway, N.J., USA) gradient centrifugation. $1\times10^6/cm^2$ mononuclear cells were plated on fibronectin (Sigma) coated tissue culture plates (Nunc) in proliferation medium consisting of minimum essential medium α (αMEM) with Glutamax (Gibco, Grand Island, N.Y., USA) and 10% fetal calf serum (FCS) (Gibco) supplemented with 10 ng/mL epidermal growth factor (EGF, Sigma), 10 ng/mL recombinant human platelet-derived growth factor (rhPDGF-BB; R&D Systems, Minneapolis, Minn., USA), 50 nM Dexamethasone (Sigma), 100 U/mL penicillin +100 µg/mL streptomycin (Invitrogen). The initial MSC line establishment was performed in a humidified incubator with hypoxic conditions (5% $CO_2$, 3% $O_2$ and 37° C.). Cells were allowed to adhere overnight and non-adherent cells were washed out with medium changes. Proliferation media was renewed twice a week. Established lines were passaged when almost confluent and replated at 1000-3000 cells/$cm^2$ in proliferation media in normoxic conditions (5% $CO_2$, 20% $O_2$ and 37° C.).

MSC Minimum Criteria Characterization

To ensure the MSC cell surface expression for critical MSC markers, established MSC lines were analyzed for their cell surface molecule expression by labeling with fluorochrome-conjugated monoclonal antibodies: allophycocyanin (APC)-conjugated CD13 (BD Pharmingen), phycoerythrin (PE)-conjugated CD14, CD19, CD34 and CD45 (BD Pharmingen), fluorescein isothiocyanate (FITC)-conjugated CD90 (clone 5E10, Stem Cell Technologies), FITC-CD105 (Abcam) and FITC-HLA-DR (BD Pharmingen). Appropriate FITC-, PE- and APC-conjugated isotypic controls (BD Biosciences) were used. Labeling was carried out in 1000 of phosphate buffered saline (PBS) with 0.5% ultra pure bovine serum albumin (BSA) on ice for 30 minutes. Flow cytometric analysis was performed on FACSAria (Becton Dickinson Biosciences) with a 488-nm blue laser for (PE and FITC) and a 633-nm red laser for (APC). Fluorescence was measured using 530/30-nm (FITC), 585/42-nm (PE) and 660/20-nm (APC) bandpass filters. Data were analyzed using FACSDiva software (BD Biosciences). Multipotent differentiation capacity was characterized by inducing differentiation. 4-$5^{th}$ passage cells were cultured in osteogenesis, chondrogenesis or adipogenesis inducing media up to 3 weeks. Differentiation capacity was evaluated with standard staining methods.
α2,3-Sialylation in Different Cell Culture Media The following reaction buffers were tested: a) minimum essential medium α (αMEM) (Gibco, Grand Island, N.Y., USA)+0.5% human serum albumin (HSA) (Albumin SPR, Sanquin, the Netherlands), b) xeno-free StemPro MSC SFM (Invitrogen) supplemented with 0.1% StemPro SFM XF (Invitrogen) and c) $Ca^{2+}/Mg^{2+}$-free Hank's balanced salt solution (HBSS) +2 mM Hepes +0.1% HSA (Sackstein et al. Nature Genetics 2008). The incubation strategies were evaluated with and without an enzymatic modification, in this case α2,3-sialyltransferase III (SAT) modification (Calbiochem cat #566218) reaction for 2 hours together with CMP-NeuAc (Kyowa Hakko, Tokyo) donor. α2,3-SATIII modifications were done with 100 mU enzyme and 1 mg CMP-Neu5Ac donor in 300 μl reaction buffer/0.5×10e6 cells. The incubation time was set to 2 h or 40 min for the HBSS buffer version (Sackstein et al. Nature Genetics 2008). Incubations were performed in 15 ml conical tubes (cap open) in +37° C. incubator with mechanical mixing by pipetting every 30 minutes.

Analysis of the Glycomodified Cells

After the tested incubation options, cell viability was determined by Trypan blue staining for each sample. The cells were analyzed by flow cytometry for MSC minimum criteria cell characterization markers as described above and for conjugated MAA, MAL-1 and SNA plant lectin binding to determine the levels of cell surface α2,3 and α2,6-sialylation. 1 μl of the conjugated lectins were used per 1×10e5 cells with the same labeling protocol as described above for the MSC minimum criteria panel. Flow cytometric analysis was performed on FACSAria (Becton Dickinson Biosciences) with a 488-nm blue laser for (PE and FITC) and a 633-nm red laser for (APC). Fluorescence was measured using 530/30-nm (FITC), 585/42-nm (PE) and 660/20-nm (APC) bandpass filters. Data were analyzed using FACSDiva software (BD Biosciences).

Results and Discussion

After 2 h incubation, >95% viability (Trypan blue staining) was detected in each incubation buffer. An increase in cell surface α2,3-sialylation levels after enforced α2,3-sialylation with α2,3-sialyltransferase III (SAT) was highest in αMEM+0.5% HSA reaction buffer (Table 9). However, an increase in cell surface α2,3-sialylation was also evident in StemPro MSC XF buffer (Table 9). Incubation related increase of MAA-FITC and MAL1-FITC lectin binding was highest in StemPro MSC XF+0.1% StemPro SFM XF supplements and very low in 40 min incubation in HBSS buffer.

Example 17

Targeting of Stem Cells to Bone Marrow by Glycomodification

Materials and Methods
Cells, Labeling, Glycomodification and Validation
Bone Marrow (BM) Derived Mesenchymal Stem Cells (MSC)

BMMSC:s were obtained as described by Leskelä et al. (2003). Briefly, bone marrow-derived mononuclear cells were cultured in Minimum Essential Alpha-Medium (αMEM) supplemented with 20 mM HEPES, 10% fetal calf serum, penicillin-streptomycin and 2 mM L-glutamine (all from Gibco). After a cell attachment period of 2 days the cells were washed with PBS, subcultured further by plating the cells at a density of 2000-3000 cells/cm² in the same media and replacing the medium twice a week until near confluence. The cells used in the example were between passage 2-5.

Cell Labeling for In Vivo Tracking

BMMSCs were detached with 0.25% trypsin/1 mM EDTA in $Ca^{2+}/Mg^{2+}$-free PBS (Invitrogen) for 3 minutes. The trypsinization was inhibited by adding excess of complete culture media. Cell viability and cell amounts were determined with trypan blue exclusion. The cells were metabolically labelled with 10 MBq $^3$H-2-deoxy-D-glucose ([$^3$H]-2DG) per 1×10⁶ cells or labelled with Tc99-HMPAO. Labeling efficiency was determined by measuring radioactivity of the supernatants in every step of the labeling protocols and aliquots of the labelled cells or the final cell pellets. The $^3$H-2-deoxy-D-glucose ([$^3$H]-2DG) metabolic labeling protocol yielded a specific activity of 6×10⁶ cpm/1×10⁶ cells.

Enforced α1,3-Fucosylation of BMMSCs

The labeled cells were recounted after the labeling procedure and cell-specific standard curves with specific cell amounts were prepared for subsequent radioactivity measurements. The rest of the cells were centrifuged 300×g for 5 min, the supernatant was completely removed and 1×106 cells were resuspended in 300 μl enzyme reaction buffer composed of αMEM supplemented with 0.5% human serum albumin (HSA) (Albumin SPR, Sanquin, the Netherlands). 1×10e6 cells were enzymatically cell surface α1,3-fucosylated with 15 mU human recombinant (*Spodoptera frugiperda*) α1,3-Fucosyltransferase VI (FUTVI) (Calbiochem) and 1 mg GDP-fucose in 600 μl reaction buffer for 1-2 hours at +37° C. The original FUTVI enzyme storage buffer was exchanged to the reaction buffer and activity examined before the experiment. To prevent cell aggregation or cell attachment to the modification vessel, the reactions were mixed by mechanical pipetting every 30 minutes during the incubation. Parallel reactions with cells only in the reaction buffer without enzymes were always included in each experiment and used as control cells in the subsequent in vivo experiments. The enforced enzymatic α1,3-fucosylation was stopped by adding excess volume of reaction buffer and washing the cells twice with reaction buffer. Aliquotes were taken from the cell reactions to monitor cell viability by Trypan blue exclusion and for validation of the success of the applied enzymatic glycomodification by flow cytometry.

Validation of Glycomodifications

The anti-Lex/sLex glycoform antibodies used for FACS analysis were: CHO-131 (PSGL-1 sLex on core II O-glycans, R&D Systems), CSLEX (CD15s, BD Pharmingen), FITC-HECA 452 (CLA, BD Pharmingen) and TG-1 (CD15, abcam). 1×10⁵ 0.5% PFA fixed BMMSCs were labelled with 3 μl of unconjugated CHO-131, CSLEX and TG-1 antibodies and 2 μl of FITC-conjugated HECA 452 antibody in $Ca^{2+}$-free PBS supplemented with 0.5% BSA for 30 minutes on ice and protected from light. Alexa-Fluor 488 conjugated goat anti-mouse IgG (Molecular Probes) was used in 1:500 dilution for secondary antibody stainings for the unconjugated primary antibodies for 20 min on ice protected from light. The samples were washed in excess PBS+0.5% BSA and analyzed with FACSAria (Beckton Dickson) flow cytometer. Analysis was performed using the FACSDiva software (Beckton Dickinson).

Animals and In Vivo Biodistribution Detection of Labelled Stem Cells

Adult (7-10 weeks) male (with [$^3$H]-2DG labelled cells) or female (with Tc99-HMPAO labelled cells), age-matched Hsd:Athymic Foxn1nu (Harlan) mice were used in the in vivo experiments. The acclimatization period was always at least 7 days before the experiments. The animal room temperature was 21±2° C. and humidity was between 40-60%. Lightning was artificial, 12 h light and 12 h dark. The mice were provided with irradiated fodder and normal tap water ad libitum. No formal randomization or grouping was done. Animals were randomly allocated to the study groups. The cells were centrifuged and resuspended in 0.9% NaCl in a cell concentration of 5×10e6 cells/ml. 0.5×10e6 cells (Tc99-labelled) or 1×10e6 cells ([$^3$H]-2DG labelled) were injected intravenously (i.v) in the tail vein in 100 µl 0.9% NaCl. After 1 and 12 hours, the animals were sacrificed and tissues samples were prepared. Bone marrow was collected from femoral bones in 1 ml 0.9% NaCl. Radioactivity was measured by $^3$H or gamma counting (Wallac, Finland).

Results and Discussion

The staining of BMMSCs with and without enzymatic in vitro fucosylation with antibodies against sialyl Lewis x (sLex) and Lewis x (Lex) epitopes is presented in Table 10. The anti-sLex antibodies CSLEX and HECA-452 and the anti-Lex antibody TG-1 stain the native cells only minimally, whereas CHO-131 stains 52% of the native cells. Labeling with all of the three antibodies increases when the cells are enzymatically α1,3-fucosylated indicating a very successful cell surface α1,3-fucosylation. The results also indicate, that although all three antibodies recognize fucosylated epitopes, CHO-131 binding is less dependent on fucose than the binding of the other anti-sLex and anti-Lex antibodies.

Example 18

Effect of Enzymatic Cell Surface Glycomodification on MSC Proliferation Behavior Materials and Methods Umbilical cord blood-derived mesenchymal stem cells (UCBMSC) in 70% confluency were detached with TrypLE Express (Gibco) for 6 minutes. The cell detachment was stopped by adding excess of αMEM supplemented with 10% human serum albumin (HSA) (Albumin SPR, Sanquin, the Netherlands). Viability of the detached UCBMSCs was studied by Trypan blue exclusion. The detached cells were centrifuged 300×g for 4 min, the supernatant was completely removed and cells were resuspended in enzyme reaction buffer composed of Minimum Essential Medium (MEM) cc medium supplemented with 0.5% HSA (reaction buffer control).

1×10$^6$ cells per reaction were incubated with glycosylation enzymes and sugar donors in the following way: 200 mU Neuraminidase from *Vibrio cholerae* for 1 h, 200 mU rat recombinant (*Spodoptera frugiperda*) α2,3-(N)-Sialyltransferase III (SAT) (Calbiochem) and 1 mg CMP-Neu5Ac for 1 h, Neuraminidase from *Vibrio cholerae* for 1 h followed by SAT and 1 mg CMP-Neu5Ac for the same cells for 1 h. The neuraminidase treated cells that were also treated with SAT, were washed twice with PBS between the treatments. Parallel reactions with cells only in the reaction buffer without the enzymes were also included in the experiment. Prior to the experiment, the original enzyme buffers were exchanged to the above mentioned reaction buffer with Microcon Ultracel YM 10 (Millipore). The UCB-MSC cell suspensions were incubated in +37° C., 5% CO$_2$ cell incubator in conical tubes (15 ml Falcon tubes, Nunc). To prevent cells to re-adhere to each others or surface of the tubes, the reactions were mixed by mechanical pipetting using ART 1000E filter tips (Molecular BioProducts) with M1000 micropipette (Biohit) every 30 minutes during the incubation. When the reactions were collected the number of cells and cell viability were determined.

After the treatments cells from each reaction were plated 1000 cells per cm$^2$ and incubated in +37° C., 5% CO$_2$ cell incubator in proliferation medium (Minimum Essential Medium (MEM) cc medium supplemented with 10% fetal calf serum (Gibco), 50 nM dexamethasone (Sigma), 10 ng/ml EGF (Sigma), 10 ng/ml rhPDGF-BB (R&D), 100 U/ml penicillin (Gibco), 1% streptomycin (Gibco)). As a control, proliferating cells without any treatments were plated 1000 cells per cm$^2$. After six days nearly confluent cells were detached with TrypLE Express (Gibco) and the number of cells was determined.

Results and Discussion

Cell viability was unchanged after the enzymatic glycomodification and always >90%. No changes were seen in the proliferation behavior and morphology of in vitro cell surface glycomodified MSCs, when the reaction buffer consists of cell culture media supplemented with 0.5% HSA (Table 11 and FIG. 13).

Example 19

Analysis of Suitable Medium

Materials and Methods

Materials: StemPro MSC SFM and StemPro MSC SFM+ XF, 100× Supplement (Invitrogen; Prante et al., 2009, "A Closed, Xenogeneic-Free Isolation and Expansion System for Human Mesenchymal Stromal Cells", Abstract at the 3rd International workshop on multipotent stromal cells (MSCs) for regenerative medicine and immune regulation, Frankfurt, Germany.)

Glycan isolation: 10 µl of 100×XF Supplement is subjected to N-glycosidase F digestion in 100 µl total reaction volume (Nyman et al. 1998 Eur. J. Biochem.). Similarly, potential glycoproteins are analyzed from precipitation by ice-cold acetone (Verostek et al.) of 37.5 µl of medium XF supplemented xenofree medium in 50 µl of total reaction volume. Sialylated N-glycans are isolated by graphitized carbon microcolumn solid-phase extraction (Hemmoranta et al. 2007 Exp. Hematol.).

Glycan analysis: Sialylated N-glycans are analyzed by MALDI-TOF MS in negative ion linear mode (Heiskanen et al. Glycoconj. J. in press). Neu5Gc content is analyzed by calculating relative intensities of indicator signals (m/z 1946, 2237, and 2256) and Neu5Ac indicator signals (m/z 1930 and 2221/2222) (Heiskanen et al. 2007 Stem Cells). Also neutral N-glycans are analyzed by MALDI-TOF MS in positive ion reflector mode.

N-Glycan Analysis of a Cell Culture Medium Suitable for Glycomodification and its Components We have Earlier Reported on Neu5Gc in Different Cell Culture Media. Invitrogen has Developed a new cell culture medium which is claimed to be serum free and free from any kind of animal derived material.

Sialylated N-glycans are analyzed by MALDI-TOF MS in negative ion linear mode. Neu5Gc content was analyzed by calculating relative intensities of indicator signals (m/z 1946, 2237, and 2256) and Neu5Ac indicator signals (m/z 1930 and 2221/2222). Neu5Gc indicator signals were not found either from medium or supplement.

Signals from acidic N-glycans of StemPro MSC SFM XF, 100× Supplement are observed. Main peaks are S2H5N4 and S1H5N4 (FIG. 14). S1H5N4 and S2H5N4 are typical human transferrin N-glycan monosaccharide compositions. Regarding the other N-glycan structures that were found, human serum transferrin has been reported to contain trace amounts of fucosylation and the relative proportions of bi- and triantennary structures are 9:1 (Spik et al. 1988, Biochimie 70:1459-69).

Also neutral N-glycans are analyzed. However, no neutral N-glycans are detected. Three acidic N-glycans (S1H5N4, S1H5N4F1 and S2H5N4) partially leak into neutral fraction because of huge amount of these glycans compared to neutral glycans. In StemPro MSC SFM neither neutral nor acidic N-glycans are found.

TABLE 1

Table 1. Used antibodies and lectins in FACS analysis of control and glycomodified BM-MSC:s. MAA (*Maackia amurensis*) binds to a2,3-linked sialic acids (Neu5Ac/Gcα2-3Galβ1-4GlcNAcβ1-R), SNA (*Sambucus nigra*) to α2,6-linked sialic acids (Neu5Acα2-6Gal(NAc)-R). RCA (*Ricinus communis*) and ECA (*Erythrina cristagalli*) binds mainly to Galβ1-4GlcNAcβ1-R.

| MSC immunophenotype antibodies | Plant lectins | Glycoform antibodies |
|---|---|---|
| Positive markers: CD90, CD105, CD73 HLA-ABC Negative markers: CD14, CD19, CD34, CD45 HLA-DR (FITC or PE conjugated) | MAA-FITC MAA-biotin (2°ab streptavidin FITC) SNA-FITC SNA-biotin (2°ab streptavidin FITC) RCA-FITC ECA-biotin (2°ab streptavidin FITC) | Lex GF517 (core 2 O-glycan) sLex GF526 (sLex/CSLEX1) GF516, VPU020 |

TABLE 2

Viability of BM-MSC after trypsinization in different conditions Number of BM-MSCs in 300 µl cell suspension. After 2 hours incubation in indicated conditions, the cells still in suspension were collected and their number calculated. The cells adhered to cell culture vessel bottom were not collected. Viability was determined by Trypan blue exclusion. There were less cells left in suspension after 2 h incubation in buffer containing divalent cations (α-MEM + 0.5% HSA), due to adherence to cell culture vessel if the reaction was not continuously resuspended.

| | before incubation | after 2 h no resuspension | after 2 h with resuspension |
|---|---|---|---|
| | □MEM + 0.5% HSA | | |
| live cells | 175 000 | 87 000 | 105 000 |
| dead cells | 0 | 0 | 0 |
| viability | 100% | 100% | 100% |
| | HBSS ($Ca^{2+}/Mg^{2+}$-free) + 0.1% HSA | | |
| live cells | 175 000 | 94 500 | 91 500 |
| dead cells | 0 | 3000 | 1500 |
| viability | 100% | 97% | 98% |

TABLE 3

| Sulfo-specific antibodies | |
|---|---|
| Antibody (clone) name | Specificity Comments |
| Group 1. Binds sulfo, no Sialic acid, no Fuc | |
| 1a. Specific antibodies | |
| M-DC8 | Gal(β1-4)[HSO3(-6)]GlcNAc(β1-3)Gal(β1-4)Glc(β1-)-R [1], [3] |
| DD2 | Gal(β1-4)[HSO3(-6)]GlcNAc(β1-3)Gal(β1-4)Glc(β1-)-R [1], [3] |
| 1b. Other antibodies | |
| DD1* | Gal(β1-4)[HSO3(-6)]GlcNAc(β1-3)Gal(β1-4)Glc(β1-)-R [1], [3] [HSO3(-6)]Gal(β1-4)[HSO3(-6)]GlcNAc(β1-3)Gal(β1-4)Glc(β1-)-R [HSO3(-6)]Gal(β1-4)[HSO3(-6)]GlcNAc(β1-3)[HSO3(-6)]Gal(β1-)-R * Miltenyi data sheet for Ab M-DC8 indicates this as clone name |
| Group 2. Binds sulfo and sialic acid, but no Fuc | |
| 2a. Specific antibodies | |
| KN343 | Neu5Ac(α2-6)Gal(β1-4)[HSO3(-6)]GlcNAc(β1-)-R[8] |
| Group 3. Binds sulfo and Fuc, but no sialic acid | |
| 3a. Specific antibodies | |
| AG273 | Gal(β1-4)[Fuc(α1-3)][HSO3(-6)]GlcNAc(β1-3)Gal(β1-)-R [1] |
| AG97 | Gal(β1-4)[Fuc(α1-3)][HSO3(-6)]GlcNAc(β1-3)Gal(β1-)-R [1] |
| F2 | HSO3(-3)Gal(β1-3)[Fuc(α1-4)]GlcNAc-R [1], [4] |
| 91.9H | HSO3(-3)Gal(β1-3)[Fuc(α1-4)]GlcNAc(β1-3)Gal-R [1] |
| 3b. Other antibodies | |
| AG107 | Gal(β1-4)[HSO3(-6)]GlcNAc(β1-3)Gal(β1-4)Glc(β1-)-R [1] Gal(β1-4)[Fuc(α1-3)][HSO3(-6)]GlcNAc(β1-3)Gal(β1-4)Glc(β1-)-R |
| AG223 | Gal(β1-4)[Fuc(α1-3)][HSO3(-6)]GlcNAc(β1-3)Gal(β1-4)Glc(β1-)-R [9] |
| FH-2 | Gal(β1-4)[Fuc(α1-3)]GlcNAc(β1-3)Gal(β1-)-R [2] HSO3(-6)Gal(β1-4)[Fuc(α1-3)]GlcNAc(β1-3)Gal(β1-)-R |
| 73-30 | Gal(β1-4)[Fuc(α1-3)]GlcNAc(β1-3)Gal(β1-)-R [2] HSO3(-6)Gal(β1-4)[Fuc(α1-3)]GlcNAc(β1-3)Gal(β1-)-R |
| LeuM1 | Gal(β1-4)[Fuc(α1-3)]GlcNAc(β1-3)Gal(β1-)-R [2] HSO3(-6)Gal(β1-4)[Fuc(α1-3)]GlcNAc(β1-3)Gal(β1-)-R |
| SU59 | HSO3(-3)Gal(β1-4)[Fuc(α1-3)]GlcNAc(β1-3)Gal(β1-)-R [2] |
| Group 4. Binds sulfo, sialic acid and Fuc | |
| G152 | Neu5Ac(α2-3)Gal(β1-4)[Fuc(α1-3)][HSO3(-6)]GlcNAc(β1-3)Gal(β1-)-R [2], [5] |

TABLE 3-continued

Sulfo-specific antibodies

| Antibody (clone) name | Specificity Comments |
|---|---|
| G72 | Neu5Ac(α2-3)Gal(β1-4)[Fuc(α1-3)][HSO3(-6)]GlcNAc(β1-3)Gal(β1-)-R [2], [5] |
| G2706 | Neu5Ac(α2-3)[HSO3(-6)]Gal(β1-4)[Fuc(α1-3)][HSO3(-6)]GlcNAc(β1-3)Gal(β1-)-R [2] |
| G27011 | Neu5Ac(α2-3)[HSO3(-6)]Gal(β1-4)[Fuc(α1-3)][HSO3(-6)]GlcNAc(β1-3)Gal(β1-)-R [2] |
| G27037 | Neu5Ac(α2-3)[HSO3(-6)]Gal(β1-4)[Fuc(α1-3)][HSO3(-6)]GlcNAc(β1-3)Gal(β1-)-R [2] |
| G27039 | Neu5Ac(α2-3)[HSO3(-6)]Gal(β1-4)[Fuc(α1-3)][HSO3(-6)]GlcNAc(β1-3)Gal(β1-)-R [2] |
| 2F3 | Neu5Ac(α2-3)Gal(β1-4)[Fuc(α1-3)]GlcNAc(β1-3)Gal(β1-)-R [1]<br>Neu5Ac(α2-3)[HSO3(-6)]Gal(β1-4)[Fuc(α1-3)]GlcNAc(β1-3)Gal(β1-)-R<br>Neu5Ac(α2-3)Gal(β1-4)[Fuc(α1-3)][HSO3(-6)]GlcNAc(β1-3)Gal(β1-)-R<br>Neu5Ac(α2-3)[HSO3(-6)]Gal(β1-4)[Fuc(α1-3)][HSO3(-6)]GlcNAc(β1-3)Gal(β1-)-R |
| 2H5 | Neu5Ac(α2-3)Gal(β1-4)[Fuc(α1-3)]GlcNAc(β1-3)Gal(β1-)-R [1]<br>Neu5Ac(α2-3)[HSO3(-6)]Gal(β1-4)[Fuc(α1-3)]GlcNAc(β1-3)Gal(β1-)-R<br>Neu5Ac(α2-3)Gal(β1-4)[Fuc(α1-3)][HSO3(-6)]GlcNAc(β1-3)Gal(β1-)-R<br>Neu5Ac(α2-3)[HSO3(-6)]Gal(β1-4)[Fuc(α1-3)][HSO3(-6)]GlcNAc(β1-3)Gal(β1-)-R |
| CSLEX1 | Neu5Ac(α2-3)Gal(β1-4)[Fuc(α1-3)]GlcNAc(β1-3)Gal(β1-)-R [1]<br>Neu5Ac(α2-3)[HSO3(-6)]Gal(β1-4)[Fuc(α1-3)]GlcNAc(β1-3)Gal(β1-)-R |
| HECA-452 | Neu5Ac(α2-3)Gal(β1-4)[Fuc(α1-3)]GlcNAc(β1-3)Gal(β1-)-R [2]<br>Neu5Ac(α2-3)[HSO3(-6)]Gal(β1-4)[Fuc(α1-3)]GlcNAc(β1-3)Gal(β1-)-R<br>Neu5Ac(α2-3)Gal(β1-4)[Fuc(α1-3)][HSO3(-6)]GlcNAc(β1-3)Gal(β1-)-R<br>Neu5Ac(α2-3)[HSO3(-6)]Gal(β1-4)[Fuc(α1-3)][HSO3(-6)]GlcNAc(β1-3)Gal(β1-)-R |
| SNH-3 | Neu5Ac(α2-3)Gal(β1-4)[Fuc(α1-3)]GlcNAc(β1-3)Gal(β1-)-R [2]<br>Neu5Ac(α2-3)[HSO3(-6)]Gal(β1-4)[Fuc(α1-3)]GlcNAc(β1-3)Gal(β1-)-R |

Comments:
[1] GlycoEpitope database www.glyco.is.ritsumei.ac.jp
[2] Mitsuoka & al. 1998, JBC 273: 11225
[3] Schäkel & al. 2002, Immunity 17: 289
[4] Veerman & al. 1997, Glycobiology 7: 37
[5] Ohmori & al. 2006, Blood 107:
[6] Tsubokawa & al. 2007, FEBS Journal 274: 1833
[7] Kannagi & al. 2008, Glycoconj. J.: March
[8] Kimura & al. 2007, JBC 282: 32200
[9] Izawa & al. 2000, Cancer Res. 60: 1410

TABLE 4

Tested MSC suspension incubation strategies (incubation vessel and suspension techniques). Viability was determined after 2 h with Trypan blue exclusion.

| Samples | | Viability by Trypan blue staining |
|---|---|---|
| #1 | 24-well plate NO SUSPENSION | |
| a | Buffer control 2 h | >95% |
| b | Buffer + 100 mU SAT | >95% |
| #2 | 24-well plate SUSPENSION EVERY 30 MIN | |
| a | Buffer control 2 h | >95% |
| b | Buffer + 100 mU SAT | >90% |
| #3 | 15 ml conical tube in cell culture incubator, cap open, suspension every 30 min | |
| a | Buffer control 2 h | >95% |
| b | Buffer + 100 mU SAT | >95% |
| #4 | 15 ml conical tube in 37 C water bath, cap closed, tapping every 30 min | |
| a | Buffer control 2 h | >90% |
| b | Buffer + 100 mU SAT | >90% |
| #5 | 15 ml conical tube in 37 C shaker, 150 rpm, tube tilted | |
| a | Buffer control 2 h | >95% |
| b | Buffer + 100 mU SAT | >95% |

TABLE 5

Flow cytometry with conjugated MAA and MAL-1 plant lectins and UCBMSC 391P cells in different vessels with and without enforced α2,3-sialylation. Reaction numbering as in Table 4.

|  | #1 | #2 | #3 | #4 | #5 |
|---|---|---|---|---|---|
| a2,3-SATIII-induced increase in cell surface a2,3-sialylation % increase after 2 hours | | | | | |
| MAA$^{high}$ | 9.9 | 11.7 | 12.3 | 4.6 | −2.6 |
| MAL1$^{high}$ | 7.3 | 12.3 | 8.8 | −0.2 | −0.7 |
| | normoxia | | | hypoxia | |
| Buffer-induced alterations in cell surface a2,3-sialylation % increase after 2 hours | | | | | |
| MAA$^{high}$ | 4 | 5.1 | 3.5 | 17.2 | 11.5 |
| MAL1$^{high}$ | 3.7 | 6.5 | 3.3 | 19.4 | 9.9 |
| | normoxia | | | hypoxia | |

A conical tube in cell incubator (#3) seems to be the best vessel for enzymatic modifications of MSCs according to increase in MAA and MAL-1 high populations. Evident changes in cell surface α2,3-sialylation is seen in only buffer (αMEM + 0.5% human serum albumin) incubated (no enzyme) cells in hypoxic conditions (conditions #4 and #5). Percentages indicated change as compared to control cells at time point 0.

TABLE 6

Enzymatic desialylation of UCB MSCs (391P p6) in αMEM Glutamax supplemented with A) 0.5% human serum albumin (HSA) or B) 0.5% bovine serum albumin (BSA).

| A. Incubation buffer: αMEM + 0.5% HSA | | | | | B. Incubation buffer: αMEM + 0.5% BSA | | | | |
|---|---|---|---|---|---|---|---|---|---|
| | MAA-FITC | SNA-FITC | MAL1-FITC | CHO131 | | MAA-FITC | SNA-FITC | MAL1-FITC | CHO131 |
| Control 1 | 0.80% | 99.40% | 7.70% | 99.40% | Control1 | 1.40% | 99.20% | 3.10% | 97.90% |
| Control 2 | 15.50% | 99.10% | 19.50% | 87.20% | Control2 | 37.90% | 99.10% | 42.70% | 84.40% |
| Desialylation | 6.10% | 39.20% | 10.70% | 62.60% | Desialylation | 23.40% | 62.30% | 29.70% | 39.40% |

Control 1 = time point 0,
Control 2 = buffer incubated cells (2 h),
*V. cholera* desialylation for 2 hours.

TABLE 7

List of plant lectins tested for their usability to validate changes in cell surface sialylation.

| Lectin/specificity | Manufacturer | Description |
|---|---|---|
| MAA-FITC (α2,3SA) | Ey laboratories | Combination of 2 isoforms of MAA: MAA1 and MAA2. No glycan array test of binding specificity by CFG (Consortium for Functional Glycomics). |
| MAA-biotin (α2,3SA) | Ey laboratories | Combination of 2 isoforms of MAA: MAA1 and MAA2. Not tested by CFG. |
| MAL1-FITC (α2,3SA) | Vector laboratories, #FL-1311 | Specificity tested (CFG). MAL1 binds to α2,3-sialylated and sulfated structures, prefering SAα2,3Galβ1,4GlcNAc. In addition MAL1 reconize Neu5Aca2-6Lac and GT3 glycan with chain of 3 sialic acids. MAL1-FITC has also low binding affinity to non-sialylated and non-suflated LacNAc structures. |
| MAL1-biotin (α2,3SA) | Vector laboratories, #B-1315 | See above the binding pattern for MAL1. |
| MAL2-biotin (α2,3SA) | Vector laboratories, #B-1265 | Spesificity tested by CFG. MAL2 binds to various sulphated glycan structures which may or may not carry sialic acids. Preference towards SAα2,3Galβ1,3GalNAc has been suggested (Konami Y. FEBS Lett. 1994). |
| SNA-FITC (α2,6SA) | Vector laboratories | The specificity of FITC conjugated SNA from Vector laboratories has not been tested by CFG, but SNA-biotin from the same manufacturer shows high specificity towards α2,6SA. |

TABLE 7-continued

List of plant lectins tested for their usability to validate changes in cell surface sialylation.

| Lectin/specificity | Manufacturer | Description |
| --- | --- | --- |
| LFA-FITC (SA, independent of the linkage) | EY laboratories, #F5101-1 | No tested binding specificity by CFG. |
| LFA-biotin (SA, independed of the linkage) | EY laboratories, #BA-5101-1 | No tested binding specificity by CFG. |
| ECA-biotin (terminal Gal) | Vector laboratories | Recognize terminal galactose and possibly fucosylated O-glygans. Only the binding specificity of ECA-FITC (EY laboratories) has been tested by CFG. |

TABLE 8

List of used glycoform-specific antibodies for Lewis X (Lex) and sialyl Lewis X (sLex) glycostructures to validate changes in cell surface sialylation and fucosylation.

| Antibody/specificity | Manufacturer | Description |
| --- | --- | --- |
| CHO-131, PSGL-1 sLex on core II O-glycans/sLex | R&D systems #MAB996 | SA(a3)Gal(b4)[Fuc(a3)]GlcNAc |
| CSLEX, CD15s/sLex | BD Pharmingen #551344 | SA(a3)Gal(b4)[Fuc(a3)]GlcNAc |
| TG-1, CD15/Lex | abcam #ab17080 | Gal(b4)[Fuc(a3)]GlcNAc |
| HECA-452, CLA/sLex | BD Pharmingen #555947 | SA(a3)Gal(b4)[Fuc(a3)]GlcNAc |

TABLE 9

Sia-panel expression profile in various incubation media.
The change of positively labelled cells was compared to freshly labelled cells.

| | time 0 | 2 h suspension incubation | | | | | | 40 min suspension incubation | |
| --- | --- | --- | --- | --- | --- | --- | --- | --- | --- |
| Lectin | Control levels | ☐MEM | ☐MEM + SAT | StemPro | StemPro + SAT | HBSS | HBSS + SAT | HBSS | HBSS + SAT |
| MAA | 0.90% | +7.1 | +33 | +18.9 | +25 | +6.9 | +22.2 | +2.0 | +9.8 |
| MAL-1 | 0.90% | +6.6 | +13 | +22.1 | +11.2 | +18.8 | +16.5 | +1.8 | +8.1 |
| SNA | 99.50% | +0.3 | +0.3 | +0.1 | +0.1 | +0.5 | +0.2 | +0.5 | +0.4 |

TABLE 10

Validation of α1,3-fucosylated human bo ne marrow-derived mesenchymal stem cells BMMSCs after 1 h FUTVI enzymatic glycomodification in suspension incubation in αMEM + 0.5% human serum albumin (HSA) buffer. Control cells were incubated in buffer only without enzyme.

| BMMSC cell sample | CHO-131 | CSLEX | HECA 452 | TG-1 |
| --- | --- | --- | --- | --- |
| | | % pos | | |
| buffer control | 52 | 3.8 | 0.8 | 2.1 |
| a1,3-fucosylation | 99.7 | 97.4 | 72.6 | 37.2 |

With both labeling methods, an enforced cell surface α1,3-fucosylation accomplished in cell culture media based reaction buffer (αMEM) supplemented with HSA increases targeting to the bone marrow and, interestingly, also decreases lung entrapment (FIG. 12).

TABLE 11

Number of total amount of cells in cell culture vessel 6 days after indicated glyco-modifications. All cells were plated after the glycomodification with 1000 cell per $cm^2$. Both untreated cells and reaction buffer only incubated cells served as controls.

| Reaction | number of cells * $10^6$ |
| --- | --- |
| Neuraminidase 1 h | 1,970 |
| Neuraminidase 1 h + SAT 1 h | 1,987 |
| SAT 1 h | 2,043 |
| incubation control | 2,113 |
| untreated cells | 1,953 |

TABLE 12

Components of α-MEM culture medium (Invitrogen Life Science).

| COMPONENTS | Molecular Weight | Concentration (mg/L) | mM |
|---|---|---|---|
| Amino Acids | | | |
| Glycine | 75 | 50 | 0.667 |
| L-Alanine | 89 | 25 | 0.281 |
| L-Alanyl-L-Glutamine | 203 | 406 | 2 |
| L-Arginine | 211 | 105 | 0.498 |
| L-Asparagine-H2O | 132 | 50 | 0.379 |
| L-Aspartic acid | 133 | 30 | 0.226 |
| L-Cysteine hydrochloride | 121 | 100 | 0.826 |
| L-Cystine | 313 | 31 | 0.099 |
| L-Glutamic Acid | 147 | 75 | 0.51 |
| L-Histidine | 155 | 31 | 0.2 |
| L-Isoleucine | 131 | 52.4 | 0.4 |
| L-Leucine | 131 | 52.4 | 0.4 |
| L-Lysine | 146 | 58 | 0.397 |
| L-Methionine | 149 | 15 | 0.101 |
| L-Phenylalanine | 165 | 32 | 0.194 |
| L-Proline | 115 | 40 | 0.348 |
| L-Serine | 105 | 25 | 0.238 |
| L-Threonine | 119 | 48 | 0.403 |
| L-Tryptophan | 204 | 10 | 0.049 |
| L-Tyrosine | 181 | 36 | 0.199 |
| L-Valine | 117 | 46 | 0.393 |
| Vitamins | | | |
| Ascorbic Acid | 176 | 50 | 0.284 |
| Biotin | 244 | 0.1 | 0.00041 |
| Choline chloride | 140 | 1 | 0.00714 |
| D-Calcium pantothenate | 477 | 1 | 0.0021 |
| Folic Acid | 441 | 1 | 0.00227 |
| Niacinamide | 122 | 1 | 0.0082 |
| Pyridoxal hydrochloride | 204 | 1 | 0.0049 |
| Riboflavin | 376 | 0.1 | 0.000266 |
| Thiamine hydrochloride | 337 | 1 | 0.00297 |
| Vitamin B12 | 1355 | 1.36 | 0.001 |
| i-Inositol | 180 | 2 | 0.0111 |
| Inorganic Salts | | | |
| CaCl2—2H2O | 147 | 264 | 1.8 |
| MgSO4—7H2O | 246 | 200 | 0.813 |
| KCl | 75 | 400 | 5.33 |
| NaHCO3 | 84 | 2200 | 26.19 |
| NaCl | 58 | 6800 | 117.24 |
| NaH2PO4—2H2O | 156 | 158 | 1.01 |

TABLE 12-continued

Components of α-MEM culture medium (Invitrogen Life Science).

| COMPONENTS | Molecular Weight | Concentration (mg/L) | mM |
|---|---|---|---|
| Other Components | | | |
| D-Glucose (Dextrose) | 180 | 1000 | 5.56 |
| Lipoic Acid | 206 | 0.2 | 0.000971 |
| Phenol Red | 376.4 | 10 | 0.0266 |
| Sodium Pyruvate | 110 | 110 | 1 |

The invention claimed is:

1. A method for in vitro enzymatic modification of the glycosylation of viable human mesenchymal stem cells to increase an amount of core 2 sLex structures on a human mesenchymal stem cell surface, the method comprising the step of contacting the human mesenchymal stem cells in serum free culture medium with a fucosyltransferase, wherein said culture medium contains divalent cations $Mg^{2+}$ and $Ca^{2+}$ and wherein both $Mg^{2+}$ and $Ca^{2+}$ ions are used in a concentration of at least 0.05 mM, and wherein said human mesenchymal stem cells are from an aggregating or surface-adherent cell culture, wherein adherent human mesenchymal stem cells are detached from the cell culture surface, and said human mesenchymal stem cells are contacted with the fucosyltransferase in conditions that prevent adhesion of the human mesenchymal stem cells and wherein adherence of the human mesenchymal stem cells is inhibited by providing shear force when human mesenchymal stem cells are contacted with the fucosyltransferase, and wherein human mesenchymal stem cells are cultured and contacted with a fucosyltransferase in serum free culture medium.

2. The method according to claim 1 further comprising a step of incubating the cells with an inhibitor or substrate of the fucosyltransferase.

3. The method according to claim 1, wherein the fucosyltransferase is selected from the group consisting of FTIII, FTIV, FTV, FTVI, FTVII and FTIX.

4. The method according to claim 1, wherein the fucosyltransferase is a human fucosyltransferase.

5. The method according to claim 1, wherein the human mesenchymal stem cells are derived from bone marrow or cord blood.

6. The method according to claim 1, wherein the culture medium comprises a non-glycoprotein substantially without acceptor glycans for glycosyltransferase.

* * * * *